United States Patent
Tam

(10) Patent No.: US 11,174,298 B2
(45) Date of Patent: Nov. 16, 2021

(54) PREPARATION AND USE OF GINSENTIDES AND GINSENTIDE-LIKE PEPTIDES

(71) Applicant: James P. Tam, Singapore (SG)

(72) Inventor: James P. Tam, Singapore (SG)

(73) Assignee: James P. Tam, Singapore (SG)

( * ) Notice: Subject to any disclaimer, the term of this patent is extended or adjusted under 35 U.S.C. 154(b) by 0 days.

(21) Appl. No.: 16/348,770

(22) PCT Filed: Nov. 9, 2017

(86) PCT No.: PCT/SG2017/050561
§ 371 (c)(1),
(2) Date: May 9, 2019

(87) PCT Pub. No.: WO2018/088962
PCT Pub. Date: May 17, 2018

(65) Prior Publication Data
US 2020/0277343 A1 Sep. 3, 2020

(30) Foreign Application Priority Data
Nov. 9, 2016 (SG) .......................... 10201609388X

(51) Int. Cl.
| | | |
|---|---|---|
| *C07K 14/415* | (2006.01) | |
| *A61P 7/02* | (2006.01) | |
| *C07K 14/00* | (2006.01) | |
| *A61K 38/00* | (2006.01) | |

(52) U.S. Cl.
CPC .............. *C07K 14/415* (2013.01); *A61P 7/02* (2018.01); *C07K 14/001* (2013.01); *A61K 38/00* (2013.01)

(58) Field of Classification Search
CPC .... C07K 14/415; C07K 14/001; C07K 14/00; A61P 7/02; A61P 9/12; A61P 9/10; A61P 9/00; A61P 43/00; A61P 39/02; A61P 3/02; A61K 38/00; A61K 38/168
See application file for complete search history.

(56) References Cited

U.S. PATENT DOCUMENTS

2011/0085996 A1   4/2011  Yeom et al.

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Behrendt et al., "Advances in Fmoc sold-phase peptide synthesis," *J. Pept. Sci.* 22:4-27, 2016.
Geneseq, "Panax ginseng-specific abundant protein 3 (GSAP3) SEQ ID 6," Accession No. ARZ16707, Aug. 7, 2008. (1 page).
Miriam Góngora-Benitez et al., "Optimized Fmoc Solid-Phase Synthesis of the Cysteine-Rich Peptide Linaclotide," *Biopolymers* 96(1):69-90, 2010.
UniProt, "SubName: Full=Uncharacterized protein {ECO:0000313:EMBL:ABX75544.1}," Accession No. A9QMA6, Feb. 5, 2008. (1 page).
Abraham et al., "The Liposomal Formulation of Doxorubicin," *Methods in Enzymology* 391:71-97, 2005.
Ancelin et al., "Targeting Assay to Study the cis Functions of Human Telomeric Proteins: Evidence for Inhibition of Telomerase by TRF1 and for Activation of Telomere Degradation by TRF2," *Molecular and Cellular Biology* 22(10):3474-3487, 2002.
Blackburn, "Switching and Signaling at the Telomere," *Cell* 106:661-673, 2001.
Blasco, "Telomeres and Human Disease: Ageing, Cancer and Beyond," *Nat. Rev. Genet.* 6:611-622, 2005.
Bos et al., "OctoDEX™—Controlled Release of Pharmaceutical Proteins from Hydrogels," *Business Briefing: Pharmatech* 2003:1-6, 2003.
Buettner et al., "Systematic Review of the Effects of Ginseng on Cardiovascular Risk Factors," *The Annals of Pharmacotherapy* 40:83-95, 2006.
Carter et al., "High Level *Escherichia Coli* Expression and Production of a Bivalent Humanized Antibody Fragment," *Biotechnology* 10:163-167, 1992.
Casper et al., "A Prospective Randomized Trial of Adjuvant Chemotherapy With Bolus Versus Continuous Infusion of Doxorubicin in Patients With High-Grade Extremity Soft Tissue Sarcoma and an Analysis of Prognostic Factors," *Cancer* 68(6):1221-1229, 1991.
Chan et al., "Ginseng Extracts Restore High-Glucose Induced Vascular Dysfunctions by Altering Triglyceride Metabolism and Downregulation of Atherosclerosis-Related Genes," *Evidence-Based Complementary and Alternative Medicine*:1-13, 2013.
Chatterjee et al., "Doxorubicin Cardiomyopathy," *Cardiology* 115:155-162, 2010.
Cheneval et al., "Fmoc-Based Synthesis of Disulfide-Rich Cyclic Peptides," *J. Org. Chem.* 79:5538-5544, 2014.
Chi et al., "Genetic and Physiological Dissection of the Vertebrate Cardiac Conduction System," *PLOS Biology* 6(5):1006-1019, 2008.
Collins et al., "Telomerase in the human organism," *Oncogene* 21:564-579, 2002.
Corpet, "Multiple sequence alignment with hierarchical clustering," *Nucleic Acids Research* 16(22):10881-10890, 1988.
De Lange, "Protection of mammalian telomeres," *Oncogene* 21:532-540, 2002.
Fyhrquist et al., "The roles of senescence and telomere shortening in cardiovascular disease," *Nat. Rev. Cardiol.* 10:1-10, 2013.
Higgins et al., "CLUSTAL: a package for performing multiple sequence alignment on a microcomputer," *Gene* 73:237-244, 1988.
Higgins et al., "Fast and sensitive multiple sequence alignments on a microcomputer," *Cabios Communications* 5(2):151-153, 1989.

(Continued)

*Primary Examiner* — Sudhakar Katakam
(74) *Attorney, Agent, or Firm* — Seed IP Law Group LLP

(57) ABSTRACT

The present invention relates to the methods of solid-phase peptide synthesis or recombinant production of ginsentide or ginsentide-like peptides or salts thereof. Further provided are uses of the ginsentide or ginsentide-like peptides or salts thereof as α1-adrenergic receptor antagonists and vasorelaxants, nitric oxide-boosting agents, anti-thrombotic agents, anti-atherosclerotic agents, as protective agents against doxorubicin-induced cardiotoxicity, anti-ageing and adaptogenic agents, nutraceuticals, health supplements, or cosmetic ingredients.

2 Claims, 37 Drawing Sheets
Specification includes a Sequence Listing.

(56) References Cited

OTHER PUBLICATIONS

Huang et al., "Parallelization of a local similarity algorithm," *Cabios* 8(2):155-165, 1992.

International Search Report and Written Opinion, dated Jan. 24, 2018, for International Application No. PCT/SG2017/050561, 14 pages.

Jin et al., "Antithrombotic and Antiplatelet Activities of Korean Red Ginseng Extract," *Basic & Clinical Pharmacology & Toxicology* 100:170-175, 2007.

Klint et al., "Production of Recombinant Disulfide-Rich Venom Peptides for Structural and Functional Analysis via Expression in the Periplasm of *E. coli*," *PLOS One* 8(5):1-12, 2013.

Legha et al., "Clinical and Pharmacologic Investigation of the Effects of α-Tocopherol on Adriamycin Cardiotoxicity," *Annals New York Academy of Sciences* 393:411-418, 1982.

Legha et al., "Reduction of Doxorubicin Cardiotoxicity by Prolonged Continuous Intravenous Infusion," *Annals of Internal Medicine* 96(2):133-139, 1982.

Lehenbauer et al., "A concise description of cardioprotective strategies in doxorubicin-induced cardiotoxicity," *Can. J. Physiol. Pharmacol.* 87:756-763, 2009.

Lipshultz et al., "Late cardiac effects of doxorubicin therapy for acute lymphoblastic leukemia in childhood," *The New England Journal of Medicine* 324(12): 808-815, 1991.

Lipshultz et al., "The Effect of Dexrazoxane on Myocardial Injury in Doxorubicin-Treated Children with Acute Lymphoblastic Leukemia," *The New England Journal of Medicine* 351(2):145-153, 2004.

Myers et al., "A Randomized Controlled Trial Assessing the Prevention of Doxorubicin Cardiomyopathy by N-Acetylcysteine," *Seminars in Oncology* 10(Suppl. 1):53-55, 1983. (4 pages).

Nah et al., "Ginsenosides: Are Any of them Candidates for Drugs Acting on the Central Nervous System?," *CNS Drug Reviews* 13(4):381-404, 2007.

Nguyen, "Discovery and Characterization of Novel Peptide Biologics in Herbal Medicine," Doctor of Philosophy thesis, School of Biological Sciences, Nanyang Technological University, pp. 1-261, 2011.

Needleman et al., "A General Method Applicable to the Search for Similarities in the Amino Acid Sequence of Two Proteins," *J. Mol. Biol.* 48:443-453, 1970.

Patton et al., "The Lungs as a Portal of Entry for Systemic Drug Delivery," *Proc. Am. Thorac. Soc.* 1:338-344, 2004.

Pearson et al., "Improved tools for biological sequence comparison," *Proc. Natl. Acad. Sci. USA* 85:2444-2448, 1988.

Pearson, "Chapter 26: Using the FASTA Program to Search Protein and DNA Sequence Databases," in Griffin et al. (eds.), *Methods in Molecular Biology 24: Computer Analysis of Sequence Data(Part I)*, 1994, pp. 307-331.

Peterson et al., "Designing Zebrafish Chemical Screens," *Methods in Cell Biology* 105:525-541, 2011.

Raj et al., "Anthracycline-Induced Cardiotoxicity: A Review of Pathophysiology, Diagnosis, and Treatment," *Curr. Treat. Options Cardio. Med.* 16(315):1-14, 2014.

Shin et al., "Korean red ginseng inhibits arginase and contributes to endothelium-dependent vasorelaxation through endothelial nitric oxide synthase coupling," *Journal of Ginseng Research* 37(1):64-73, 2013.

Smith et al., "Comparison of Biosequences," *Advances in Applied Mathematics* 2:482-489, 1981.

Swain et al., "Cardioprotection With Dexrazoxane for Doxorubicin-Containing Therapy in Advanced Breast Cancer," *Journal of Clinical Oncology* 15(4):1318-1332, 1997.

Tacar et al., "Doxorubicin: an update on anticancer molecular action, toxicity and novel drug delivery systems," *Journal of Pharmacy and Pharmacology* 65:157-170, 2012.

Tebbi et al., "Dexrazoxane-Associated Risk for Acute Myeloid Leukemia/Myelodysplastic Syndrome and Other Secondary Malignancies in Paediatric Hodgkin's Disease," *Journal of Clinical Oncology* 25(5):493-500, 2007.

Thorn et al., "Doxorubicin pathways: pharmacodynamics and adverse effects," *Pharmacogenetics and Genomics* 21:440-446, 2011.

Van Steensel et al., "Control of telomere length by the human telomeric protein TRF1," *Nature* 385:740-743, 1997.

Venturi et al., "High Level Production of Functional Antibody Fab Fragments in an Oxidizing Bacterial Cytoplasm," *J. Mol. Biol.* 315:1-8, 2002.

Wouters et al., "Protecting against anthracycline-induced myocardial damage: a review of the most promising strategies," *British Journal of Haematology* 131:561-578, 2005.

Wu et al., "XPF with mutations in its conserved nuclease domain is defective in DNA repair but functions in TRF2-mediated telomere shortening," *DNA Repair* 6:157-166, 2007.

You et al., "*Panax ginseng* Reduces Adriamycin-Induced Heart Failure in Rats," *Phytotherapy Research* 19:1018-1022, 2005.

Kalouda, et al., "The nitric oxide donor molsidomine induces anxiolytic-like behaviour in two different rat models of anxiety," *Pharmacology, Biochemistry and Behavior*, vol. 138, 2015, pp. 111-116.

Kang, et al., "Ginsenosides of the Protopanaxatriol Group Cause Endothelium-Dependent Relaxation in the Rat Aorta," *Life Sciences*, vol. 56:19, 1995, pp. 1577-1586.

Kim, et al., "Ginsenosides Protect Pulmonary Vascular Endothelium Against Free Radical-Induced Injury," *Biochemical and Biophysical Research Communications*, vol. 189:2, 1992, pp. 670-676.

Kumar, et al., "Role of nitric oxide in stress-induced anxiety: from pathophysiology to therapeutic target," *Vitamins and hormones*, vol. 103, 2017, pp. 147-167.

Li, et al., "Comparison of $N_2O$- and chlordiazepoxide-induced behaviors in the light/dark exploration test," *Pharmacology, Biochemistry and Behavior*, vol. 68, 2001, pp. 789-796.

Smriga, et al., "Oral treatment with L-lysine and L-arginine reduces anxiety and basal cortisol levels in healthy humans," *Biomedical Research*, vol. 28 (2), 2007, pp. 85-90.

Ha et al., "A ginseng-specific abundant protein (GSAP) located on the cell wall is involved in abiotic stress tolerance," *Gene* 386: 115-122, 2007.

* cited by examiner

FIG. 7
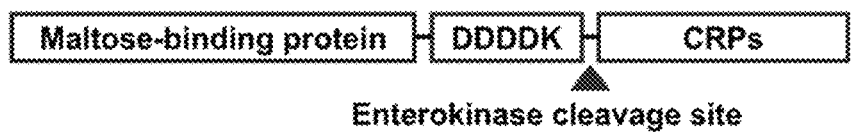
Scheme for the purification of recombinant CRPs
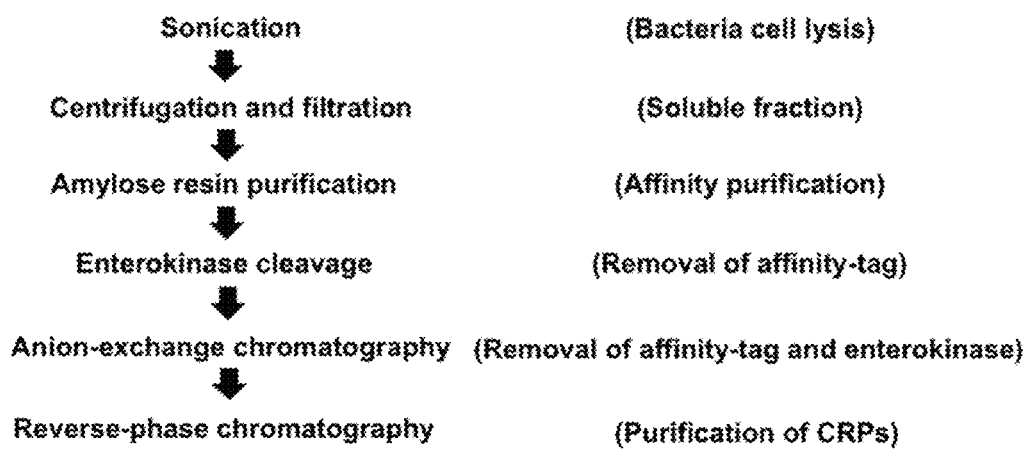
FIG. 8
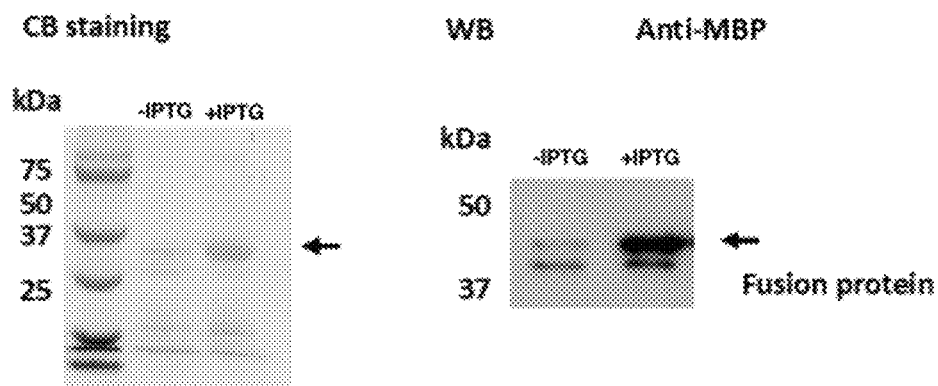

FIG. 13
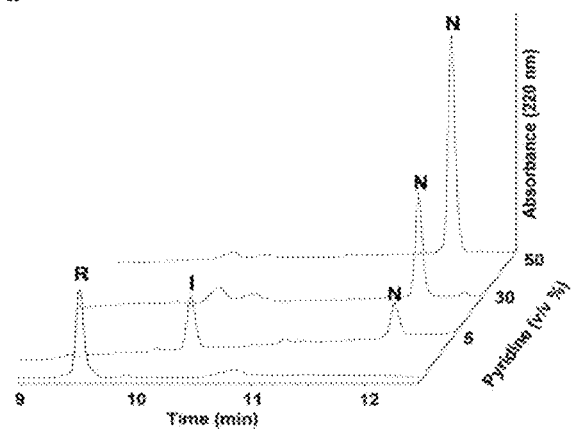
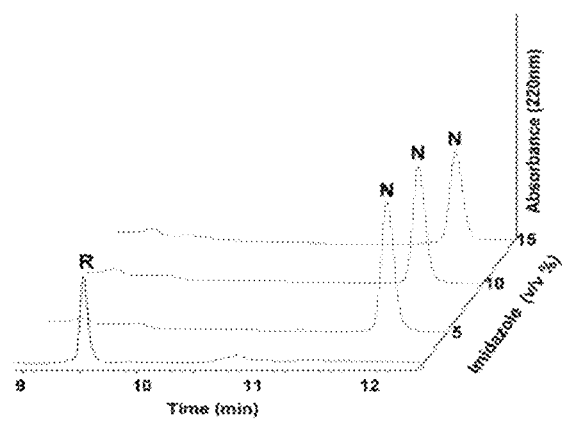
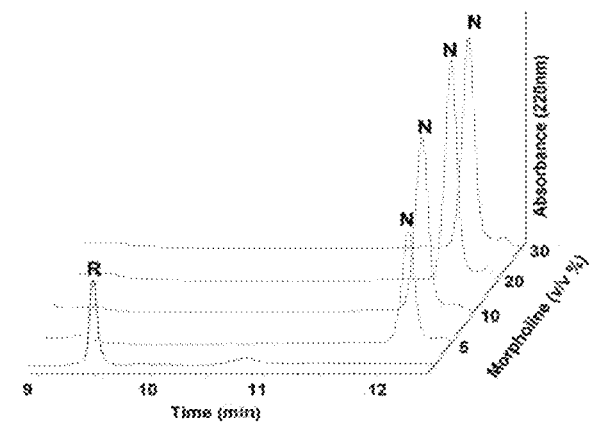

A. Purification (plant)

FIG. 25
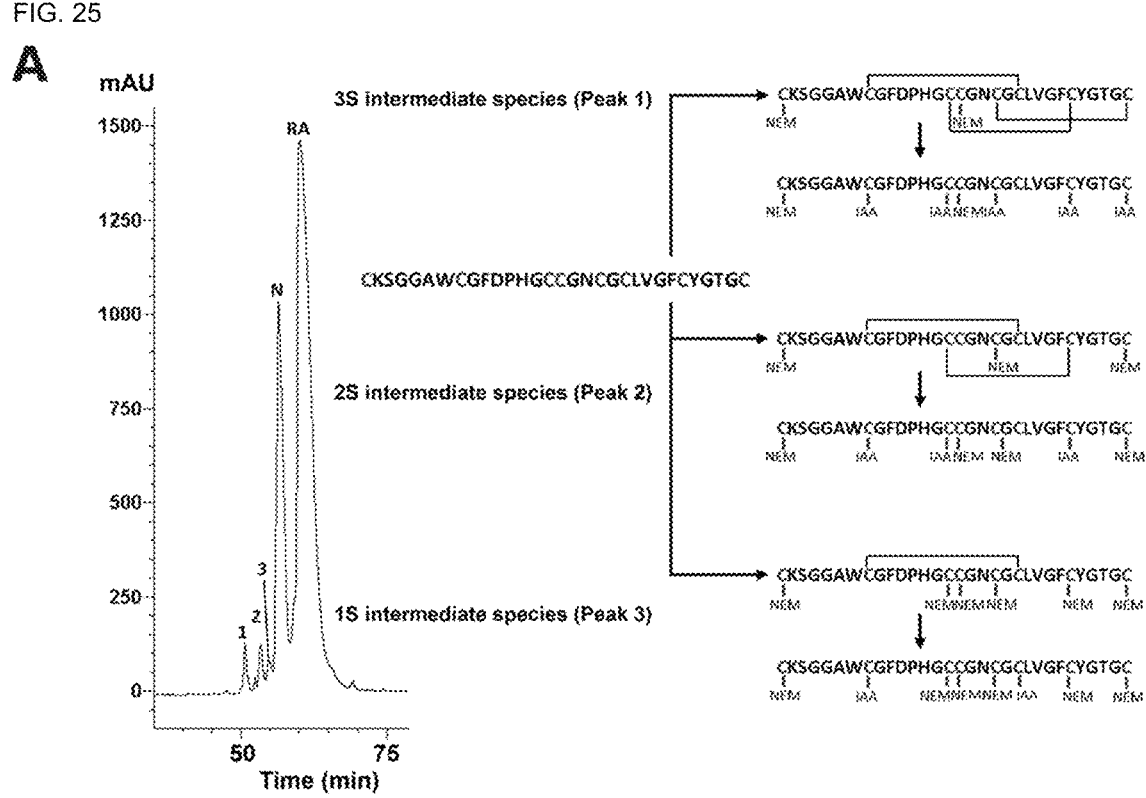
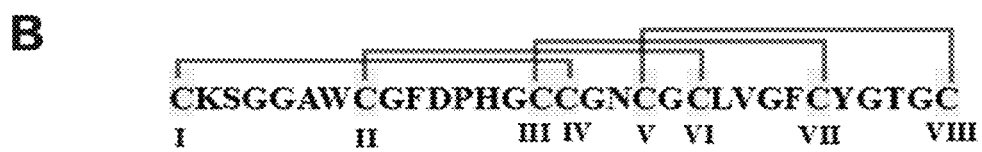
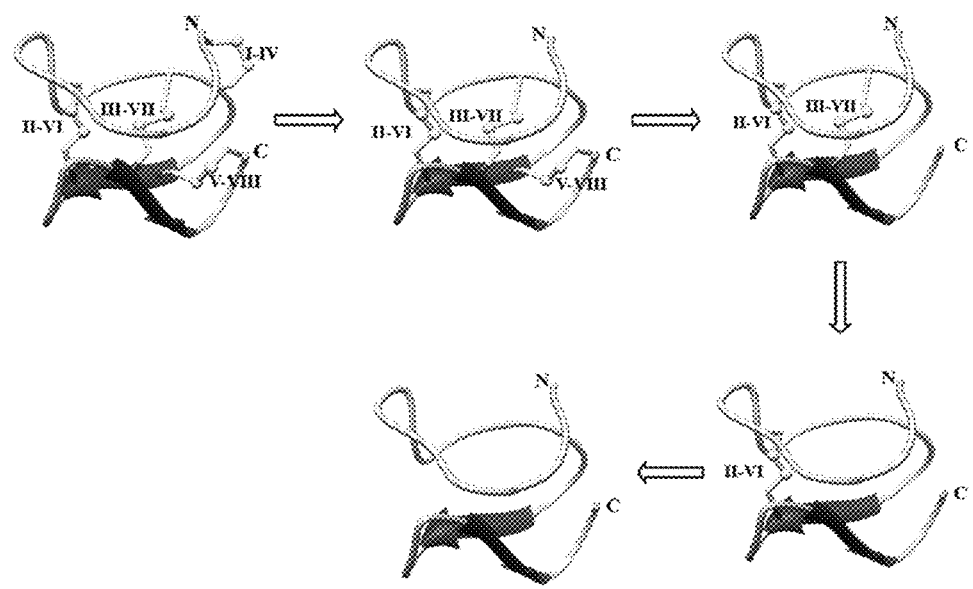

FIG. 26

```
                                        SPase
                                          ✂
        ┌─────────────────────────┬──────────────────────────────────────┐
        │     Signal peptide      │            Pro-domain                │
        └─────────────────────────┴──────────────────────────────────────┘
              10        20        30        40        50        60
TP1     MENKKVALVVV--AMVVLISTFAPLALAADEAGRSDGGNGDLIAVESVSRSNGGNGDSVTVDTVSW
TP2     MENKKVALVVV--AMVVLISTFAPLALAADEAGRSDGGNGDLIAVESVSRSNGGNGDSVTVDTVSW
TP3     ---NKKVALVVV--AMVVLISTVAPLAMAVDDAGSSDG----LIAVESVSRSNGGNGDSVAVDTVSW
TP4     ..................................................................
TP5     MENKKVALVVV--AMVVLISTFAPLALAADEAGSSDGGNGDLIAVESVSRSNGFNGDSVAVDTVSR
TP6     MENKKVALVVLLAAMAVLTDLTLA----TDDKAGHSDG-----------GADRSNGGN--EVLIDAPGR
TP7     MENKKVALVVV--AMVVLISTFAPLALAADEAGRSDGGNGDLIAVESVSRSNGGNGDSVTVDTVSW
TP8     MDNKKVALVVV--AMVVLISTFAPLALAADEAGRSDGGNGDLIAVESVSRSNGGNGDSVTVDTVSW
TP9     --------VAV--AMVVLISTFAPLALAADEAGRSDGGNGDLIAVESVSRSNGGNGDSVTVDTVSW
TP10    MDNKKVALVVV--AMVVLISTFAPLALAADEAGRSDGGNGDLIAVESVSRSNGGNGDSVTVDTVSW
TP11    ..................................................................
TP12    ----------------MVVLTDLILA----ADDMADHSDG----------GTDISDGGN--EVLIDASAG
TP13    ----------------MAVLTDLTLA----ADDKAGHSDG----------GADRSDGGN--EVLIDAPGG
TP14    MENKKVAVMVV--VLAIMLALAIA-----SREAGHSGD----------------------DPGTG ✂
        ┌─────────────────────────┬──────────────────────────────────────┐
        │       Pro-domain        │         Mature ginsentide            │
        └─────────────────────────┴──────────────────────────────────────┘
              70        80        90       100       110       120
TP1     VSSNRKTLRSSIFLPQGYLPDGGLGCKSGGAWCGFD-PHGCCG--NCGCLV--GFCYGTGC-
TP2     VSSNRKTLRSSIFLPQGYLPDGGLGCKSSGAWCGFD-PHGCCG--NCGCLV--GFCYGTGC-
TP3     VSSNRKTLRSKIFLPQGYLPDGGLGCKSAGTWCGFD-PHGCCG--SCGCLV--GFCYGVSC-
TP4     ------------EILPDGGLGCLKNGEFCWGD-PSGCCG--NCGCLIIPGVCYGTGC-
TP5     VSSNRKTLRSNIFLPQGYLPDGGLGCKSSGAWCGFD-PHGCCG--NCGCLV--GFCYGTDC-
TP6     ASVYKNLPLSRFFLREKYLPDGGLGCIPGGGFCMFE-PLSCCV--NCGCLVPGVCY---CG
TP7     VSSNRKTLRSSIFLPQGYLPDGGLGCISGGTWCGFD-PHGCCG--NCGCLV--GFCYGTGC-
TP8     VSSNRKTLRSSIFLPQGYLPDGGLGCISSGWCGFD-LHGCCG--NCGCLV--GFCYGTGC-
TP9     VSSNRKTLRSSIFLPQGYLPDGGLGCKSGGSWCGFD-PHGCCG--NCGCLV--GFCYGTGC-
TP10    VSSNRKTLRSSIFLPQGYLPDGGLGCIFSGGWCGFD-LHGCCG--NCGCLV--GFCYGTGC-
TP11    ---------ALPDGGLGCLKNGQFCWGN-PSGCCG--NCGCLIIPGVCYGTGC-
TP12    VSFYKKLPMSRFFLRERYLPDGGLGCIPGGGFCMFE-PLSCCH--NCGCLLVPGVCY---CG
TP13    ASVYKNLPLSRFFLREKYLPDGGLGCIPNGGFCMFE-PLSCCV--NCGCILVPGVCY---CG
TP14    VR--------KMLRPEIIDPDG--SCLKVGKICLGRGLKECCPSATCGCLL--GFCIK--C-
```

TP1 treatment in hypoxic ECs
- Increases Unfolded Protein Response (UPR) pathways in hypoxic ECs
- Reduces apoptosis signaling pathways
- Reduces integrin meditated cell adhesion pathways Ginsentide TP1 reduces monocyte adhesion to hypoxic endothelial cells TP1 mediated rescues ECs from of hypoxia activation

- TP1 reduce synthesis of surface adhesion receptors in hypoxic ECs.
- TP1 reduce the leukocytes-endothelium cells interaction and reduce leukocyte adhesion.
- Prevents endothelial dysfunction mediated pathological consequences.

Ginsentide TP1 reduces unfolded proteins in different hypoxic cells

PREPARATION AND USE OF GINSENTIDES AND GINSENTIDE-LIKE PEPTIDES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 692148_401USPC_SEQUENCE_LISTING.txt. The text file is 327 KB, was created on Aug. 7, 2019, and is being submitted electronically via EFS-Web.

CROSS-REFERENCE TO RELATED APPLICATION

This application makes reference to and claims the benefit of priority of the Singapore Patent Application No. 10201609388X filed on 9 Nov. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to methods of solid-phase peptide synthesis or recombinant production of ginsentide or ginsentide-like peptides with native disulfide bonds or salts thereof and uses of the prepared ginsentide or ginsentide-like peptides or salts thereof.

BACKGROUND OF THE INVENTION

Ginseng is a traditional herbal medicine that has been used for thousands of years. It is one of the most widely used and the most valuable of all medicinal plants. Ginseng has proven to be generally safe based on its exceptionally long and widespread uses.

Plant peptides and proteins are usually underexplored as bioactive constituents for medicinal plants. Ginsentides are a class of cysteine-rich peptides in ginseng that may be exploited as bioactive peptides and drug discovery leads. However, isolation of ginsentides from plants is usually laborious and costly. Therefore, there is need in the art for methods of preparing ginsentides.

SUMMARY OF THE INVENTION

The present invention satisfies the aforementioned need in the art by providing synthetical and recombinant methods of preparing ginsentides or ginsentide-like peptides and uses thereof.

In a first aspect, the invention relates to a method of solid-phase peptide synthesis of a ginsentide or ginsentide-like peptide or a pharmaceutically acceptable salt thereof, the method comprising the steps of:
(a) synthesizing the ginsentide or ginsentide-like peptide on a solid support by stepwise coupling of Fmoc-protected, optionally further suitably side-chain protected, amino acids, dipeptides and/or oligopeptides in a linear C-terminal to N-terminal fashion, wherein addition of the glycine residue at the position corresponding to position 24 of SEQ ID NO:1 is mediated by Fmoc-(Dmb)Gly-OH;
(b) cleaving the ginsentide or ginsentide-like peptide from the solid support and deprotecting the peptide; and subsequently,
(c) performing organic oxidative folding of the ginsentide or ginsentide-like peptide to form native disulfide connections.

In various embodiments, step (a) comprises the steps of:
(i) deprotecting a first amino acid linked to the solid support by removing protective chemical groups from the first amino acid;
(ii) activating chemical groups on a second amino acid to prepare the second amino acid for coupling with the first amino acid;
(iii) coupling the activated second amino acid to the deprotected first amino acid to form a peptide from the first and second amino acids; and
(iv) successively deprotecting, and coupling a plurality of amino acids into the growing peptide chain until the ginsentide or ginsentide-like peptide is synthesized.

In various embodiments, the method comprises accelerating at least one of the deprotecting, activating, and coupling steps by applying microwave energy.

In various embodiments, the organic oxidative folding is performed in non-aqueous conditions and performed in organic solvents.

In various embodiments, the organic oxidative folding comprises folding the ginsentide or ginsentide-like peptide in an organic solvent, preferably DMSO and/or isopropanol, comprising cysteamine and/or morpholine.

In various embodiments, the organic oxidative folding is performed at 4° C.

In various embodiments, the method comprises purifying the folded ginsentide or ginsentide-like peptide or salt thereof, preferably by RP-HPLC.

In a second aspect, the invention relates to a method of recombinantly preparing a ginsentide or ginsentide-like peptide or a pharmaceutically acceptable salt thereof, the method comprising the steps of:
(a) providing a host cell comprising a polynucleotide, wherein the polynucleotide encodes a polypeptide comprising Maltose-binding protein having the amino acid sequence set forth in SEQ ID NO:65, a enterokinase cleavage sequence having the amino acid sequence set forth in SEQ ID NO:66, and the ginsentide or ginsentide-like peptide or salt thereof;
(b) culturing the host cell in a growth medium under conditions allowing production of the polypeptide, and recovering the polypeptide from the medium; and
(c) generating the ginsentide or ginsentide-like peptide or salt thereof by cleaving the polypeptide using enterokinase.

In various embodiments, the polypeptide has the amino acid sequence set forth in any one of SEQ ID NOs: 67-80.

In various embodiments, the method further comprises purification of the recombinantly produced polypeptide prior to the enterokinase cleavage, preferably by amylose resin purification.

In various embodiments, the method further comprises purification of the ginsentide or ginsentide-like peptide or salt thereof by anion-exchange chromatography and/or reverse-phase chromatography after the enterokinase cleavage.

In a third aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as an α1-adrenergic receptor antagonist and vasorelaxant.

In a fourth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as a nitric oxide-boosting agent.

In a fifth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as an anti-thrombotic agent.

In a sixth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as an anti-atherosclerotic agent.

In a seventh aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as a protective agent against doxorubicin-induced cardiotoxicity.

In an eighth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as an anti-ageing and adaptogenic agent.

In a ninth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof as a nutraceutical, a health supplement, or a cosmetic ingredient.

In accordance with all the afore-described aspects of the invention, the ginsentide or ginsentide-like peptide has (i) the amino acid sequence set forth in any one of SEQ ID NO:1-64; or (ii) the amino acid sequence sharing at least 65%, 66%, 67%, 68%, 69%, 70%, 71%, 72%, 73%, or 74%, preferably at least 75%, 76%, 77%, 78%, 79%, 80%, 81%, 82%, 83%, or 84%, even more preferably at least 85%, 86%, 87%, 88%, 89%, 90%, 91%, 92%, 93%, or 94%, most preferably at least 95%, 96%, 97%, 98%, or 99% sequence identity with the peptide of (i) over its entire sequence.

BRIEF DESCRIPTION OF THE DRAWINGS

The invention will be better understood with reference to the detailed description when considered in conjunction with the non-limiting examples and the accompanying drawings.

FIG. 7. Recombinant expression scheme for ginsentides. Peptide fragment DDDDK: SEQ ID NO:66.

FIG. 8. IPTG induced MBP-TP1 fusion protein expression.

FIG. 13. RP-UPLC profiles of oxidative folding of kB1 showing the effect of different bases. A. Conditions contained different concentrations of pyridine from 5-50%; B. Conditions contained different concentrations of imidazole from 5-15%; C. Conditions contained different concentrations of morpholine from 5-30%. All conditions contained 100 μM peptide, 100 mM cysteamine and 10% (v/v) DMSO. The profiles show the reaction performed for 1 h. "R" and "N" represent the reduced and native form of kB1. "I" represents intermediate form of kB1.

FIG. 25. (A) HPLC profile of the partially S-reduced and S-alkylated ginsentide TP1. Peaks 1, 2, 3, N, and RA contained the 3SS, 2SS, 1SS, native peptide, and fully S-NEM alkylated peptides, respectively. A schematic representation of ginsentide TP1 disulfide mapping is also shown; (B) The putative unfolding pathway of ginsentide TP1 as determined by disulfide connectivity mapping. Under our experimental conditions, the Cys I-IV bond was the first to be reduced to generate the 3SS species, followed by the Cys V-VIII bond, generating the 2SS species, then the Cys III-VII bond generating the 1SS species, and lastly the Cys II-VI bond. TP1: SEQ ID NO:1.

FIG. 26. Ginsentide-encoding transcripts from *Panax ginseng*, *Panax quinquefolius* and *Panax notoginseng* deduced from de novo assembly of transcriptome data from NCBI database. The transcriptome data used are listed as follow: *Panax notoginseng* flower (SRX378878), *Panax quinquefolius* flower (SRX062267), *Panax ginseng* flower (SRX181263), *Panax ginseng* flower (SRX378873), *Panax notoginseng* leaf (SRX378880), *Panax quinquefolius* seed (SRX529365), *Panax ginseng* root (ERX137460). SPase: signal peptidase. The amino acid sequences are set forth in SEQ ID NOs: 133-146.

DETAILED DESCRIPTION OF THE INVENTION

Figure 1:
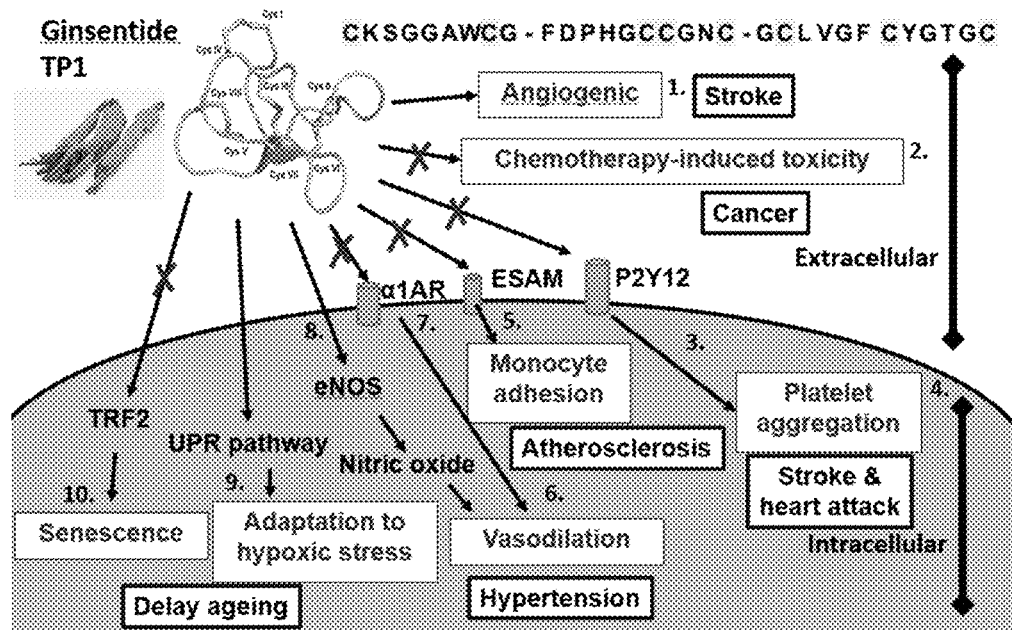
FIG. 1. Schematic diagram of the adaptogenic effects of ginsentides. TP1: SEQ ID NO:1.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

In a first aspect, the invention relates to a method of solid-phase peptide synthesis of a ginsentide or ginsentide-like peptide or a pharmaceutically acceptable salt thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, wherein the method comprises the steps of:

(a) synthesizing the ginsentide or ginsentide-like peptide on a solid support by stepwise coupling of Fmoc-protected, optionally further suitably side-chain protected, amino acids, dipeptides and/or oligopeptides in a linear C-terminal to N-terminal fashion, wherein addition of the glycine residue at the position corresponding to position 24 of SEQ ID NO:1 is mediated by Fmoc-(Dmb)Gly-OH;

(b) cleaving the ginsentide or ginsentide-like peptide from the solid support and deprotecting the peptide; and subsequently, (c) performing organic oxidative folding of the ginsentide or ginsentide-like peptide to form native disulfide connections.

The terms "peptide", "polypeptide" and "protein" are used interchangeably herein and refer to polymers of at least two amino acids connected by peptide bonds. The terms also encompass an amino acid polymer that has been modified naturally or artificially; for example, by disulfide bond formation, glycosylation, lipidation, acetylation, or phosphorylation. The term "amino acid" refers to natural and/or unnatural or synthetic amino acids, including both the D and L optical isomers, amino acid analogs (for example norleucine is an analog of leucine) and derivatives known in the art. The term "natural amino acid", as used herein, relates to the 20 naturally occurring L-amino acids, namely Gly (G), Ala (A), Val (V), Leu (L), Ile (I), Phe (F), Cys (C), Met (M), Pro (P), Thr (T), Ser (S), Glu (E), Gln (Q), Asp (D), Asn (N), His (H), Lys (K), Arg (R), Tyr (Y), and Trp (W). Generally, in the context of the present application, the peptides and polypeptides are shown in the N- to C-terminal orientation.

The term "pharmaceutically acceptable salt" as used herein means those salts of a peptide of interest that are safe and effective for administration to a mammal and that possess the desired biological activity.

The term "sequence identity" as used herein refers to the extent that two sequences are identical (i.e., on a nucleotide-by-nucleotide basis for nucleic acids or amino acid-by-amino acid basis for peptides) over a window of comparison. This is calculated by comparing two optimally aligned sequences over the window of comparison, determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity.

It should be noted that the sequence identity is always calculated in relation to a reference sequence over its entire length. In this connection, the term "window of comparison", as used herein, refers to a conceptual segment of contiguous nucleotide or amino acid positions wherein a nucleotide or amino acid sequence may be compared to a reference sequence and wherein the portion of the nucleotide or amino acid sequence in the comparison window may comprise additions or deletions (i.e., gaps) while the reference sequence does not comprise additions or deletions for optimal alignment of the two sequences.

Optimal alignment of sequences for comparison may be conducted by the local homology algorithm of Smith and Waterman, Adv. Appl. Math. 1981, 2:482; by the alignment algorithm of Needleman and Wunsch, J. Mol. Biol. 1970, 48:443; by the search for similarity method of Pearson and Lipman, Proc. Nat. Acad. Sci. U.S.A. 1988, 85:2444; or by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). The CLUSTAL program is well described by Higgins and Sharp, Gene 1988, 73:237-244; Higgins and Sharp, CABIOS 1989, 5:151-153; Corpet et al., Nucleic Acids Res. 1988, 16:10881-10890; Huang et al, Computer Applications in the Biosciences 1992, 8:155-165; and Pearson et al., Methods in Molecular Biology 1994, 24:307-331. Alignment is also often performed by inspection and manual alignment.

It should be noted that the peptide sequences described herein only define the primary structure of the peptides, i.e. the sequence of amino acids, without including any information about the disulfide bridges (—S—S—) that may be existing in the peptides. Disulfide bridges are produced by the oxidative folding of two different thiol groups (—SH) present in the peptides. The peptides described herein contain at least eight different thiol groups (i.e. eight cysteine residues each containing a thiol group) and may theoretically form zero, one, two, three, four, or more intramolecular disulfide bridges. However, it should be understood that the peptides in the context of the whole application comprise native disulfide connectivity (i.e. Cys I-IV, Cys II-VI, Cys III-VII, and Cys V-VIII) as illustrated in Table 1.

Preferred embodiments of ginsentides and ginsentide-like peptides in accordance with the present application are described in Table 1 and Table 2.

TABLE 1

Amino acid sequence of ginsentides

| Ginsentide | Amino acid sequence | SEQ ID | mRNA expression |
|---|---|---|---|
| TP1 | CKSGGAWCGFD-PHGCCG--NCGCLV--GFCYGTGC- | 1 | PG, PN |
| TP2 | CKSSGAWCGFD-PHGCCG--NCGCLV--GFCYGTGC- | 2 | PG, PQ |
| TP3 | CKSAGTWCGFD-PHGCCG--SCGCLV--GFCYGVSC- | 3 | PG, PQ |
| TP4 | CLKNGEFCWGD-PSGCCG--NCGCLIIPGVCYGTGC- | 4 | PG |
| TP5 | CKSSGAWCGFD-PHGCCG--NCGCLV--GFCYGTDC- | 5 | PG, PQ |
| TP6 | CIPGGGFCMFE-PLSCCV--NCGCILVPGVCY---CG | 6 | PG, PQ |
| TP7 | CKSGGTWCGFD-PHGCCG--NCGCLV--GFCYGTGC- | 7 | PG |
| TP8 | CISSGGWCGFD-LHGCCG--NCGCLV--GFCYGTGC- | 8 | PQ |
| TP9 | CKSGGSWCGFD-PHGCCG--NCGCLV--GFCYGTGC- | 9 | PQ |
| TP10 | CIFSGGWCGFD-LHGCCG--NCGCLV--GFCYGTGC- | 10 | PQ |
| TP11 | CLKNGQFCWGN-PSGCCG--NCGCLIIPGVCYGTGC- | 11 | PQ |
| TP12 | CIPGGGFCMFE-PLSCCH--NCGCLLVPGVCY---CG | 12 | PQ |
| TP13 | CIPNGGFCMFE-PLSCCV--NCGCILVPGVCY---CG | 13 | PN |
| TP14 | CLKVGKICLGRGLKECCPSATCGCLL--GFCIK--C- | 14 | PQ |

Each "G" in bold indicates a glycine residue introduced by Fmoc-(Dmb)Gly-OH during the solid-phase peptide synthesis.

PG: *Panax ginseng*; PN: *Panax notoginseng*; PQ: *Panax quinquefolius*.

Disulfide connectivity: Cys I-IV, Cys II-VI, Cys III-VII and Cys V-VIII.

TABLE 2

Amino acid sequence of preferred ginsentide-like peptides

| SEQ ID | Source | Amino acid sequence |
|---|---|---|
| 15 | *Angiopteris evecta* | CIPKGGWCLFDIMGCCKPCGCLAGFCWVVGDDCN |
| 16 | *Amaranthus retroflexus* | CVPKGTPCLYKPEPCCGANCFCDTSAYTFQYVCKCY |
| 17 | *Agrostis stolonifera* | CLPSGGFCMFRPTDCCGNCGCLYPVGVCYGSRCEE |
| 18 | *Blasia sp.* | CLKNGEFCWGDPSGCCGNCGCLIIPGVCYGTGC |
| 19 | *Bazzania trilobata* | CLNGGGYCGSFTREACCYNCVCMMAFCVCG |
| 20 | *Coffea canephora* | CSPFGKPCRYNPWGCCDSCVCVATPADEGRCLGNC |
| 21 | *Daucus carota* | CLPNGGFCMFRPMDCCGSCGCLYPVGVCFGTGC |
| 22 | *Daucus carota* | CYPKGHECRTDPTLCCHNCGCIMPVGVCFGINC |
| 23 | *Eragrostis curvula* | CLPSGGFCMFRPKDCCGSCGCLYPIGVCFGSSC |
| 24 | *Eleusine coracana* | CIPMGGFCLFNLRGCCGSCGCLAGFCWRDASSCDL |
| 25 | *Eleusine coracana* | CIPMGGFCLGNLRGCCGSCGCLAGFCWRPASSCDS |
| 26 | *Elymus wawawaiensis* | CLPSGGFCMFRPKDCCGNCGCLYPIGVCYGSRCEE |
| 27 | *Gossypium hirsutum* | CKPKGSFCLFDLQSCCRPCGCLAGWCYNIDHDCNEYT |

TABLE 2-continued

Amino acid sequence of preferred ginsentide-like peptides

| SEQ ID | Source | Amino acid sequence |
|---|---|---|
| 28 | Griselinia littoralis | CISSGGFCMFNPRDCCGSCGCLYPMGICYGSSC |
| 29 | Gossypium raimondii | CKPIGSFCLFDLTSCCRPCGCLAGFCYNLDHNCNEYT |
| 30 | Gossypium raimondii | CKPKGSFCLFDLTSCCRPCGCLAGWCYNYDHECNEYT |
| 31 | Gossypium raimondii | CIAKGGFCLFDLTSCCRPCGCLAGWCYNIDHDCKEYT |
| 32 | Gossypium raimondii | CIAKGGFCLFDLTSCCRPCGCLAGWCYNIDHDCNEYA |
| 33 | Gossypium raimondii | CIAKGGFCLFDLTSCCRPCGCLAGWCYNIDHDCNEYT |
| 34 | Hibiscus cannabinus | CIPKGGWCLFDIMGCCKPCGCLAGFCWVVGDDCN |
| 35 | Hibbertia grossulariifolia | CSPLGGKCGDLVECCSGCVCIWPTYTCVGHC |
| 36 | Hedera helix | CQPFDAPCDTFYGFYCCGSCTCTYVDFWHTSRCTGSC |
| 37 | Heracleum lanatum | CLPAGGFCMFRPMDCCGTCGCLYPVGVCFGNDC |
| 38 | Lennoa madreporoides | CIGAGGFCMFNPMDCCGNCGCLYPVGICFGTGC |
| 39 | Microtea madreporoides | CLNGGGYCGSFTREACCYNCVCMMAFCVCG |
| 40 | Mollugo nudicaulis | CKSAGEWCGFSWTDCCNSCGCLAGFCYGTSC |
| 41 | Myodocarpus sp. | CIPKGGFCLFDLRGCCGMCGCLAGVCFNYDHPCEE |
| 42 | Menyanthes trifoliata | CLSSGGFCMFRPNDCCGNCGCLYPVGICYGTGC |
| 43 | Oryza sativa | CLPAGGFCMFRPMDCCGNCGCLYPVGVCYGSRCEE |
| 44 | Pholisma arenarium | CLPAGGFCMFRPMDCCGNCGCLYPVGVCYGSRCEE |
| 45 | Pholisma arenarium | CISAGGFCFFDPMNCCGNCGCLYPVGICVGTNC |
| 46 | Polyscias fruticosa | CSPLGGKCGDLVECCSGCVCIWPTYTCVGHC |
| 47 | Polyscias fruticosa | CIPLGGDCTDLFDCCPGCVCIITDLTCDGNCFRGA |
| 48 | Polyscias fruticosa | CLTLGLYCGGGSGECCSGCLCVYPTLTCRGNCYRGA |
| 49 | Phyllanthus sp. | CSDPGGYCVPFFQGCCNDCSCLDLGVVAGVCVCI |
| 50 | Populus trichocarpa | CISSGGWCFTQPKNCCGNCGCLYPIGICFGSDC |
| 51 | Populus trichocarpa | CISSGGWCFPNPKNCCGNCGCLYPIGICFGSDC |
| 52 | Populus tremula | CISSGGFCFTQPMNCCGNCGCLYPLGICYGSDC |
| 53 | Salix dasyclados | CLPSGGFCMFQPMNCCGNCGCLYPIGVCYGSNC |
| 54 | Theobroma cacao | CLSAGGFCMFNPMDCCGNCGCLYPMGICYGSGC |
| 55 | Theobroma cacao | CLSAGGFCMFNPMDCCGNCGCLFPMGICYGSGC |
| 56 | Theobroma cacao | CLSAGGFCMFNPMDCCGNCGCLYPMGFCYGSGC |
| 57 | Theobroma cacao | CLSAGGFCMFNPMDCCGNCGCLYPLGFCYGSGC |
| 58 | Theobroma cacao | CLSAGGFCMFDPMDCCGNCGCLYPMGICYGSGC |
| 59 | Theobroma cacao | CLSAGGFCMFIPMDCCGNCGCLFLMGFCYGSGC |
| 60 | Theobroma cacao | CLSAGGFCMFIPMDCCGNCGCLFPMGFCYGSGC |
| 61 | Theobroma cacao | CLSAGGFCMFNPMDCCGNCGCLYPMGICYGSGC |
| 62 | Theobroma cacao | CPSAGGFCMFNPMDCCGNCGCLYPMGICYGSGC |
| 63 | Theobroma cacao | CLSAGGFCMFNPMDCCGNCGCLYPLGICYGSGC |
| 64 | Triticum aestivum | CLPAGGFCMFRPMDCCGNCGCLYPAGVCYGTRCEE |

Solid-phase peptide synthesis or 'SPPS' refers to the direct chemical synthesis of peptides, wherein an insoluble support is used as an anchor for the growing peptide chain, which is typically built up one amino acid at a time. The free N-terminal amine of a solid-phase attached peptide is coupled to an N-protected amino acid unit. This unit is then deprotected, revealing a new N-terminal amine to which a further amino acid unit may be attached. The general principle of SPPS is one of repeated cycles of such coupling-wash-deprotection-wash steps, adding, typically one amino acid at a time, until the peptide of the desired sequence and length has been synthesized. As will be understood by those skilled in the art it is possible, in principle, to couple N-protected peptides instead of single amino acids to the growing chain in one or more elongation cycles. The present invention also encompasses methods wherein one or more larger N-protected peptides, or oligopeptides, typically having a length of up to 20 amino acid, preferably up to 10 amino acids, more preferably up to 5 amino acids, still more preferably up to 4 amino acids are added to the growing chain. In a particularly preferred embodiment, a method as defined herein is provided, wherein step a) comprises stepwise coupling amino acids, dipeptides and/or tripeptides, preferably amino acids and/or dipeptides to the growing peptide chain. In a most preferred embodiment of the invention, step a) comprises stepwise coupling of single amino acids or building blocks (e.g. amino acid pairs) to the growing peptide chain.

Preferably, in accordance with the present invention, the growing peptide is anchored to the resin through the terminal carboxyl group. Nevertheless, the use of certain linkers allowing for anchoring of the growing peptide-chain via a side-chain residue, is also envisaged and may even be preferred.

The solid support for SPPS typically is a solid, non-soluble support material. For the purposes of the present invention, such a solid support comprises sites for anchoring of a first amino acid (or peptide). Such functional sites for anchoring of the peptide are termed linkers. If needed, other linker moieties such as e.g. more specialized, for instance more acid-labile, linkers may be grafted to the first, integral linkers on the premade solid support, which is often then referred to as a 'handle'. Polymeric organic resin supports are the most common type of solid support material, typically comprising highly solvated polymers with an equal distribution of functional groups. Examples include Polystyrene (PS); Polyacrylamide (PA); polyethylene glycol (PEG); PEG-Polystyrene (PEG-PS) or PEG-Polyacrylamide (PEG-PA); and other PEG-based supports. The invention is not particularly limited with respect to the solid support material. The 2-chlorotritylchloride resin, Wang resin (4-Benzyloxybenzyl Alcohol resin) and PAM resin (4-hydroxymethyl-phenylacetamidomethyl), are particularly suitable solid support materials for methods of the present invention. Other suitable examples include, but are not limited to: PEG-HMPB (cross-linked PEG functionalized with 4-(4-Hydroxymethyl-3-methoxyphenoxy)butyric acid); Rink amide resin (4-(2',4'-Dimethoxyphenyl-Fmoc-aminomethyl-phenoxy-resin); and Merrifield resin (copolymer of styrene and chloromethylstyrene cross-linked with divinylbenzene). Solid support materials should meet several requirements, besides being chemically inert and able to withstand the conditions of synthesis: solid support particles are preferably of conventional and uniform size, mechanically robust, easily filterable and highly accessible to the solvents allowing the penetration of the reagents and the enlargement of the peptide chain within its microstructure. Resins as used in the present invention are typically of standard mesh size, which is about 50-500 mesh, more preferably 100 to 400 mesh.

As stated above, the present method concerns so-called 'Fmoc SPPS' methods, wherein Fmoc (Fluorenylmethyl-oxycarbonyl) N-protected amino acids and peptides are added to the growing chain. Fmoc protection in solid support peptide synthesis has significant advantages because its removal involves very mild basic conditions (e.g. piperidine solution), such that it does not disturb the acid labile linker between the peptide and the resin. Fmoc N-protected amino acids are commercially available. Furthermore, reactions to produce Fmoc N-protected amino acids or peptides are common general knowledge for those skilled in the art.

Each incoming amino acid that is added to the growing peptide chain is preferably also protected, where suitable, with a side-chain protecting group, which is typically acid-labile. Protection groups suitable for this purpose are well known in the art. Commonly employed carboxy-protection groups for Glutamine and Aspartic acid are e.g. Mpe, O-1-Adamantyl, O-benzyl and even simply alkyl esters may be used, though less common. For the sake of ease, typically and preferably tert-butyl groups are used. Tyrosine may typically be protected by protection groups such as tert-butyl ether or Z- or more preferably 2-Bromo-Z-esters. It is equally possible to use tritylalkohol protection groups such as 2-chloro-trityl or 4-methoxy or 4,4' methoxy-trityl groups. Preferably, a trityl or a tert-butyl (tBu) protection group is used, most preferably a tBu protection group, meaning the tyrosyl side chain is modified to a tertiary-butyl ether. The tBu group is only efficiently removed under strongly acidic condition. Suitable Arginine protective groups include 2,2,4,6,7-pentamethyldihydrobenzofuranyl-5-sulfonyl (Pbf), adamantyloxy-carbonyl and isobornyl-oxy-carbonyl, 2,2,5,7,8-pentamethylenchromanesulfonyl-6-sulfonyl (Pmc), 4-methoxy-2,3,6-trimethylbenzenesulfonyl (Mtr) and its 4-tert.butyl-2,3,5,6-tetramethyl homologue (Tart) or Boc, which are only cleaved under strongly acidic conditions. Preferably, Pbf, Pmc, Mtr, most preferably Pbf is used. Upon global deprotection of side chains under strongly acidic conditions, in usually aqueous medium, bystander-alkylation of deprotected tyrosine is not observed with Pmc, Mtr and Pbf. Serine and, Threonine typically may be protected by e.g. tert-butyl or trityl, most preferably tert-butyl. Other modes of protection are equally feasible, e.g. with benzyl, though less preferred since eventually requiring removal under less desirable condition. Similar considerations apply to protection of Lysine; typically and preferably, Lys is protected with Boc. Tryptophan must not necessarily be protected during solid-phase synthesis, though protection with typically Boc is evisaged. As regards side chain protection groups, the aforementioned is valid both for the natural L-amino acids as well as for their D-homologues.

Therefore, in various embodiments, step (a) comprises the steps of:
(i) deprotecting a first amino acid linked to the solid support by removing protective chemical groups from the first amino acid;
(ii) activating chemical groups on a second amino acid to prepare the second amino acid for coupling with the first amino acid;
(iii) coupling the activated second amino acid to the deprotected first amino acid to form a peptide from the first and second amino acids; and (iv) successively deprotecting, and coupling a plurality of amino acids into the growing peptide chain until the ginsentide or ginsentide-like peptide is synthesized.

The abundance of glycine and cysteine residues in the ginsentide sequence usually poses synthetic challenges in the chemical synthesis thereof, especially in the C-terminus. Attempts to synthesize ginsentides by stepwise synthesis using solid-phase methods have failed because the C-terminal fragments formed aggregates, preventing a successful synthesis. The method described herein addresses these challenges. In particular, a strategically selected glycine residue, i.e. the one at the position corresponding to position 24 of SEQ ID NO:1, is alkylated by a reversible protecting group to prevent aggregation during the synthesis. Fmoc-(Dmb)Gly-OH is used for the addition of the glycine residue at this position, while Fmoc-Gly-OH may be used for the introduction of glycine residues at other positions.

Coupling reagents for Fmoc peptide synthesis are well-known in the art. Coupling reagents may be mixed anhydrides, (e.g. propane phosphonic acid anhydride) or other acylating agents such as activated esters or acid halogenides (e.g. isobutyl-chloroformiate or 'ICBF'), or they may be carbodiimides (e.g. 1-ethyl-3-(3-dimethylaminopropyl)-carbodiimide, diisopropyl-carbodiimide, dicyclohexyl-carbodiimide), activated benzotriazine-derivatives (e.g. 3-(diethoxyphosphoryloxy)-1,2,3-benzotriazine-4(3H)-one or 'DEPBT') or uronium or phosphonium salt derivatives of benzotriazol. In view of best yield, short reaction time and protection against racemization during chain elongation, it is preferred that the coupling reagent is selected from the group consisting of uronium salts and phosphonium salts of benzotriazol capable of activating a free carboxylic acid function along with that the reaction is carried out in the presence of a base. Suitable and likewise preferred examples of such uronium or phosphonium coupling salts are e.g. HBTU (O-1H-benzotriazole-1-yl)-N,N,N',N'-tetramethyl uronium hexafluorophosphate), BOP (benzotriazole-1-yl-oxy-tris-(dimethylamino)-phosphonium hexafluorophosphate), PyBOP (Benzotriazole-1-yl-oxy-tripyrrolidinophosphonium hexafluorophosphate), PyAOP, HCTU (O-(1H-6-chloro-benzotriazole-1-yl)-1,1,3,3-tetramethyluronium hexafluorophosphate), TCTU (O-1H-6-chloro benzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N'-tetramethyluronium tetrafluoroborate), HAPyU (O-(benzotriazol-1-yl)oxybis-(pyrrolidino)-uronium hexafluorophosphate.

For coupling of the Fmoc amino acids to the peptide, the carboxyl group is usually activated. This is important for speeding up the reaction. There are two main types of activating groups: carbodiimides and triazolols. The use of these activating coupling additives is particularly preferred when using the highly activating uronium or phosphonium salt coupling reagents. Most preferably the coupling additive is a N-hydroxy-benzotriazol derivative (or 1-hydroxy-benzotriazol derivative) or is an N-hydroxy-benzotriazine derivative. Suitable examples include N-hydroxy-succinimide, N-hydroxy-3,4-dihydro-4-oxo-1,2,3-benzotriazine (HOOBt), 1-hydroxy-7-azabenzotriazole (HOAt) and N-hydroxy-benzotriazole (HOBt). N-hydroxy-benzotriazine derivatives are particularly preferred, in a most preferred embodiment, the coupling reagent additive is hydroxy-3,4-dihydro-4-oxo-1,2,3-benzotriazine. Most common carbodiimides are dicyclohexylcarbodiimide (DCC) and diisopropylcarbodiimide (DIC).

Activation of the Fmoc amino acid is typically done in the presence of a base reagent. Preferably, the base reagent is a weak base whose conjugated acid has a pKa value of from pKa 7.5 to 15, more preferably of from pKa 7.5 to 10, and which base preferably is a tertiary, sterically hindered amine. Examples of such and further preferred are Hunig-base (N,N-diisopropylethylamine; DIPEA), N,N'-dialkylaniline, 2,4,6-trialkylpyridine, 2,6-trialkylpyridine or N-alkyl-morpholine with the alkyl being straight or branched $C_1$-$C_4$ alkyl, more preferably it is N-methylmorpholine (NMM) or collidine (2,4,6-trimethylpyridine), most preferably it is collidine.

The amount of the various reactants in the coupling reaction can and will vary greatly. Reagents are typically used in large excess to speed-up the reaction and drive it to completion. Typically the amount of solid support to the amount of Fmoc-amino acid will be a molar ratio ranging from about 1:1 to 1:10. In one embodiment, the amount of solid support to the amount of Fmoc-amino acid to the amount of activating compound is a molar ratio of about 1:4. The reaction conditions for the coupling steps, such as reaction time, temperature, and pH may vary without departing from the scope of the invention. The coupling temperature is usually in the range of from 15 to 30° C., especially where using phosphonium or uronium type coupling reagents. Typically, a temperature of about 20 to 25° C. is applied for coupling.

In various embodiments, the method comprises accelerating at least one of the deprotecting, activating, and coupling steps by applying microwave energy.

Microwave energy applied to the contents of the reaction vessel during the deprotecting, activating, coupling, and cleaving steps greatly decreases the length of time necessary to complete these reactions. The method for applying microwave energy may be moderated by the microwave source in such a way as to provide the fastest reaction time while accumulating the least amount of heat, thus more microwave energy may be applied and heat-associated degradation of the reaction contents does not occur. This method may include, but not limited to, spiking the microwave energy in large amounts for short lengths of time.

The method may include cooling the reaction vessel and thus its contents, during and between applications of microwave energy up to and including the final cleaving step. The cooling mechanism of the method operates during amino acid extension cycles, the term "cycle" used herein to refer to the deprotection, activation, and coupling necessary to link one amino acid to another. The cooling system can also operate during and between applications of microwave energy in a given cycle to keep the bulk temperature of the reaction contents down. The cooling system can also operate when the complete peptide is cleaved from the resin. Alternatively, by controlling the power rather than strictly controlling the temperature, a desired control over the progress of a reaction can also be provided.

It should be noted that the amino acid sequence of any one of SEQ ID NOs:1-64 as described above only defines the primary structure of the ginsentide or ginsentide-like peptide, i.e. the sequence of amino acids, without including any information about the disulfide bridges (—S—S—) that may be existing in the peptide.

Disulfide bridges are produced by the oxidative folding of two different thiol groups (—SH) present in the peptide. The peptide described herein contains eight different thiol groups (i.e. eight cysteine residues each containing a thiol group) and therefore may form zero, one, two, three, or four intramolecular disulfide bridges. The number of possible disulfide bridge connectivity patterns (cysteine pairings) increases rapidly with the number of bound cysteines.

To form native intracellular disulfide bonds, the synthesis process described herein is followed by oxidative folding of the synthesized peptide. The oxidative folding of a peptide or a protein refers to the concurrent formation of one or more native disulfide bonds of its reduced form to an oxidized folded form with identical disulfide connectivity with the native molecule. Disulfides in a peptide or and protein stabilizes its structure and maintains its biological activities. Many bioactive peptides are cysteine-rich, containing 2-5 disulfide bonds. However, the oxidative folding or refolding of synthetic or recombinant peptides or proteins, particularly those that are cysteine-rich, is invariably performed in an aqueous buffered solution and in the presence of a pair of reducing and oxidizing reagents to facilitate the correct disulfide bond formation by disulfide-exchange reactions. However, oxidative folding in an aqueous solution is a limiting step in their preparation because of unpredictability of generating isomeric and dead-end products. Chemoselective disulfide approaches which selectively form each disulfide pair stepwise can achieve correct pairing disulfide bonds, but the process is laborious and generally suffers from low yields. Approaches of oxidative folding for cysteine-rich peptides include air oxidation, the use of strong oxidizing agents or reduced/oxidized glutathiones and invariably in aqueous media at a basic pH, which may be referred to as aqueous oxidative folding. In this invention, an ultra-fast oxidative folding of peptides in non-aqueous conditions and performed in organic solvents (organic oxidative folding) has been achieved. Compared to the aqueous oxidative folding, the organic oxidative folding is remarkably faster.

In various embodiments, organic oxidative folding comprises folding the ginsentide or ginsentide-like peptide in an organic solvent (preferably DMSO and/or isopropanol) comprising cysteamine and/or morpholine, e.g. in a folding buffer comprising 10% (v/v) DMSO, 84.36% (v/v) isopropanol, 5% (v/v) morpholine and 0.64% (v/v) Cysteamine (10M).

In various embodiments, the organic oxidative folding is performed at 4° C.

It is believed that the method of organic oxidative folding described herein enables the formation of native disulfide bonds of cysteine-rich peptides within minutes, e.g. within 1, 2, 3, 4, 5, 6, 7, 8, 9, 10, 15, 20, 25, 30, 35, 40, 45, 50, 55, or 59 minutes, preferably within 5 minutes, which is remarkably faster than conventional methods known in the art such as aqueous oxidative folding.

In various embodiments, the method comprises purifying the folded ginsentide or ginsentide-like peptide or salt thereof, preferably by RP-HPLC.

Without wishing to be bound to any particular theory, it is believed that the ginsentide or ginsentide-like peptide prepared by the method described herein have four native disulfide bonds as described in Table 1. The prepared ginsentide or ginsentide-like peptide is identical to the natural peptide and is functionally indistinguishable therefrom.

It should be noted that the methods of solid-phase peptide synthesis and organic oxidative folding described herein can also be used in the preparation of other cysteine-rich peptides. Such uses are also within the scope of the present application.

In a second aspect, the invention relates to a method of recombinantly preparing a ginsentide or ginsentide-like peptide or a pharmaceutically acceptable salt thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, wherein the method comprises the steps of:

(a) providing a host cell comprising a polynucleotide, wherein the polynucleotide encodes a polypeptide comprising Maltose-binding protein having the amino acid sequence set forth in SEQ ID NO:65, a enterokinase cleavage sequence having the amino acid sequence set forth in SEQ ID NO:66, and the ginsentide or ginsentide-like peptide or salt thereof;

(b) culturing the host cell in a growth medium under conditions allowing production of the polypeptide, and recovering the polypeptide from the medium; and (c) generating the ginsentide or ginsentide-like peptide or salt thereof by cleaving the polypeptide using enterokinase.

The polypeptide may be recombinantly expressed in a host cell or a cell-free system. The polypeptide may be produced using any known and well-established expression system and recombinant cell culturing technology. The polypeptide may also be produced in a host cell in a transgenic organism such as a goat or a plant.

The term "host cell" for the purposes of the present invention refers to any cell that is commonly used for expression, i.e. transcription and translation of the polynucleotides for the production of the polypeptides of interest. In particular, the term "host cell" relates to prokaryotes, lower eukaryotes, plants, insect cells or mammalian cell culture systems. Host cells include, without limitation, bacterial, microbial, plant or animal cells, e.g. *Escherichia coli, Bacillus subtilis; Saccharomyces cerevisiae, Pichia pastoris,* or CHO cells.

For recombinant production of the polypeptide typically a polynucleotide encoding the polypeptide is isolated and inserted into a replicable vector such as a plasmid for further cloning (amplification) or expression. In various embodiments a polynucleotide encoding a polypeptide according to the invention is included in a vector such as a plasmid. The term "vector" as used herein refers to a polynucleotide capable of transporting another nucleic acid to which it has been linked. In one embodiment, the vector is a "plasmid," which refers to a circular double stranded DNA loop into which additional DNA segments may be ligated. In another embodiment, the vector is a viral vector, wherein additional DNA segments may be ligated into the viral genome. The vectors disclosed herein can be capable of autonomous replication in a host cell into which they are introduced (e.g., bacterial vectors having a bacterial origin of replication and episomal mammalian vectors) or can be can be integrated into the genome of a host cell upon introduction into the host cell, and thereby are replicated along with the host genome (e.g., non-episomal mammalian vectors).

When using recombinant techniques, the polypeptide can be produced intracellularly, in the periplasmic space, or directly secreted into the medium. If the polypeptide is produced intracellularly, as a first step, the particulate debris, either host cells or lysed fragments, are removed, for example, by centrifugation or ultrafiltration. Carter et al., Bio/Technology 1992; 10: 163-167 describe a procedure for isolating polypeptides which are secreted to the periplasmic space of *E coli*. The polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. *J Mol Biol* 2002; 315, 1-8).

In various embodiments, the polypeptide has the amino acid sequence set forth in any one of SEQ ID NOs: 67-130.

TABLE 3

Amino acid sequences of SEQ ID NOs: 65-80

| Name | SEQ ID NO | Sequence |
|---|---|---|
| Maltose-binding protein | 65 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDANAGKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LG |
| enterokinase cleavage sequence | 66 | DDDDK |
| Maltose-binding protein-enterokinase cleavage sequence-TP1 | 67 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCKSSGAWCGFDPHGCCGNCGCL VGFCYGTGC |
| Maltose-binding protein-enterokinase cleavage sequence-TP2 | 68 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCKSSGAWCGFDPHGCCGNCGCL VGFCYGTGC |
| Maltose-binding protein-enterokinase cleavage sequence-TP3 | 69 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCKSAGTWCGFDPHGCCGSCGCL VGFCYGVSC |
| Maltose-binding protein-enterokinase cleavage sequence-TP4 | 70 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCLKNGEFCWGDPSGCCGNCGCL IIPGVCYGTGC |
| Maltose-binding protein-enterokinase cleavage sequence-TP5 | 71 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCKSSGAWCGFDPHGCCGNCGCL VGFCYGTDC |
| Maltose-binding protein-enterokinase cleavage sequence-TP6 | 72 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCIPGGGFCMFEPLSCCVNCGCI LVPGVCYCG |
| Maltose-binding protein-enterokinase cleavage sequence-TP7 | 73 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN |

TABLE 3-continued

Amino acid sequences of SEQ ID NOs: 65-80

| Name | SEQ ID NO | Sequence |
|---|---|---|
| | | LGDDDDKCKSGGTWCGFDPHGCCGNCGCL VGFCYGTGC |
| Maltose-binding protein-enterokinase cleavage sequence-TP8 | 74 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCISSGGWCGFDLHGCCGNCGCL VGFCYGTGC |
| Maltose-binding protein-enterokinase cleavage sequence-TP9 | 75 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCKSGGSWCGFDPHGCCGNCGCL VGFCYGTGC |
| Maltose-binding protein-enterokinase cleavage sequence-TP10 | 76 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCIFSGGWCGFDLHGCCGNCGCL VGFCYGTGC |
| Maltose-binding protein-enterokinase cleavage sequence-TP11 | 77 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCLKNGQFCWGNPSGCCGNCGCL IIPGVCYGTGC |
| Maltose-binding protein-enterokinase cleavage sequence-TP12 | 78 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCIPGGGFCMFEPLSCCHNCGCL LVPGVCYCG |
| Maltose-binding protein-enterokinase cleavage sequence-TP13 | 79 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCIPNGGFCMFEPLSCCVNCGCI LVPGVCYCG |
| Maltose-binding protein-enterokinase cleavage sequence-TP14 | 80 | MKIKTGARILALSALTTMMFSASALAKIE EGKLVIWINGDKGYNGLAEVGKKFEKDTG IKVTVEHPDKLEEKFPQVAATGDGPDIIF WAHDRFGGYAQSGLLAEITPDKAFQDKLY PFTWDAVRYNGKLIAYPIAVEALSLIYNK DLLPNPPKTWEEIPALDKELKAKGKSALM FNLQEPYFTWPLIAADGGYAFKYENGKYD IKDVGVDNAGAKAGLTFLVDLIKNKHMNA DTDYSIAEAAFNKGETAMTINGPWAWSNI DTSKVNYGVTVLPTFKGQPSKPFVGVLSA GINAASPNKELAKEFLENYLLTDEGLEAV NKDKPLGAVALKSYEEELVKDPRIAATME NAQKGEIMPNIPQMSAFWYAVRTAVINAA SGRQTVDEALKDAQTNSSSNNNNNNNNNN LGDDDDKCLKVGKICLGRGLKECCPSATC GCLLGFCIKC |

The recombinantly produced polypeptide is further cleaved by enterokinase immediately after the C-terminal ends of the enterokinase cleavage site (Asp-Asp-Asp-Asp-Lys, SEQ ID NO:66) such that the ginsentide or ginsentide-like peptide is released for further purification.

In various embodiments, the method further comprises purification of the recombinantly produced polypeptide prior to the enterokinase cleavage, preferably by amylose resin purification.

The polypeptide produced by the cells can be purified using any conventional purification technology, for example, by gel electrophoresis, dialysis, affinity chromatography, or preferably by anion-exchange chromatography and/or reverse-phase chromatography. The choice of the purification method that is used for a particular polypeptide of the invention is within the knowledge of the person of average skill in the art.

Without wishing to be bound to any particular theory, ginsentide or ginsentide-like peptides recombinantly produced using the method described herein have native disulfide bonds making organic oxidative folding of the ginsentide or ginsentide-like peptides unnecessary.

Due to their high sequence similarity, it is believed that the ginsentides or ginsentide-like peptides described herein have similar biological functions.

In addition, it should be understood that a polypeptide comprising, consisting essentially of, or consisting of a ginsentide or ginsentide-like peptide of the invention may also be prepared using the methods detailed above. It may also be used in the applications described below. Such methods of preparation and uses of these polypeptides are also within the scope of the present application. The ginsentide or ginsentide-like peptides and the polypeptides described herein are preferably substantially free of impurities, but may still contain extraneous compounds or impurities that can come from many sources, such as unreacted starting materials, by-products, degradation products, and residual components of host cells.

It should also be understood that enriched fractions obtained by chromatographic, size-exclusion, or methods related to purification to enrich peptides with MW between 2-5 kDa from ginseng plants or plants containing ginsentide-related compounds from natural sources, as well as their use in the nutraceutical, pharmaceutical or cosmetic applications described below are also within the scope of the present application.

In a third aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as an α1-adrenergic receptor antagonist and vasorelaxant.

In a fourth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as a nitric oxide-boosting agent.

In a fifth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as an anti-thrombotic agent.

In a sixth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as an anti-atherosclerotic agent.

In a seventh aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as a protective agent against doxorubicin-induced cardiotoxicity.

In an eighth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as an anti-ageing and adaptogenic agent.

In a ninth aspect, the invention relates to use of a ginsentide or ginsentide-like peptide or a pharmaceutically acceptable salt thereof or enriched fractions by chromatographic, size-exclusion, or methods related to purification from ginseng plants or plants containing ginsentides or ginsentide-like peptides thereof, said ginsentide or ginsentide-like peptide having (i) the amino acid sequence set forth in any one of SEQ ID NO:1-64; or (ii) the amino acid sequence sharing at least 65%, preferably at least 75%, even more preferably at least 85%, most preferably at least 95% sequence identity with the peptide of (i) over its entire sequence, as a nutraceutical, a health supplement, or a cosmetic ingredient.

The term "nutraceutical" as used herein refers to a substance intended to supplement a diet and provide nutrients, such as, for example, vitamins, minerals, fiber, fatty acids, or amino acids, that may be missing or may not be consumed in sufficient quantity in the diet. The term "health supplement" as used herein includes food and food supplement to animals and/or humans, fortification of food, dietary supplement, functional (and medical) food and nutrient supplement. The term "cosmetic ingredient" as used herein refers to any agent that may be comprised in a cosmetic formulation for cosmetic use, such as skin conditioning agents and anti-aging agents.

In various embodiments of the afore-described third to ninth aspects of the invention, the ginsentide or ginsentide-like peptide or salt thereof, regardless of whether it is commercially obtained, isolated from natural sources, or preferably synthetically or recombinantly prepared by a method described herein, can be used in vitro as a biologically active agent. In various embodiments, it can be administered to a subject (e.g. a human or an animal) in need thereof in an effective amount for the treatment or prevention of a condition, disease or disorder considered suitable, alone or in combination (simultaneously, sequentially or separately) with one or more other agents. Such conditions, diseases or disorders include, without limitation, hypertension, ischaemic heart disease, thrombosis, atherosclerosis, erectile dysfunction, stroke, myocardial infarction, heart failure, cancer, aging and aging-related diseases.

Accordingly, the ginsentide or ginsentide-like peptide or salt thereof can be formulated into compositions further comprising a pharmaceutically acceptable carrier. The term "pharmaceutically acceptable carrier" as used herein means a pharmaceutically acceptable material, composition or vehicle, such as a liquid or solid filler, diluent, excipient, or solvent encapsulating material, involved in carrying or transporting the peptide from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; sterile distilled water; pyrogen-free water; isotonic saline; Ringer's solution; ethyl alcohol; pH buffered solutions; polyesters, polycarbonates or polyanhydrides; and other non-toxic compatible substances employed in pharmaceutical formulations. See Remington: The Science and Practice of Pharmacy, 19th Ed. (Easton, Pa.: Mack Publishing Co., 1995), which discloses typical carriers and conventional methods of preparing pharmaceutical formulations.

The skilled artisan would also realize that proper formulation is dependent upon the route of administration selected for the specific application, and the proper route and mode of administering the peptide of the invention to a subject should be determined on a case-by-case basis.

The composition of the invention can be administered via any parenteral or non-parenteral (enteral) route that is therapeutically effective for proteinaceous or nucleic acid-based drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instillation is given by Patton et al. *Proc Amer Thoracic Soc* 2004; Vol. 1 pages 338-344, for example). Non-parenteral delivery modes are, for instance, orally, e.g. in the form of pills, tablets, capsules, solutions or suspensions, or rectally, e.g. in the form of suppositories. Peptides of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders.

The dosage of the peptide of the invention applied may vary within wide limits to achieve the desired preventive effect or therapeutic response. It will, for instance, depend on the half-life of the peptide in vivo. Further, the optimal dosage will depend on the biodistribution of the peptide, the mode of administration, the severity of the disease/disorder being treated as well as the medical condition of the patient. If wanted, the peptide may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the peptide of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

In some embodiments, the ginsentide or ginsentide-like peptide or salt thereof can be comprised in any cosmetic compositions known in the art to provide for topical skin rejuvenation and/or anti-aging compositions.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

The compositions and the methods of therapeutic or cosmetic applications of the ginsentide or ginsentide-like peptides and compositions described above are also within the scope of the present application.

The present invention is further illustrated by the following examples. However, it should be understood, that the invention is not limited to the exemplified embodiments.

EXAMPLES

Materials and Methods
General Procedures for Peptide Solid Phase Synthesis by Fmoc-Chemistry For peptide-hydrazides, firstly, the 2-chlorotritylchloride resin was swelled in dry DCM for a while, 5% hydrazine in dry DMF was directly added. After 0.5 hr, the resin was washed with DCM (3×), DMF (3×), and DCM (3×). Peptides were then assembled on the hydrazine-trityl resin using typical Fmoc SPPS protocols. All amino acids were used in 4 eq of the resin, and preactivated by 4 eq of PyBop and 8 eq of DIEA. After 1 to 2 hr coupling of amino acid, the resin was washed with DCM (3×), DMF (3×), and DCM (3×). The successive α-amino group deprotection was performed in 20% piperidine in DMF (5 min, 10 min) between each amino acid coupling step. Finally, a peptide-hydrazide was released from resin by using the cleavage reagent: a mixture of 90% TFA, 5% EDT, 2.5% TIS and 2.5% water. After precipitated from ether, the crude peptide-hydrazide was purified by prep-HPLC, the molecular weight was determined by ESI-MS.

For cysteinyl peptides, firstly, 2 eq of Fmoc-Cys(Trt)-OH was dissolved in dry DCM (with a small amount of dry DMF for solubility), and added into the swelled 2-chlorotrityl-chloride resin with 5 eq (respective to the amino acid) of DIEA. After 1 hr reaction, the resin was washed with DCM (3×), DMF (3×), and DCM (3×). For capping any remaining reactive trityl groups, the resin was reacted with methanol for 15 min. Once the cysteine residue was attached on the resin, amino acid coupling, α-amino group deprotection and final peptide cleavage were performed according to the same procedure described in the above.

Microwave-Assisted Automated Peptide Synthesis

Microwave-assisted peptide synthesis was performed in 0.1 mmol and 0.25 mmol on CEM microwave peptide synthesizer, liberty 1 according to the manual instruction. Fmoc-(Dmb) Gly-OH was used in peptide C-terminal part instead of Fmoc-Gly-OH. Fmoc deprotection was done in 20% piperidine/DMF containing 0.1 M HOBt. Coupling of Fmoc/tBu-protected amino acids were achieved by 5 eq amino acids activated by PyBop in DMF. The parameters used in the microwave synthesis was shown in the below table.

TABLE 6

MW-SPPS parameters used in the synthesis (CEM microwave peptide synthesizer, liberty 1)

| Amino acid | Number of couplings | Power (W) | Temp (° C.) | Time (s) |
|---|---|---|---|---|
| Coupling | | | | |
| Asn | 2 | 20 | 50 | 600 |
| Asp | 2 | 20 | 50 | 600 |
| Cys | 2 | 20 | 50 | 600 |
| Pro | 2 | 20 | 50 | 600 |
| AA followed by Pro | 1 | 20 | 50 | 600 |
| Other AAs | | | | |
| Deprotection | | | | |
| Initial depro | 1 | 20 | 55 | 30 |
| depro | 1 | 20 | 55 | 180 |

After the completion of peptide synthesis, the peptide was cleaved in a mixture of 90% TFA, 5% EDT, 2.5% TIS and 2.5% water. And then, the peptide precipitated by ether was directly used in the folding reaction.

Ligation of Peptide-Hydrazide with Cysteinyl Peptide

Briefly, a Fmoc-peptide hydrazide was first oxidized to form peptide azide by sodium nitrite (5 eq of peptide) at pH 3.0 in 0.2 M phosphate buffer, pH 3.0, containing 6 M Gdn-HCl, at −20 degree for 20 min. After addition of sodium 2-mercaptoethanesulfonate (MESNa) (final conc. 1%), and adjustment of pH to 7.0, the peptide thioester was then formed. Finally, this peptide thioester reacted chemoselectively with Cysteinyl-peptide to produce the full-length peptide by generating a native amide bond at the ligation site. The removal of Fmoc from the ligated full-length peptide was done in 20% piperidine with TCEP for 20 min.

Folding of Reduced Peptides to Native Form

For most ginsentides and cysteine-rich peptides, the folding was performed in 20% DMSO in 0.1 M $(NH_4)HCO_3$ containing cysteamine/cystamine. The ratio of peptide:cysteamine:cystamine was around 1:200:10. 10% TFE, 5% or 10% IPA may be included depending on peptides' solubility. Peptides were dissolved in very small amount of DMSO, and then, added into the folding buffer, folded at 4 degree, overnight. After folding, the reaction was buffer-exchanged and concentrated by using Sek-Pak C18 cartridge. The concentrated folding mixture was purified by using HPLC to get pure folded products.

For organic oxidative folding, peptides were dissolved in very small amount of DMSO, added into the folding buffer comprising 10% (v/v) DMSO, 84.36% (v/v) isopropanol, 5% (v/v) morpholine and 0.64% (v/v) Cysteamine (10M), and was folded at 4° C. for 5 min. After folding, the reaction was buffer-exchanged and concentrated by using Sek-Pak C18 cartridge. The concentrated folding mixture was purified by using HPLC to get pure folded products.

Recombinant Expression of Ginsentides

Overall Strategies for the Recombinant Expression of Ginsentides

1. Targeted sequence was cloned into a vector, where the ginsentide was fused to the C-terminal of periplasmic signal sequence-maltose binding protein (MBP) with a DDDK cleavable sequence in between (enterokinase can cleave at the C-terminal of DDDK);

2. Plasmid was transformed into *E. coli* and selected using ampicillin-containing agar plates;

3. A single colony was picked and cultured in liters of ampicillin-containing LB broth at 37° C., shaking at 200 rpm until optical density reaches around 0.6;

4. Induction was performed using 0.1 mM IPTG at 16° C. overnight;

5. The cell lysate was loaded to an amylose affinity column and eluted using maltose; and 6. Enterokinase was used for cleavage of maltose binding protein (MBP).

7. Anion exchange and reversed phase-HPLC was used to purify the recombinant expressed ginsentides.

Isolation and Purification of Ginsentides from *Panax ginseng, P. Quinquefolius*, or *P. notoginseng*

About 1 kg of dried roots, leaves, seeds or flowers of *Panax ginseng, P. quinquefolius*, or *P. notoginseng* were extracted with 10 litres of water. After filtration, the filtrate was then loaded onto a C18 flash column (Grace Davison, US) and eluted with 70% ethanol. The eluted fractions were then loaded onto an SP Sepharose resin column (GE Healthcare, UK), eluted with 1 M NaCl (pH 3.0), and followed by ultrafiltration (ViVaflow 200, 2000 MWCO hydrostat). Further purification was performed by reversed-phase high performance liquid chromatography (RP-HPLC) (Shimadzu, Japan). A linear gradient of mobile phase A (0.05% $TFA/H_2O$) and mobile phase B (0.05% TFA/ACN) was used on the C18 column (250×22 mm, 5 μm, 300 Å) (Grace Davison, US).

This invention relates to the synthesis and use of ginsentides as a peptidogenic adaptogen to prolong our health span. The role of peptide adaptogenics is to extend the chronological clock of cellular and organismal ageing. In turn, they intervene age-related diseases and promote active and healthy ageing. Ginsentides in particular, are able to address cardiovascular diseases and frailty, which are the underlying cause of numerous chronic and old-age-related diseases such as cancer, cardiovascular diseases, inflammatory conditions, stress, and other metabolic conditions. FIG. 1 is a schematic diagram depicting the adaptogenic effects of ginsentide. The synthesis and uses of ginsentides will be described in the following sections:
1. Ginsentides production
2. Ginsentides as α1-adrenergic receptor antagonists and vasorelaxants of rat aorta ring
3. Ginsentides as nitric oxide-boosting agents
4. Ginsentides as anti-thrombotic agents
5. Ginsentides as anti-atherosclerotic agents
6. Ginsentides as protective agents against doxorubicin-induced cardiotoxicity
7. Ginsentides as anti-ageing and adaptogenic agent Example 1: Ginsentides Production The abundance of glycine and cysteine in the ginsentide sequence posed synthetic challenges in their synthesis of ginsentides, especially in the C-terminus. Attempts to synthesize ginsentides by a stepwise synthesis using solid-phase methods failed because the C-terminal fragments formed aggregates, preventing a successful synthesis. Therefore, the present invention described a stepwise solid-phase synthesis strategies of the chemical synthesis of ginsentides to overcome these synthetic challenges. In particular, a strategically selected Gly residue was alkylated by a reversible protecting group to prevent aggregation to permit a successful synthesis of ginsentide TP1 as a representative example.

An organic oxidative folding system for disulfide bond formation has been invented. Using this invention, the oxidative folding is accelerated a thousand fold in forming native disulfide bonds of cysteine-rich peptides within minutes (e.g. within 1, 2, 3, 4, 5, 6, 7, 8, 9, 10, 15, 20, 25, 30, 35, 40, 45, 50, 55, or 59 minutes) instead of hours. The invention also improves reaction yield and can be performed in high peptide concentrations without observable peptide precipitations. In addition, all reagents used in this method are inexpensive, which makes the synthesis economically favorable. Thus, it can be applied to large scale production of cysteine-rich peptides.

Recombinant expression of ginsentides is advantageous as the use of chemicals for the production of ginsentides will be eliminated. Moreover, the expressed ginsentides produced using the recombinant expression platform will be in its folded state, making the second step of oxidative folding unnecessary.

Figure 2:
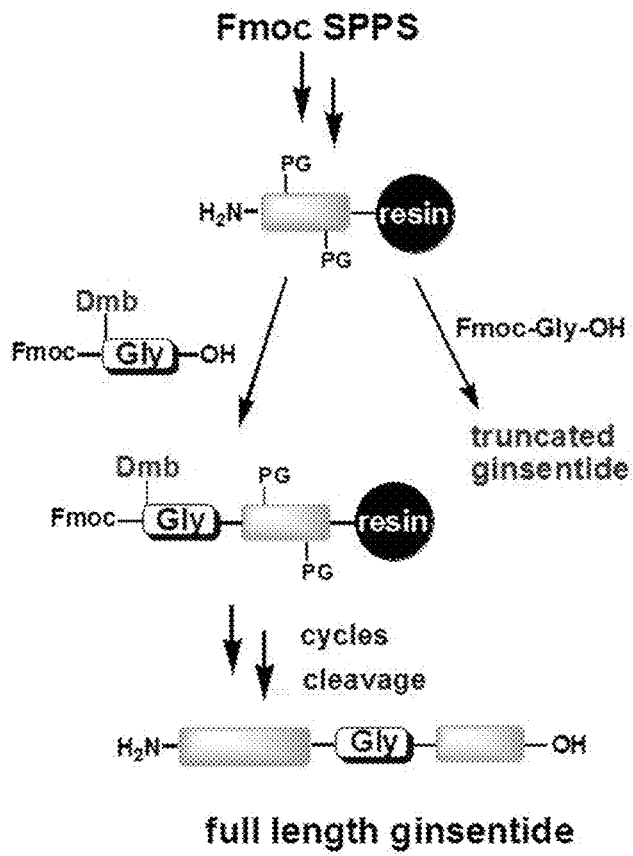
FIG. 2. Schematic flow for the chemical synthesis of ginsentides.
Figure 3:
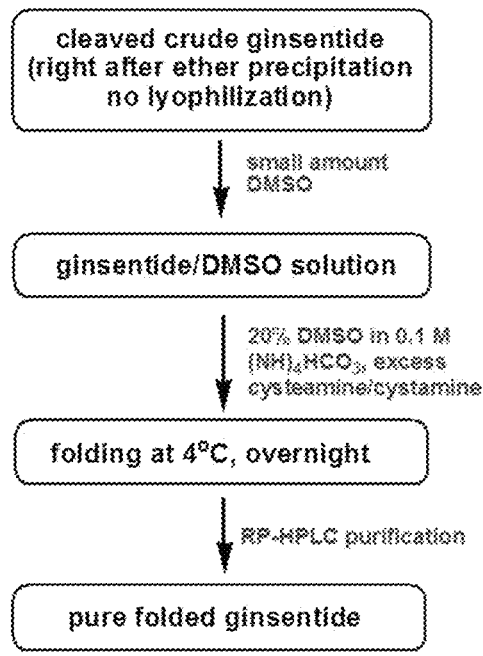
FIG. 3. Oxidative folding strategies for synthetic ginsentide TP1.
Figure 4:
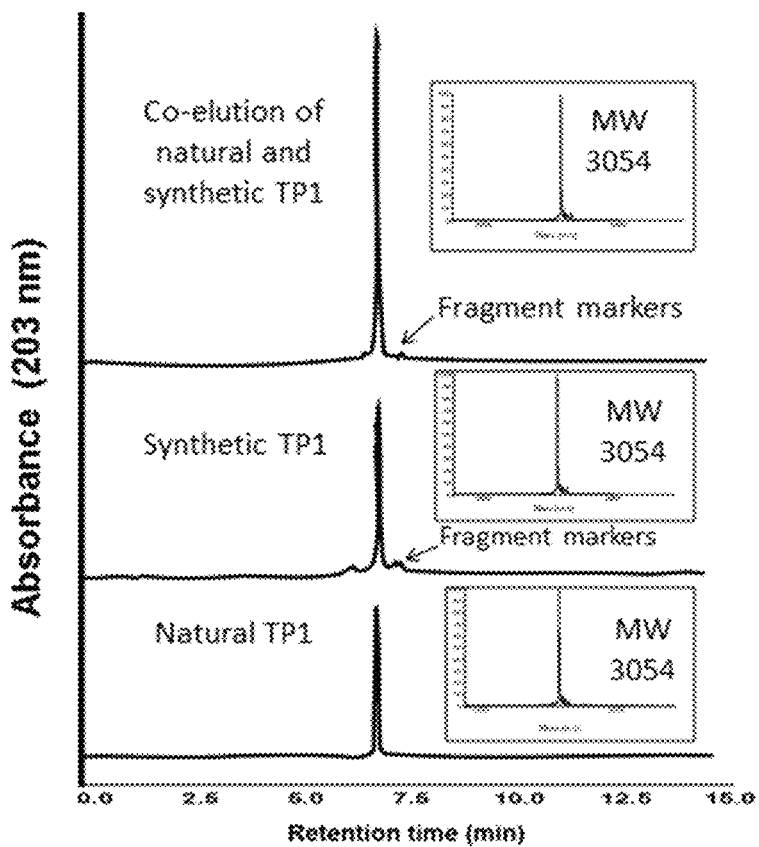
FIG. 4. Comparison of natural and synthetic Ginsentide TP1 using UHPLC and MALDI-MS.
Figure 5:
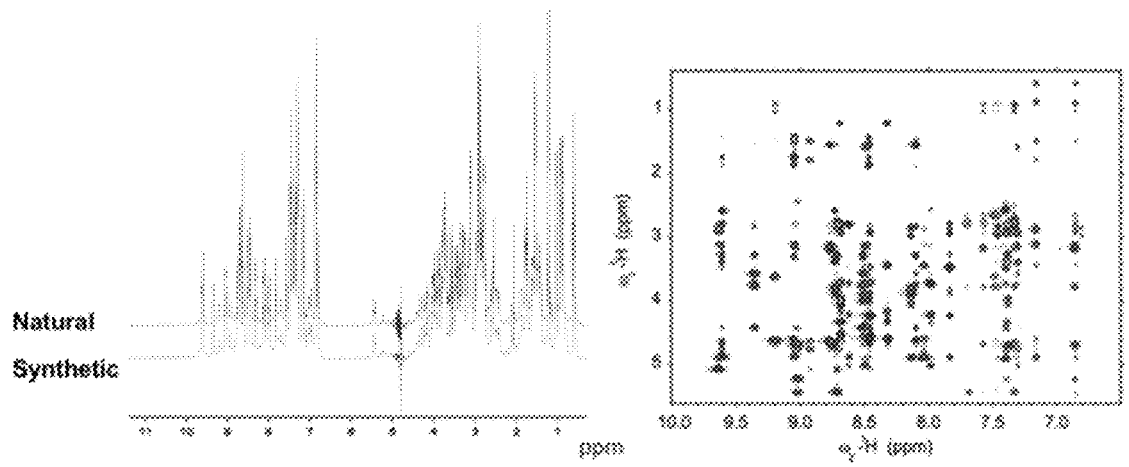
FIG. 5. Comparison of natural and synthetic Ginsentide TP1 using 1D and 2D NMR.
Figure 6:
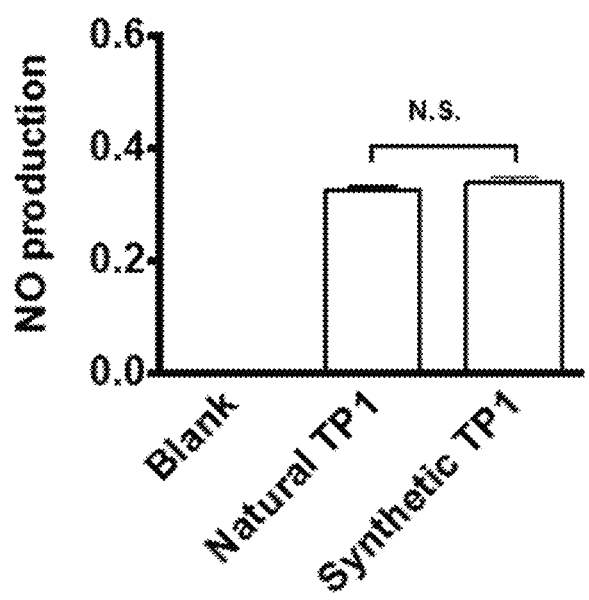
FIG. 6. Functional comparisons of natural and synthetic Ginsentide TP1 on nitric oxide production.
Figure 9:
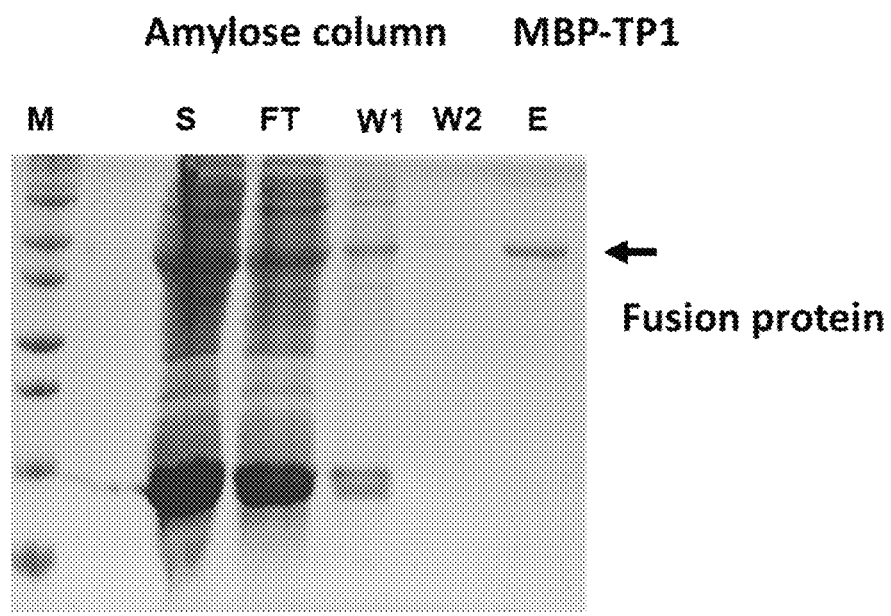
FIG. 9. Purification of MBP-TP1 fusion protein by amylose column. S— Cell lysate; FT—Column flowthrough; W1—$1^{st}$ wash; W2—$2^{nd}$ Wash; E—Eluted proteins FIG. 10. Removal of MBP tag by enterokinase.
Figure 10:
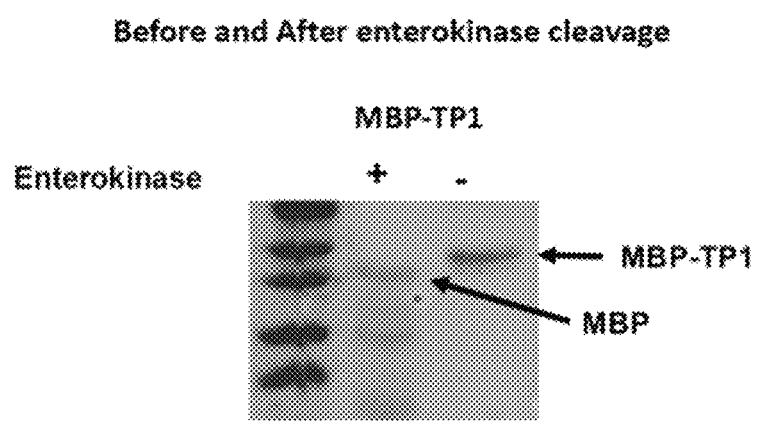
Figure 11:
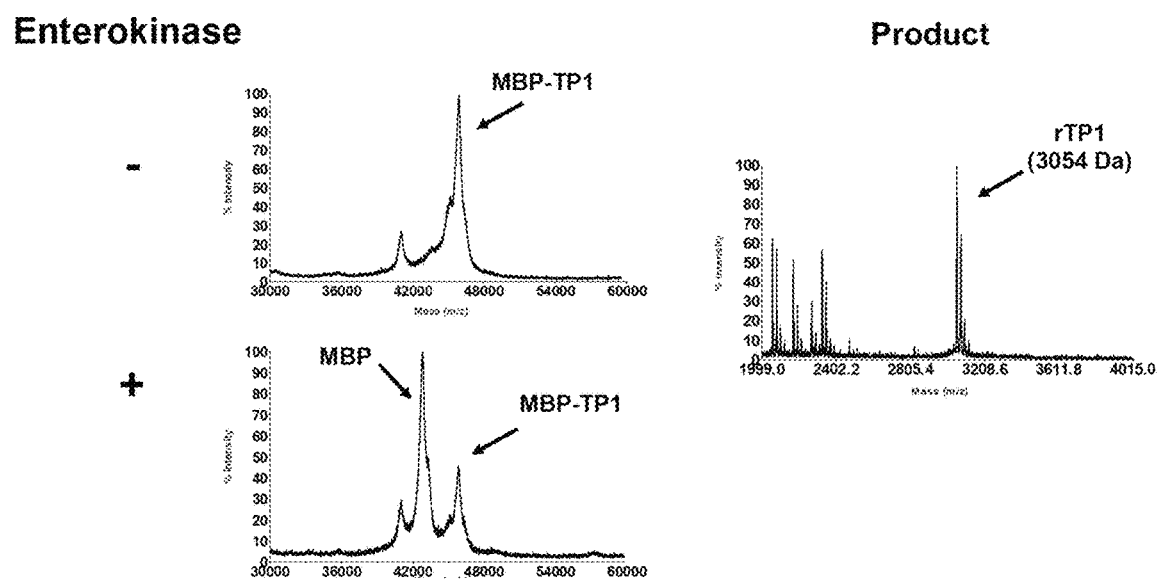
FIG. 11. Mass spectrometry profile before and after enterokinase cleavage.

Technical Description of the Invention
i. Table 1 illustrates the amino acid sequence of ginsentides.
ii. FIG. 2 shows the schematic flow for the chemical synthesis of ginsentides
iii. FIG. 3 shows the oxidative folding strategies for synthetic ginsentide TP1
iv. FIG. 4, 5, 6 shows that the synthetic ginsentide is identical to natural ginsentides, and is functionally indistinguishable from natural ginsentide obtained from ginseng.
v. FIG. 7-11 shows the recombinant expression scheme for ginsentide.

Oxidative folding relates to an approach for forming disulfide bonds in peptides and proteins. In this method, reduced or partially oxidized peptides are fully oxidized in a nonaqueous system using organic solvents and compatible organic reducing and oxidizing (redox) reagents.

The rationale of our invention is based on the observation that oxidative folding is mediated by thiol-disulfide exchange reactions which are SN2 reaction. Such reactions are strongly favored in organic solvents than in aqueous conditions in which the attacking thiol nucleophiles are being solvated by water. Eliminating water in the oxidative folding condition should accelerate the thiol-disulfide exchange reactions, and in turn, the oxidative process.

In this invention, four major components are introduced: an organic base, organic solvent, structure-enhancing co-solvent and redox reagents. An organic base, such as pyridine, imidazole or morpholine, is used to provide a suitable basicity for the disulfide formation while organic solvent provides an environment in which the thiol-disulfide exchange reaction is one thousand times faster than in aqueous conditions, which are the prevailing practice in literature. In addition, structure-enhancing co-solvents and redox reagents ensure the correct disulfide paring of folding products. Using structure-enhancing solvents such as trifluoroethanol (TFE), the native secondary structure is formed preferentially, thus bringing the native pairing of cysteines in proximity to form the correct disulfide connections. Using organic-solvent-compatible reductant such as cysteamine and oxidant dimethyl sulfoxide (DMSO), the incorrect disulfide connection is able to be shuffled to the correct disulfide connection by thiol-disulfide exchange reactions.

The reduced peptides can be synthesized by either solid/solution phase synthesis or recombinant expression. Then it is purified and lyophilized. Reduced peptides are dissolved in pure DMSO, which also acts as a mild oxidant, and diluted with organic solvents to a final concentration of 0.1 mM to 1 mM. Subsequently, an organic base and reductants are added. The reductant can be dissolved in a small amount of water if it is not soluble in organic solvents. It is preferred that the final volume of water should not exceed 20% of the whole mixture.

The aforesaid procedure is employed to fold a cyclic peptide kalata B1 (kB1) as an example. Dissolve fully reduced kB1 in DMSO as a stock. Add 2-propanol as the organic solvent to dilute the peptide stock. Then add organic bases including pyridine, imidazole or morpholine and the reductant cysteamine. Each condition contains 100 µM of reduced kB1, 10% (v/v) DMSO and 100 mM cysteamine with various concentrations of solvent and base.

Figure 12:
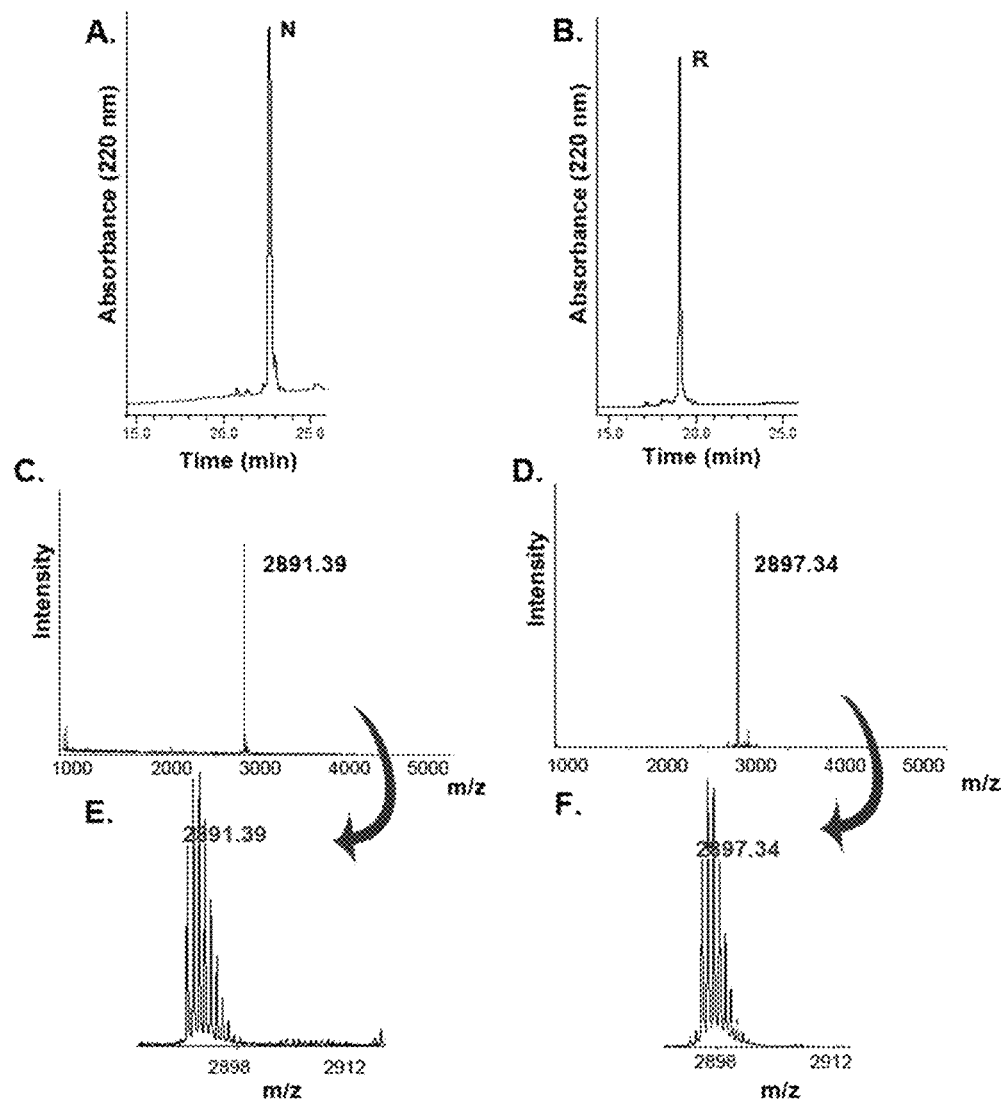
FIG. 12. RP-HPLC and MALDI-TOF MS profiles of native and reduced kB1. Panel A and B show the RP-HPLC profiles of native and reduced kB1 with "N" and "R" representing native and reduced respectively. Panel C and D show the MS profiles of the peaks N and R accordingly. Panel E and F are the zoom-in profile of MS results in panel C and D, which demonstrate the difference between these two masses.

FIG. 12 shows the RP-HPLC and MALDI-TOF MS profiles of native and reduced kB1.

Table 4 shows the oxidative folding conditions of kB1 with varying solvent combinations.

FIG. 13 shows the RP-UPLC profiles of oxidative folding of kB1 showing the effect of different bases.

Figure 14:
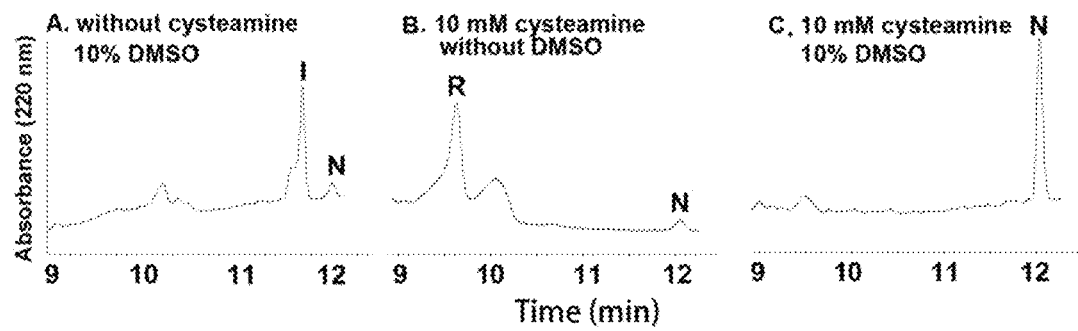
FIG. 14. RP-UPLC profiles of oxidative folding of kB1 showing the effect of cysteamine and DMSO as redox agents. "R" and "N" represent the reduced and native forms of kB1 while "I" indicates the folding intermediate.

FIG. 14 shows the RP-UPLC profiles of oxidative folding of kB1 and the effect of cysteamine and DMSO as redox agents.

Figure 15:
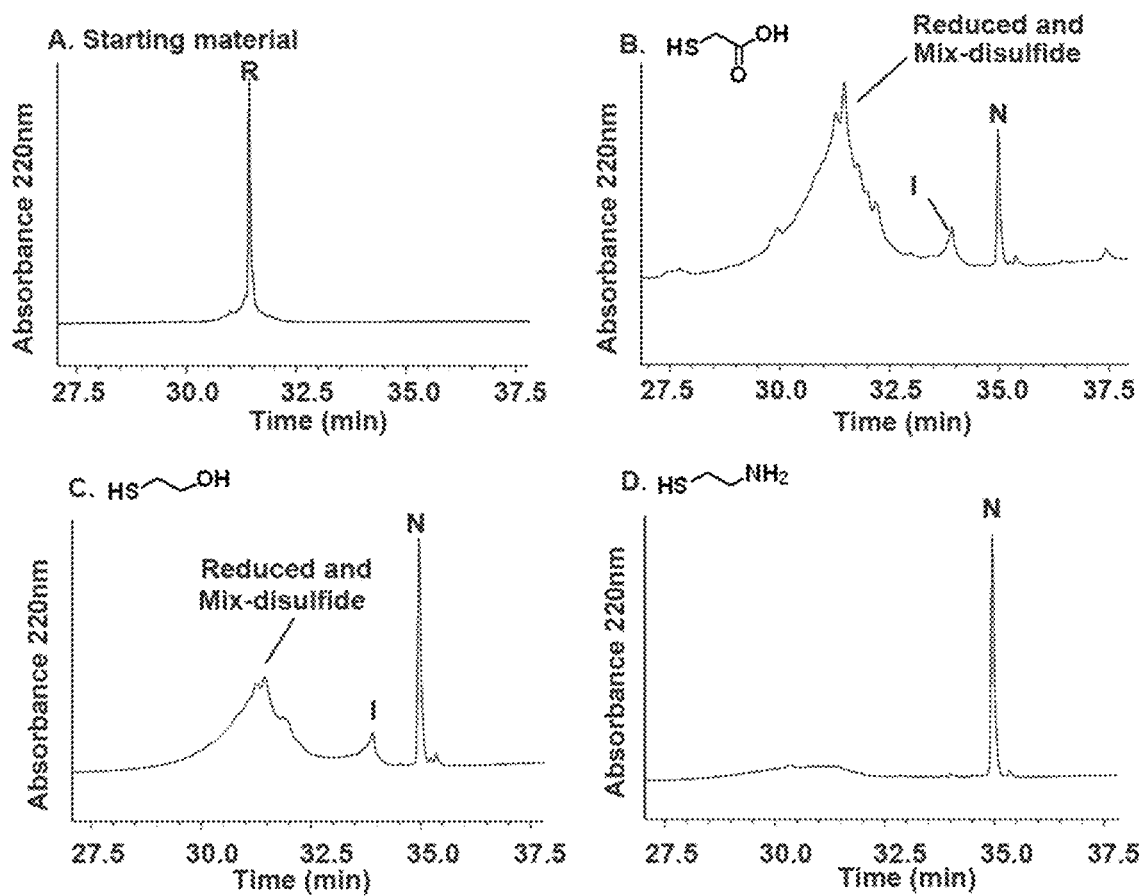
FIG. 15. RP-HPLC profiles of oxidative folding of kB1 with different thiols as reducing reagents. A. Reduced kB1; B. Conditions containing 10 mM mercaptoacetic acid; C. Conditions containing 10 mM 2-mercaptoethanol; D. Conditions containing 10 mM cysteamine. "R" and "N" represent the reduced and native forms of kB1 while I indicates the folding intermediate. All conditions contained 100 μM peptide, 100 mM thiol, 10% (v/v) DMSO, 85% 2-propanol and 5% morpholine.

FIG. 15 shows the RP-HPLC profiles of oxidative folding of kB1 with different thiols as reducing reagents.

Figure 16:
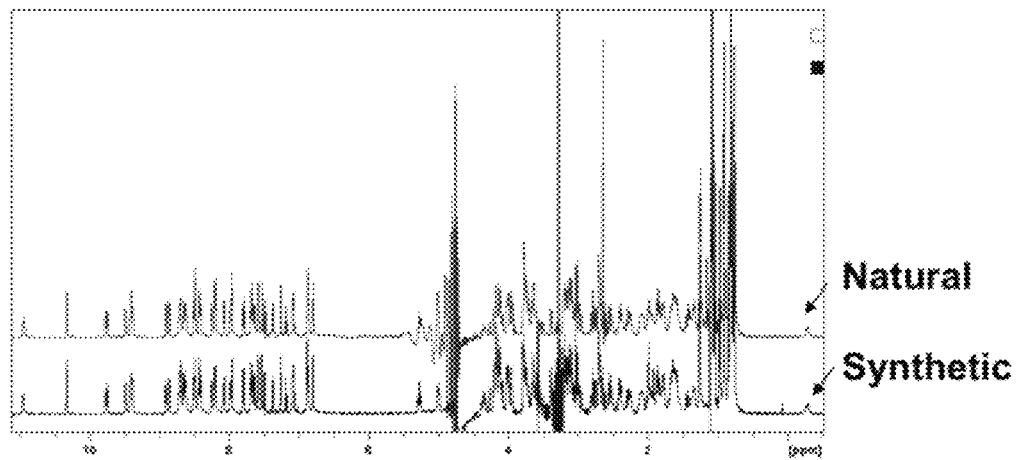
FIG. 16. $^1$H NMR spectra comparison of the natural kB1 (red) and the synthetic one (blue). Both peptides were dissolved in 90% $H_2O$/10% $D_2O$ at pH 4.3. The spectra were obtained by a NMR spectrometer (600 MHz) at 298K.

FIG. 16 compares the 1H NMR spectra comparison of the natural and synthetic kB1 prepared by organic oxidative folding.

TABLE 4

Oxidative folding conditions of kB1 with varying solvent concentrations

| | Base (v/v %) | | | 2-propanol | DMSO | Cysteamine Conc. | Peptide Conc. | Yield* |
|---|---|---|---|---|---|---|---|---|
| Run | Pyridine | Morpholine | Imidazole | (%) | (%) | (mM) | (µM) | (%) |
| 1 | 5 | | | 85 | 10 | 100 | 100 | 27 |
| 2 | 30 | | | 60 | 10 | 100 | 100 | 72 |
| 3 | 50 | | | 40 | 10 | 100 | 100 | 82 |
| 4 | 90 | | | 0 | 10 | 100 | 100 | 8 |
| 5 | | | 5 | 85 | 10 | 100 | 100 | 80 |
| 6 | | | 10 | 80 | 10 | 100 | 100 | 83 |
| 7 | | | 15 | 75 | 10 | 100 | 100 | 84 |
| 8 | | 5 | | 85 | 10 | 100 | 100 | 88 |
| 9 | | 10 | | 80 | 10 | 100 | 100 | 89 |
| 10 | | 20 | | 70 | 10 | 100 | 100 | 91 |
| 11 | | 30 | | 60 | 10 | 100 | 100 | 90 |

*Yields are calculated accordingly based on RP-HPLC profiles of reactions at 1 h.

Example 2. Ginsentides as α1 Adrenergic Receptor Antagonists and Vasorelaxants of Rat Aorta Ring The present invention shows that ginsentide TP1 has vasorelaxation properties.

Plant peptides and proteins are often underexplored as bioactive constituents in medicinal plants. Unlike other peptides and proteins, multiple intramolecular disulfide bonds stabilize cysteine-rich peptides making them extremely stable against heat, acid and enzymatic degradation. The present invention shows that ginsentide TP1, a cysteine-rich peptide, has eight cysteine residues (four stable disulfide bonds) and a unique pseudo-cyclic structure, making it stable against heat, acid, serum and proteolytic degradation.

Cysteine-rich peptides are highly cross-linked by intramolecular disulfide bridges. This forces the bulky hydrophobic side chains to expose outward, making the surface of the molecule more lipophilic. Also, the slow exchange of D20 indicates that the hydrogen bonding of ginsentides are intramolecularly connected instead of exposing outwards. These characteristics desolvate ginsentides from water. Therefore, the unique features of ginsentides could improve the intrinsic cell permeability and intestinal absorption, making it orally active.

Technical Description

Figure 17:
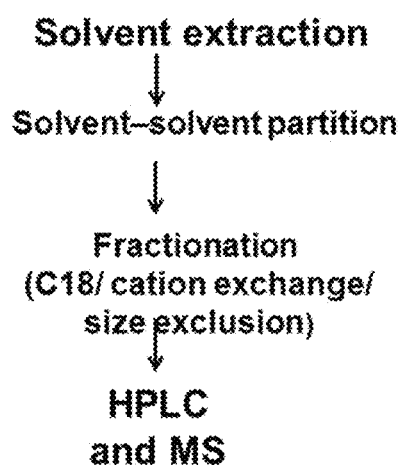
FIG. 17. Scheme for the purification of ginsentides from plant materials.

FIG. 17 shows a schematic purification of ginsentides from ginseng plants. All ginsentides including TP1 (herein refer as natural ginsentide TP1) were purified to high homogeneity through solvent-solvent partition, ion-exchange, size exclusion, and reverse-phase high-pressure liquid chromatography. The yields of ginsentides from different plant tissues vary >10 fold, with the highest yield from seeds and flowers (0.2-0.4%) and the lowest from roots and leaves (0.01-0.03%). Thus, from 1 kg of dried flowers or seeds nearly 400 mg of ginsentides could be obtained.

Table 1 illustrates the amino acid sequence of ginsentides.

Figure 18:
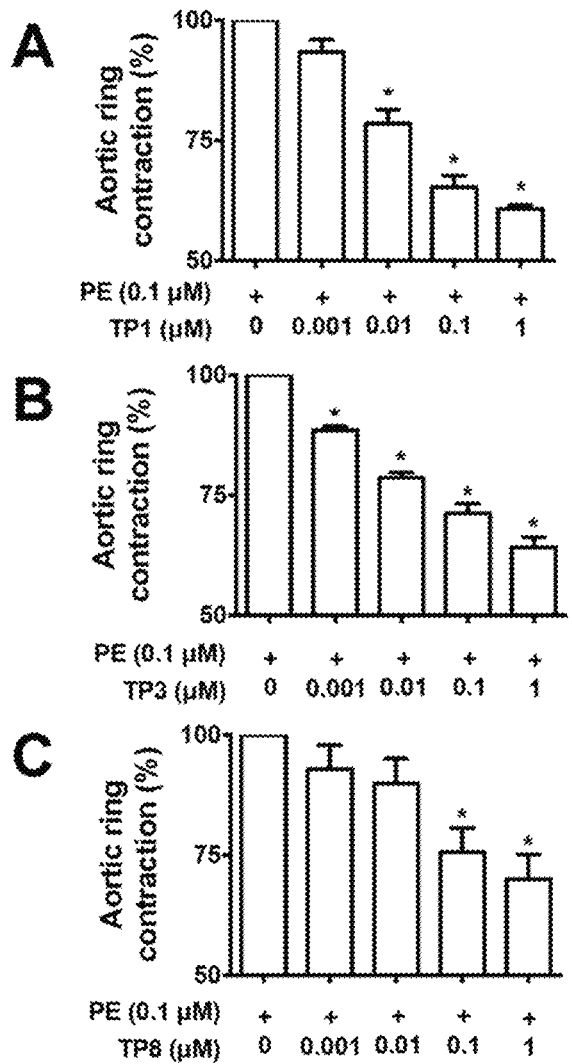
FIG. 18. Ginsentide TP1, TP3 and TP8 antagonized phenylephrine-induced aortic ring contraction.
Figure 19:
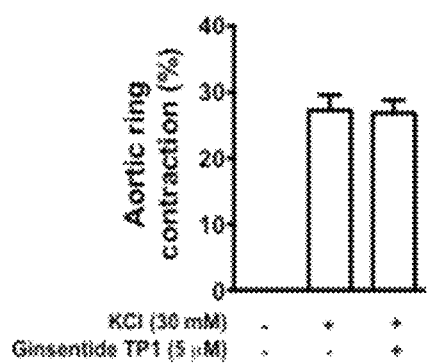
FIG. 19. Ginsentide TP1 does not antagonized KCI-induced contracted aortic ring.

FIGS. 18 and 19 shows that ginsentide TP1, TP3 and TP8 relaxes phenylephrine-induced aortic ring contraction, but not KCl-induced contracted aortic ring. To examine the vasomotor response of ginsentide TP1, isolated thoracic aorta was pre-contracted with KCl (30 mM) or a selective α1-adrenergic receptor agonist, phenylephrine (0.1 µM). Isometric tension was recorded as a measurement for aortic ring contraction. The ex-vivo results showed that ginsentide TP1 inhibits phenylephrine-induced aortic ring contraction in a dose-dependent manner ($p<0.05$), but not in the KCl-treated group.

Table 5 shows that ginsentide TP1 is metabolically stable

Figure 20:
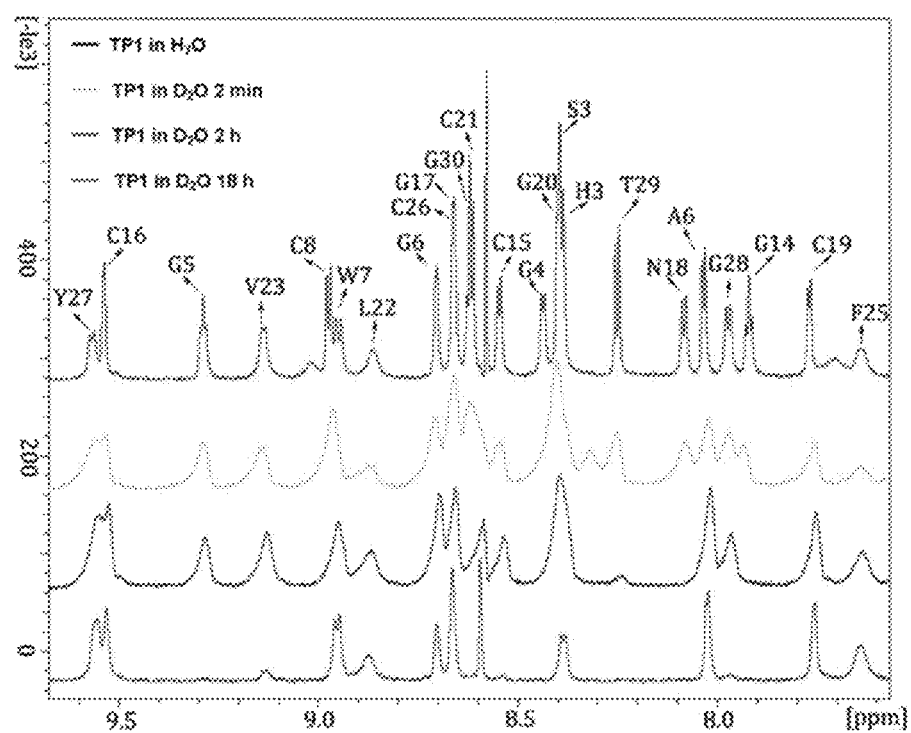
FIG. 20. D2O exchange of Ginsentide TP1 by 1D NMR.

FIG. 20 shows the slow exchange of D20 indicating that the extensive hydrogen bonding network in ginsentide TP1 to confer their structurally stability.

Figure 21:
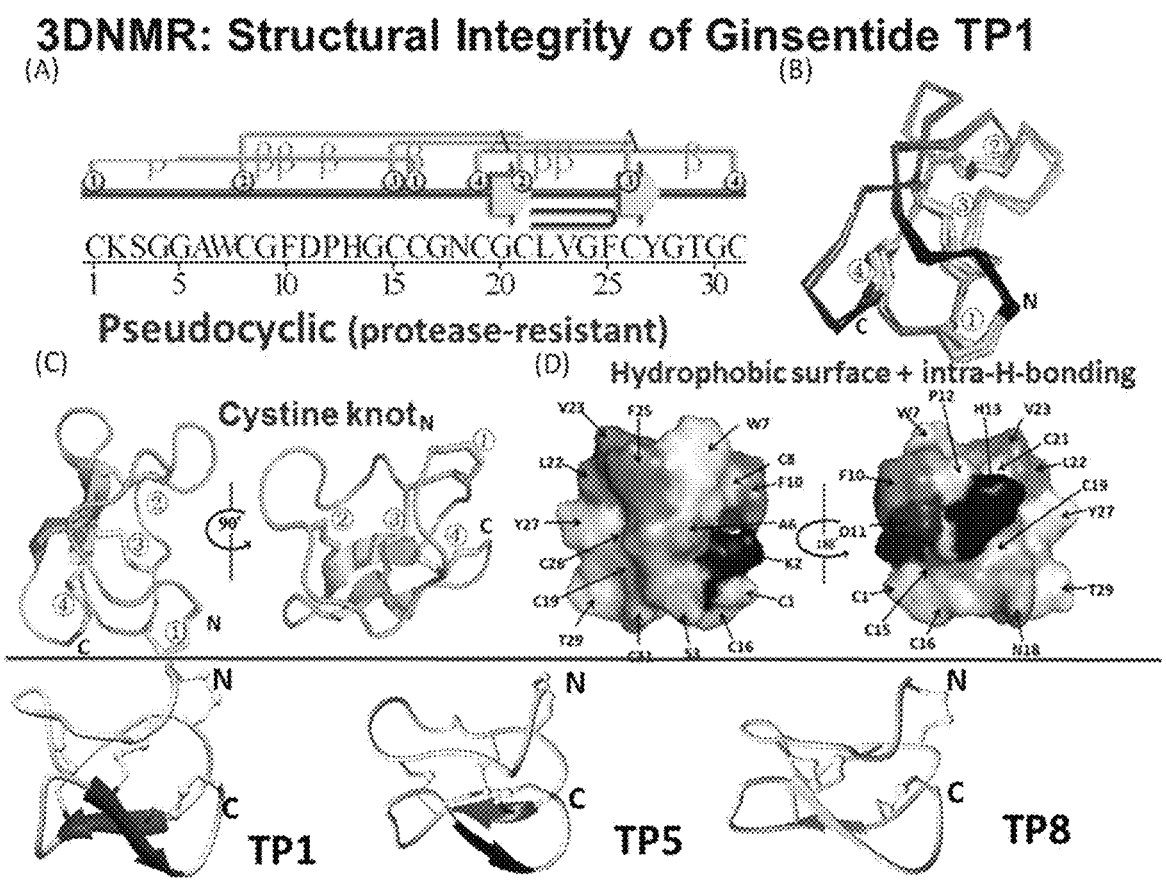
FIG. 21. Amino acid sequence, second and tertiary structures of ginsentides Primary and secondary structure (top left), the overall lay of synthetic and natural TP1 (top right), the CPK model of the hydrophobic surface of TP1 (middle panels) and the 3D structure of TP5 and TP8 as determined by NMR (bottom panel). TP1: SEQ ID NO:1.

FIG. 21 shows the sequence of TP1, its secondary structure, the overall lay of synthetic and natural TP1, the CPK model of the hydrophobic surface of TP1 and the 3D structure of TP.

TABLE 5

Ginsentide TP1 is metabolically stable

| Conditions | Initial concentration remaining (%) |
|---|---|
| Heat (100° C., 2 h) | >71 |
| Acid (0.2M HCl, 1 h) | >99 |
| Trypsin (37° C., 1 h) | >87 |
| Chymotrypsin (37° C., 1 h) | >90 |
| Pepsin (37° C., 1 h) | >99 |
| Human Serum (37° C., 48 h) | >92 |

Example 3. Ginsentides as Nitric Oxide-Boosting Agents

The present invention shows that ginsentide TP1 induces nitric oxide synthesis. In comparison to the major members of ginsenosides such as Rg1 and Rb1 in ginseng, ginsentide TP1 is more effective than ginsenoside Rg1 and Rb1 in nitric oxide synthesis.

Plant peptides and proteins are often underexplored as bioactive constituents in medicinal plants. Unlike other peptides and proteins, multiple intramolecular disulfide bonds stabilize cysteine-rich peptides making them extremely stable against heat, acid and enzymatic degradation. The present invention shows that ginsentide TP1, a cysteine-rich peptide, has eight cysteine residues (four stable disulfide bonds) forming a unique pseudo-cyclic structure, making it resistant to heat, acid, serum proteolytic degradation.

Ginsentides are cysteine-rich peptides and highly cross-linked by intramolecular disulfide bridges. Because ginsentides are 31 amino acids in length and contain four disulfide bridges, ginsentides have an inside-out arrangement with the inside core filled by the four disulfide linkages. Consequently, such a structural arrangement forces the bulky hydrophobic side chains to expose outward, making the surface of the molecule more lipophilic. Indeed, the surface of ginsentide is generally consisted of hydrophobic amino acids as determined by 3D NMR. Also, ginsentides are highly compact with an extensive network of stable intra hydrogen bondings as indicated by the slow exchange of D20 in an NMR study. Intra-hydrogen bondings not only stabilize the ginsentide structures but also desolvate ginsentides from external hydrogen-bonding with water. Together, these unique features of ginsentides improve their cell permeability and intestinal absorption, making them bioavailable. In other words, ginsentides have a small-molecule-like stability and oral bioavailability, but a large foot print to increase their on-target specificity and decrease their probability of off-target side effects than small molecules.

Technical Description of the Invention

Table 1 illustrates the amino acid sequence of ginsentides.

Figure 22:
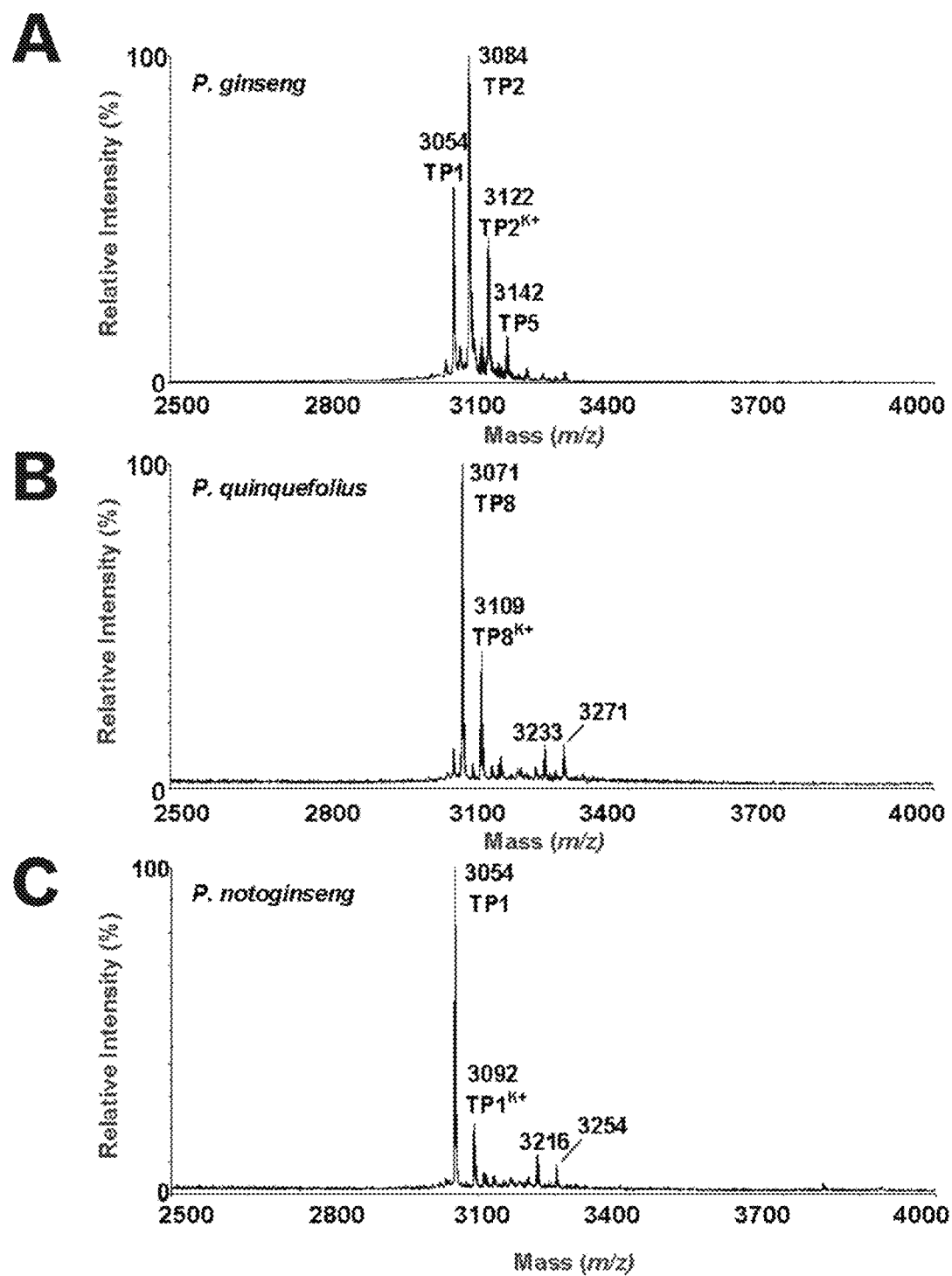
FIG. 22. Mass spectrometry profiles of the aqueous extracts of roots of (A) *Panax ginseng*, (B) *Panax quinquefolius* and (C) *Panax notoginseng* using MALDI-TOF MS.

FIG. 22 shows the profiles of ginsentides in the three most commonly used ginseng species: P. ginseng, P. quinquefolius and P. notoginseng.

Figure 23:
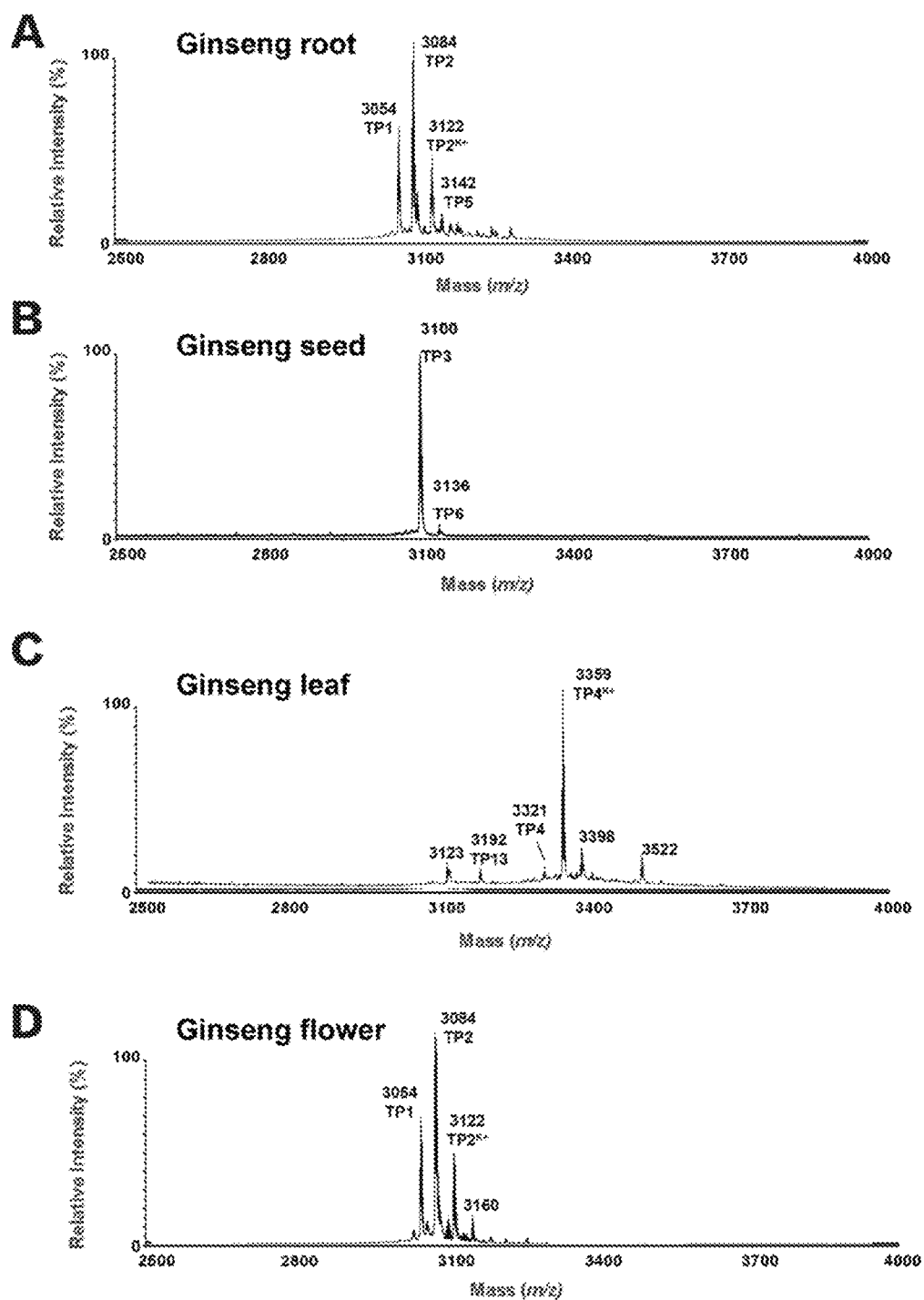
FIG. 23. Mass spectrometry profiles of the aqueous extracts of (A) roots, (B) seeds, (C) leaves and (D) flowers of *Panax ginseng* using MALDI-TOF MS.

FIG. 23 shows the tissue distribution of ginsentides in P. ginseng.

Figure 24:
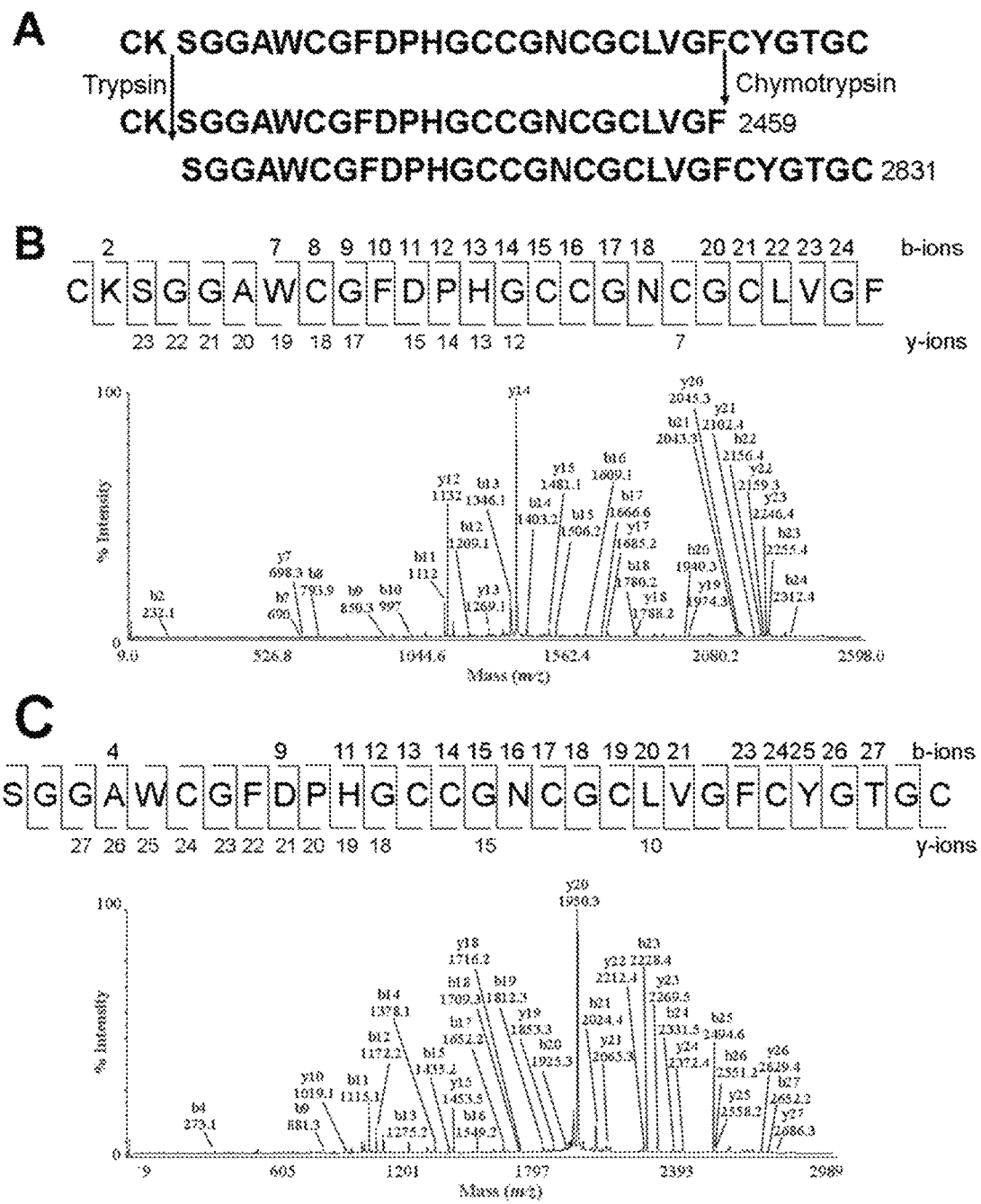
FIG. 24. De novo sequencing of ginsentide TP1. Enzymatic digestion of S-reduced peptides by chymotrypsin and trypsin generated one major fragment each with m/z values of 2459 (SEQ ID NO:131) and 2831 (SEQ ID NO:132), respectively. The sequence of fragments were deduced using the b-ions and y-ions generated from MALDI-TOF MS/MS.

FIG. 24 shows the de novo sequencing of ginsentide TP1.

FIG. 25 shows the disulfide connectivity of ginsentide TP1.

FIG. 26 illustrates the ginsentide-encoding transcripts in all three commonly used ginseng species: P. ginseng, P. quinquefolius and P. notoginseng.

Figure 27:
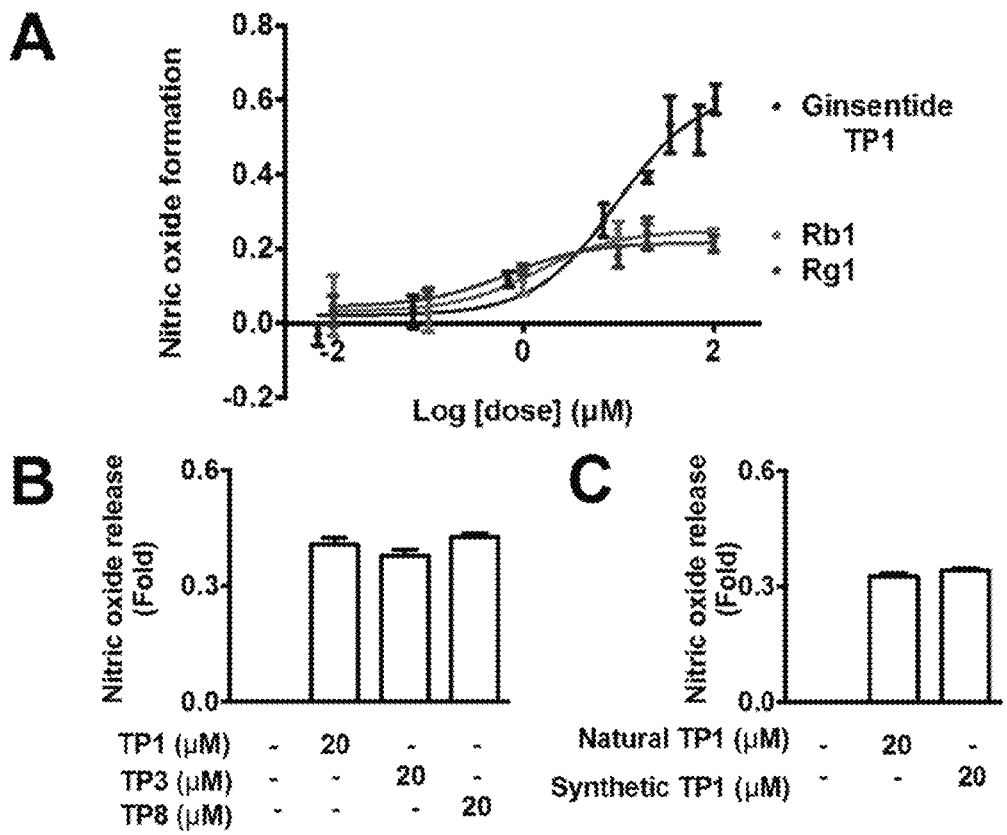
FIG. 27. shows that ginsentide TP1 increases cellular NO synthesis from human endothelial cells (HUVEC-CS). Comparatively, ginsentide TP1 shows a three-fold increase in potency and magnitude NO release than both ginsenosides Rb1 and Rg1. Ginsentide TP1, TP3, TP8 and synthetic TP1 shows comparable cellular NO release.

FIG. 27 shows that ginsentide TP1 increases cellular NO synthesis from human endothelial cells (HUVEC-CS). Comparatively, ginsentide TP1 shows a three-fold increase in potency and magnitude NO release than both ginsenosides Rb1 and Rg1. Ginsentide TP1, TP3, TP8 and synthetic TP1 shows comparable cellular NO release.

Figure 28:
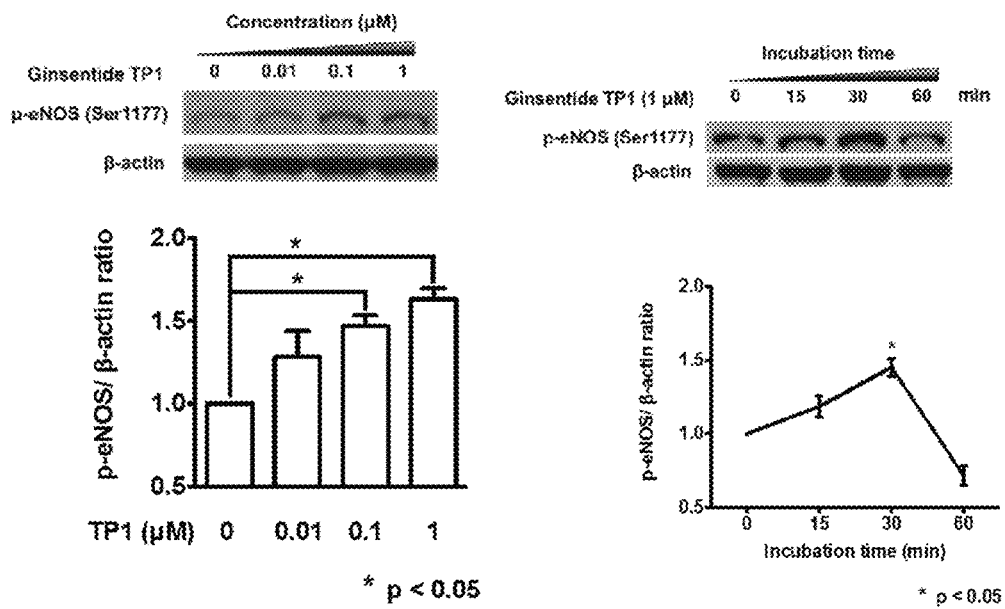
FIG. 28. Ginsentide TP1 activates endothelial nitric oxide synthase. Representative western blot analysis on the dose-dependent and time-dependent effects of ginsentide TP1 on phosphorylated eNOS (p-eNOS) accumulations in HUVEC-CS cells. All results were expressed as mean±S.E.M. from three separate experiments. * P<0.05 compared to ginsentide tP1 treated-group.

FIG. 28 shows that ginsentide TP1 induces the accumulation of phosphorylated eNOS (p-eNOS). 1 µM of ginsentide TP1 induced the accumulation of p-eNOS in approximately 30 min.

Figure 29:
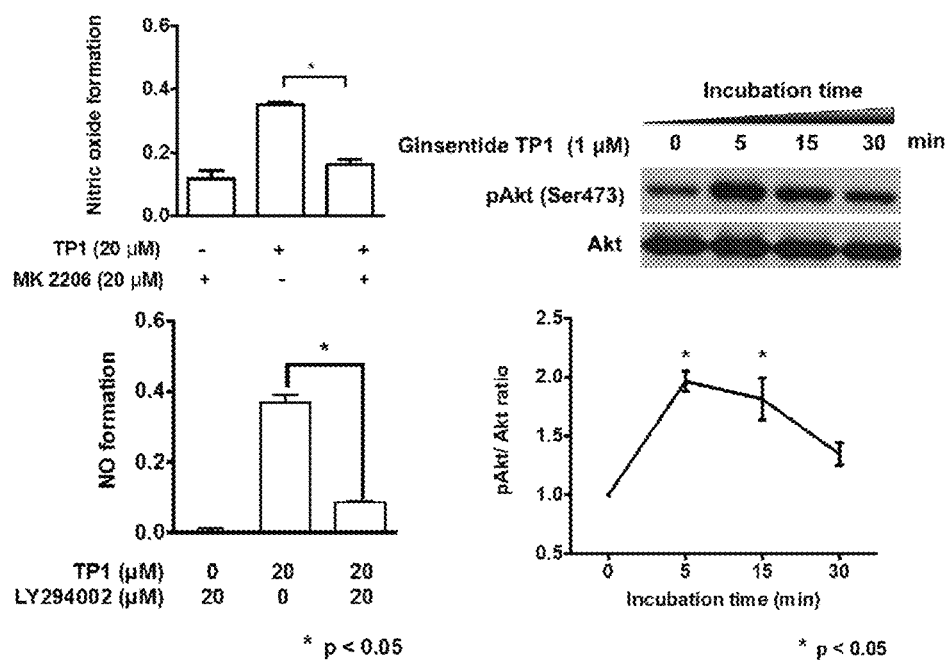
FIG. 29. Ginsentide TP1 induced nitric oxide formation involves PI3K/Akt signaling. HUVEC-CS cells were exposed to ginsentide TP1 and (A) MK 2206 (Akt inhibitor) or (B) LY294002 (PI3K inhibitor) for 1 h. Intracellular NO production was measured by DAF-2 DA staining and expressed as normalized fluorescence intensity (C) Representative western blot analysis of time-dependent effects of ginsentide TP1 on Akt phosphorylation in HUVEC-CS cells. All results were expressed as mean±S.E.M. from three separate experiments. * P<0.05 compared to ginsentide TP1 treated-group.

FIG. 29 shows that ginsentide TP1 induced nitric oxide formation involves PI3K/Akt signaling.

Table 5 shows that ginsentide TP1 is metabolically stable

Figure 30:
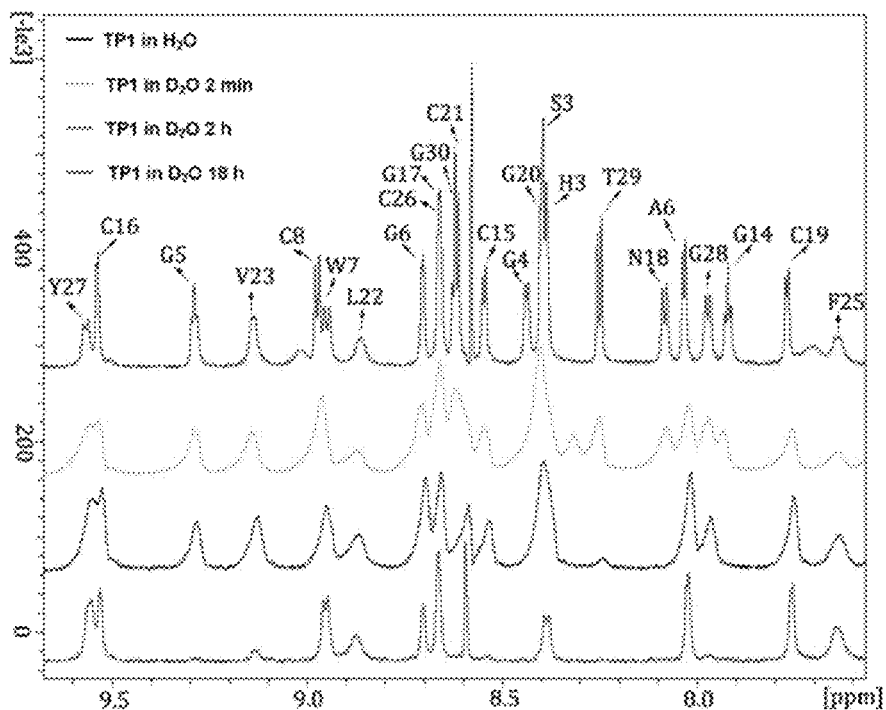
FIG. 30. $D_2O$ exchange of Ginsentide TP1 by 1D NMR.

FIG. 30 shows the slow exchange of D20 indicating that the extensive hydrogen bonding network in ginsentide TP1 to confer their structurally stability.

Figure 31:
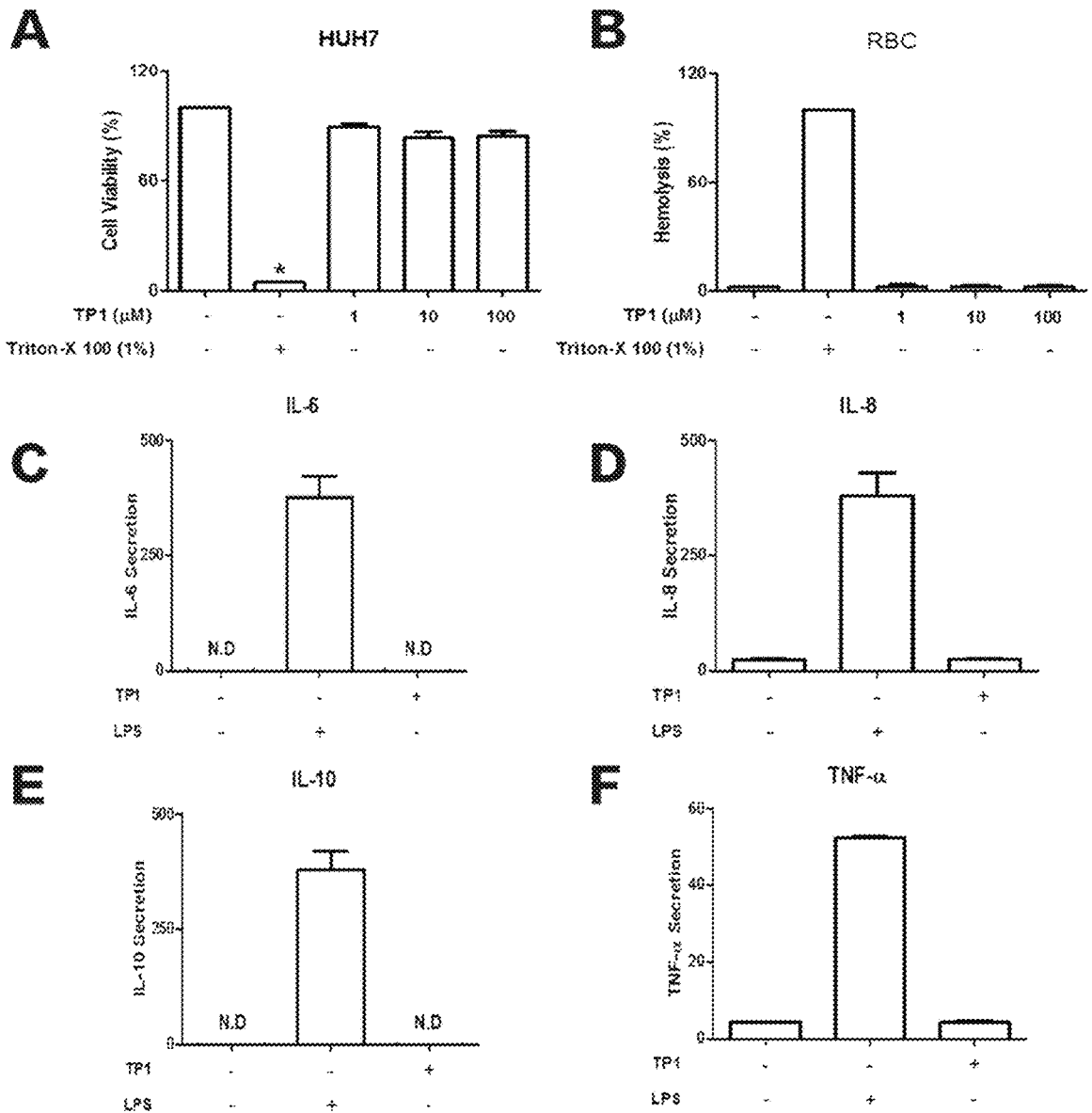
FIG. 31. Ginsentide TP1 does not show (A) cytotoxic activities in Huh7 cells and (B) hemolytic effects. Ginsentide TP1 does not induce (C) IL-6, (D) IL-8, (E) IL-10, and (F) TNF-α release from THP-1 cells. LPS was used as positive control. All results were expressed as mean±S.E.M. (n=3). *P<0.05 compared to control group.

FIG. 31 shows that ginsentide TP1 is not cytotoxic to cells and hemolytic to red blood cells. Ginsnetide TP1 is not immunogenic.

Example 4. Ginsentides as Anti-Thrombotic Agents

The present invention shows that ginsentide TP1 has antagonistic effects against P2y12 activation. In comparison to the main ginsenosides in ginseng, ginsentide TP1 is more effective than ginsenoside Rg1 and Rb1 in antagonizing P2y12 activation. Ginsentide TP1 also exerts anti-platelet aggregative effects in vivo.

Plant peptides and proteins are often underexplored as bioactive constituents in medicinal plants. Unlike other peptides and proteins, multiple intramolecular disulfide bonds stabilize cysteine-rich peptides making them extremely stable against heat, acid and enzymatic degradation. The present invention shows that ginsentide TP1, a cysteine-rich peptide, has eight cysteine residues (four stable disulfide bonds) and a unique pseudo-cyclic structure, making it stable against heat, acid, serum and proteolytic degradation.

Cysteine-rich peptides are highly cross-linked by intramolecular disulfide bridges. This forces the bulky hydrophobic side chains to expose outward, making the surface of the molecule more lipophilic. Also, the slow exchange of D20 indicates that the hydrogen bonding of ginsentides are intramolecularly connected instead of exposing outwards. These characteristics desolvate ginsentides from water. Therefore, the unique features of ginsentides could improve the intrinsic cell permeability and intestinal absorption, making it orally active.

Technical Description of the Invention

Table 1 illustrates the amino acid sequence of ginsentides.

Figure 32:
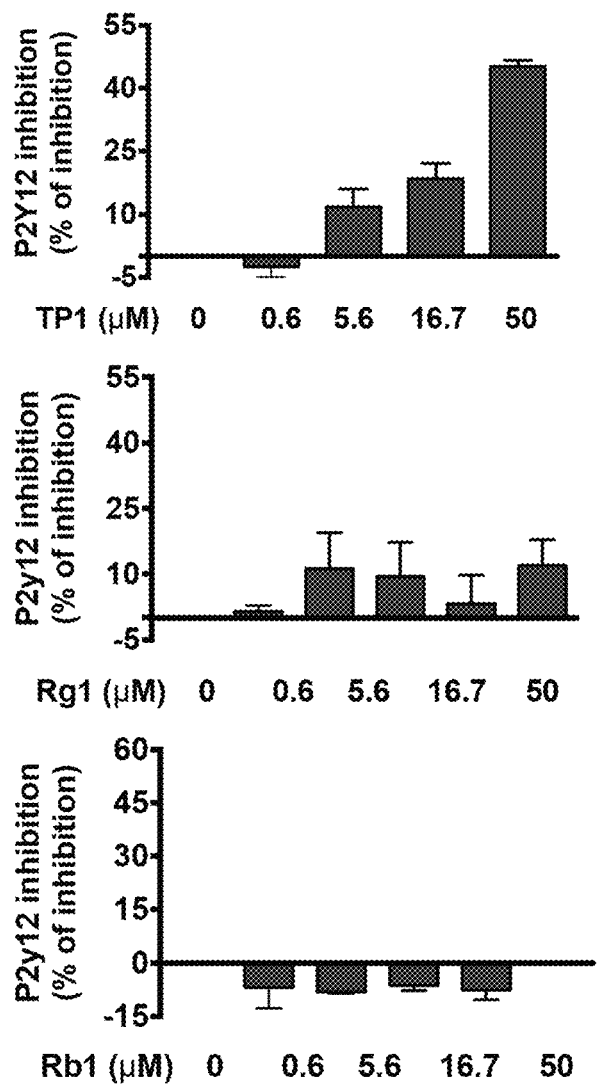
FIG. 32. Ginsentide TP1 antagonizes P2y12 activation. Ginsentide TP1, ginsenosides Rb1 and Rg1 were tested in antagonist mode with the P2y12 Arrestin Biosensor Assay using 6.4 nM 2-methylthio-ADP to induce P2y12 activation. P2y12 activation was measured by relative luminescence units and expressed as percentage of inhibition relative to blank.

FIG. 32 show that ginsentide TP1 antagonize P2y12 activation. Comparatively, ginsentide TP1 is more effective than both ginsenosides Rb1 and Rg1.

Figure 34:
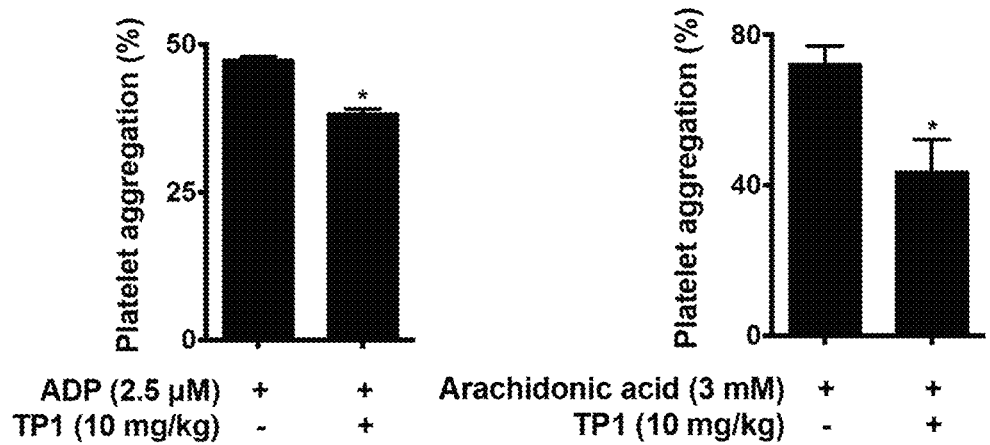
FIG. 34. Ginsentide TP1 inhibits platelet aggregation in vivo. 10 mg/kg ginsentide TP1 was injected to SD rat intravenously for 20 min. Platelet-rich plasma was isolated by centrifugation. Platelet aggregation was examined upon ADP or arachidonic acid stimulation.

FIG. 34 show that ginsentide TP1 inhibits platelet aggregation in vivo

Table 4 illustrates that ginsentide TP1 is stable against heat, acid, proteolytic and serum-mediated degradation.

Figure 33:
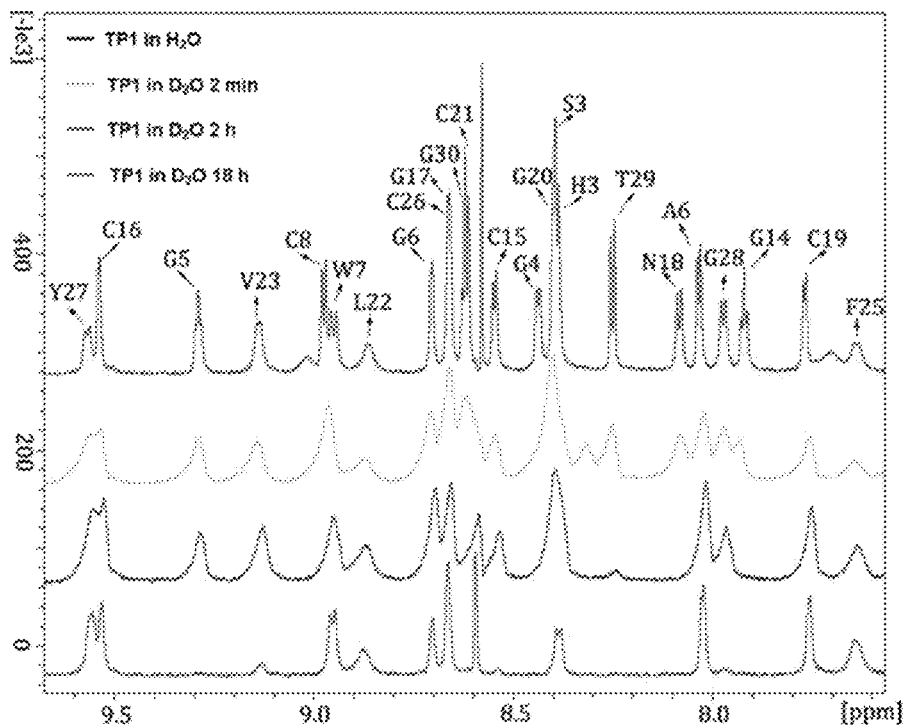
FIG. 33. $D_2O$ exchange of Ginsentide TP1 by 1D NMR.

FIG. 33 shows the slow exchange of D20 indicating that the extensive hydrogen bonding network in ginsentide TP1 to confer their structurally stability.

Example 5. Ginsentides as Anti-Atherosclerotic Agents

The present invention shows that ginsentide TP1 is an endothelial-cell selective adhesion molecule binder that antagonizes monocyte adhesion that can be useful for the management of atherosclerosis. It is five times more potent than known RGD-derived adhesion inhibitor.

Plant peptides and proteins are often underexplored as bioactive constituents in medicinal plants. Unlike other peptides and proteins, multiple intramolecular disulfide bonds stabilize cysteine-rich peptides making them extremely stable against heat, acid and enzymatic degradation. The present invention shows that ginsentide TP1, a cysteine-rich peptide, has eight cysteine residues (four stable disulfide bonds) and a unique pseudo-cyclic structure, making it stable against heat, acid, serum and proteolytic degradation.

Cysteine-rich peptides are highly cross-linked by intramolecular disulfide bridges. This forces the bulky hydrophobic side chains to expose outward, making the surface of the molecule more lipophilic. Also, the slow exchange of D20 indicates that the hydrogen bonding of ginsentides are intramolecularly connected instead of exposing outwards. These characteristics desolvate ginsentides from water. Therefore, the unique features of ginsentides could improve the intrinsic cell permeability and intestinal absorption, making it orally active.

The present invention shows that several ginsentide binds to heparin-affinity column. It is useful for the purification of ginsentides from raw materials.

Identified a new heparin-binding sequence derived from ginsentide that can be useful as a new affinity tag for recombinant expression Technical Description of the Invention Table 1 illustrates the amino acid sequence of ginsentides.

Figure 35:
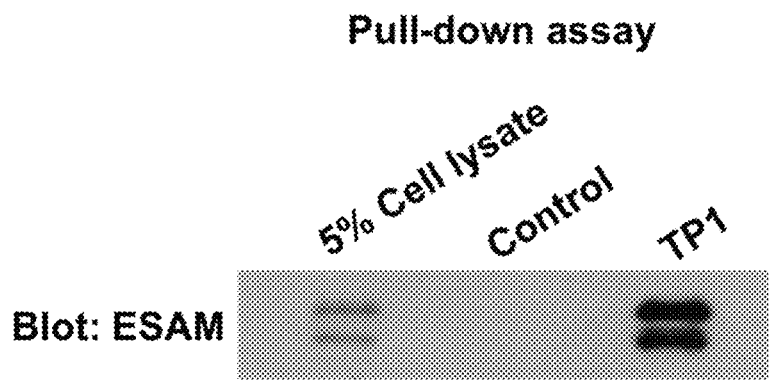
FIG. 35. Pull down assay followed by LC-MS/MS and western blot analysis revealed that ginsentide TP1 interacts with ESAM.

FIG. 35 shows that ginsentide TP1 shows protein-protein interactions with endothelial cell selective adhesion molecules (ESAM). ESAM is involved in the interaction between monocytes and endothelium.

Figure 36:
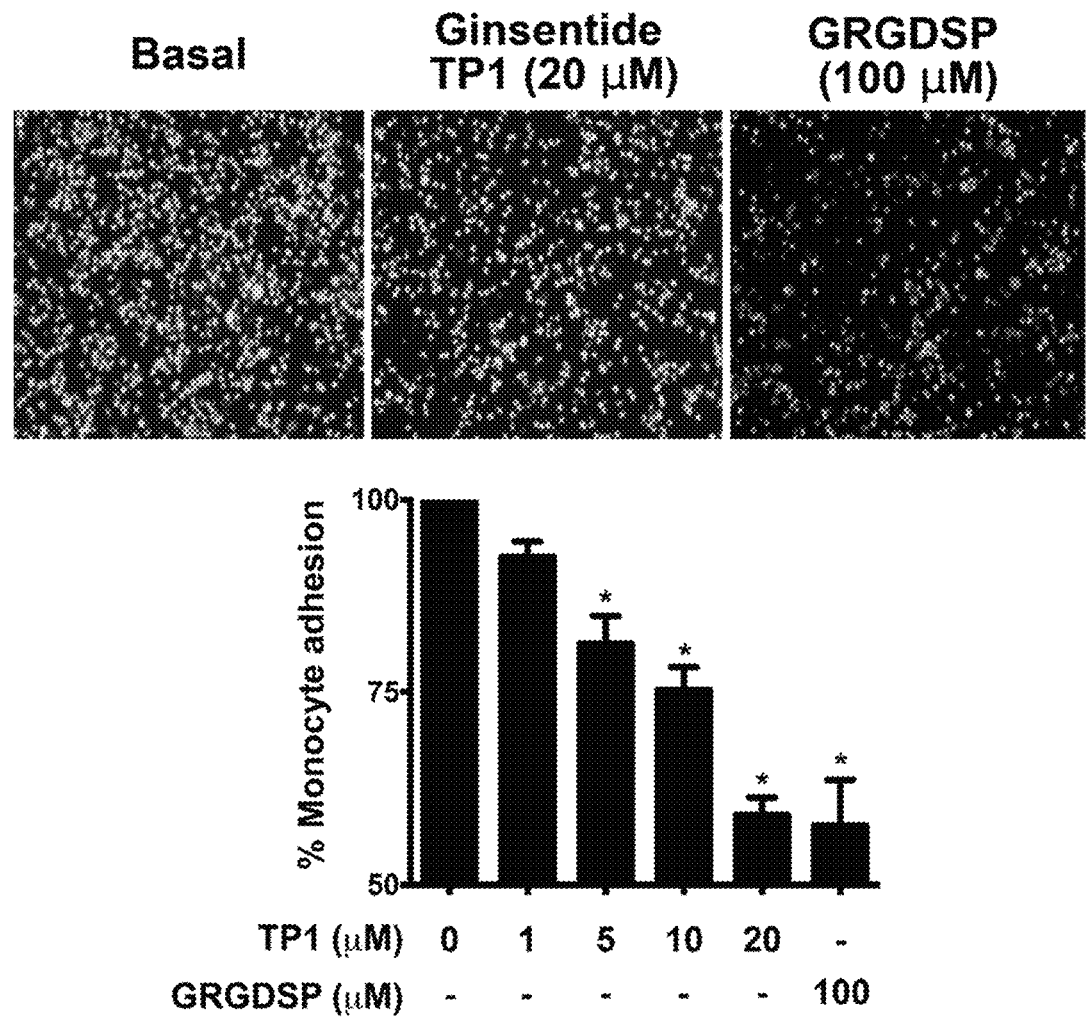
FIG. 36. Ginsentide TP1 inhibited basal monocyte adhesion to endothelium. Ginsentide TP1 was co-incubated with CFSE-labelled THP-1 monocytic cell and HUVEC-CS endothelial monolayer for 1 h. Adhesion inhibitory peptides (GRGDSP) was used as a control.
Figure 37:
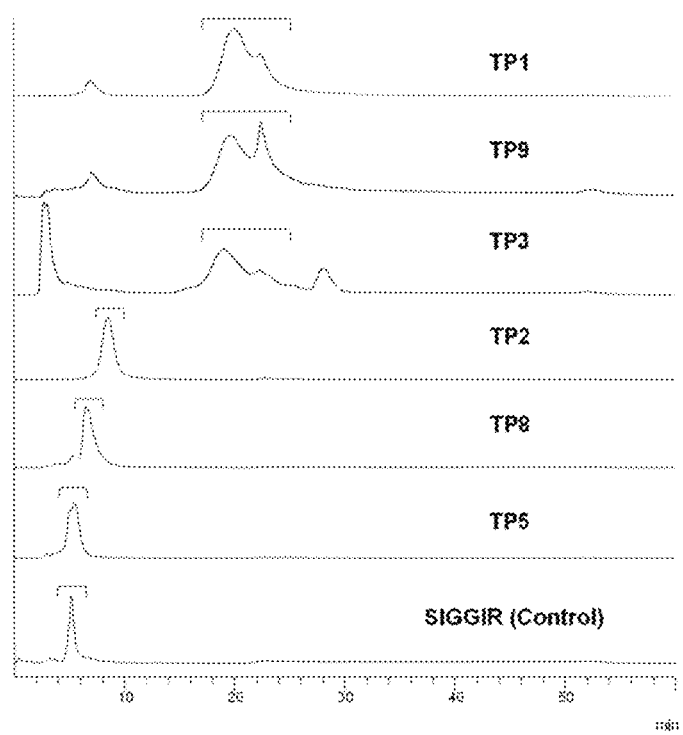
FIG. 37. Heparin-binding properties of ginsentides using heparin HPLC affinity column. Ginsentide TP1, TP3 and TP9 retented in a heparin HPLC affinity column, but not TP2, TP5, TP8 and SIGGIR (negative control).
Figure 38:
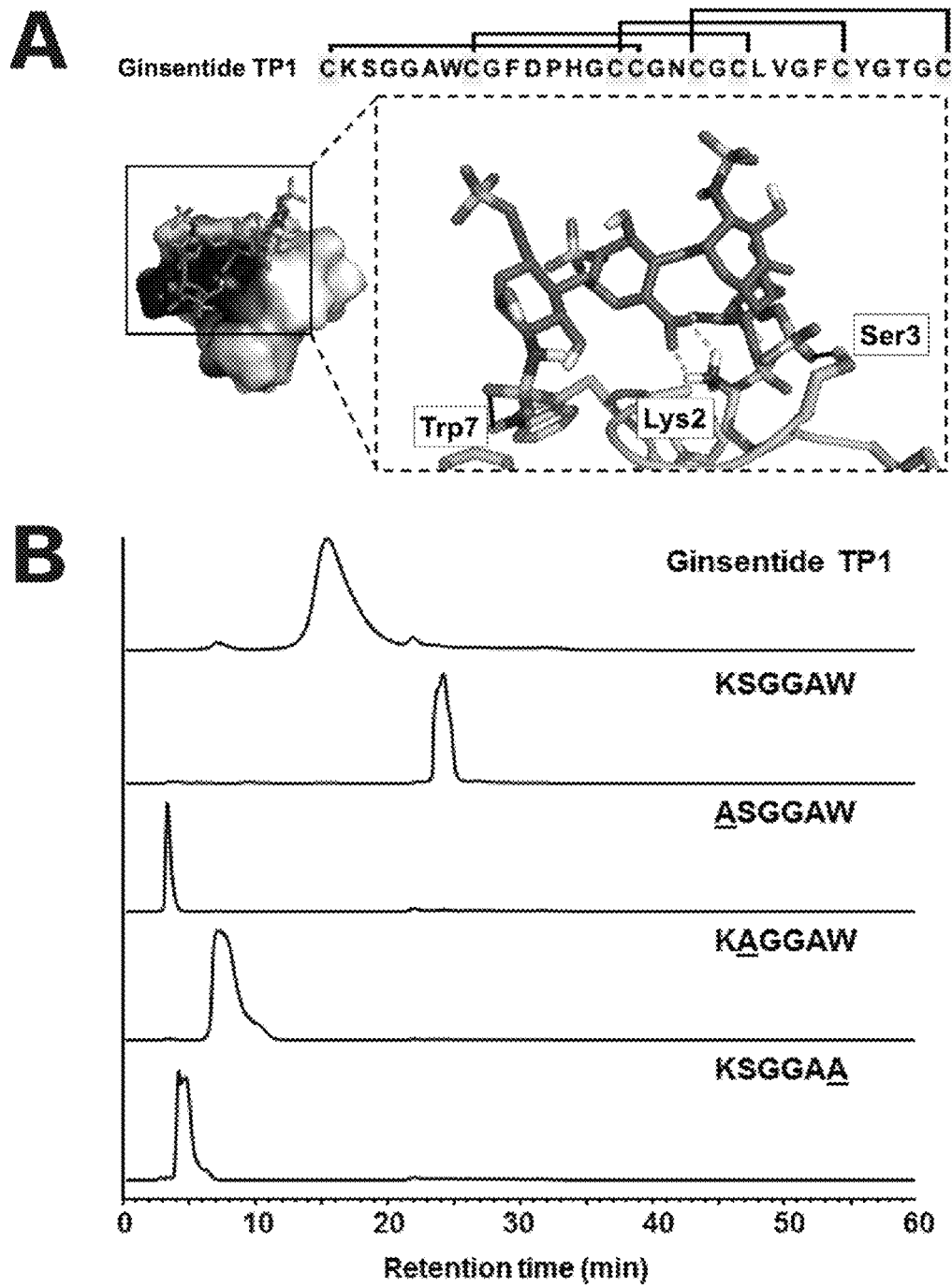
FIG. 38. (A) Modeling the interaction between ginsentide TP1 (SEQ ID NO:1) and heparin sulfate using the ClusPro Version 2.0 server. (B) Comparison of the synthetic peptide Ac-KSGGAW-$NH_2$ (SEQ ID NO:147) and its alanine-substituted analogues (Ac-ASGGAW-$NH_2$ (SEQ ID NO:148), Ac-KAGGAW-$NH_2$ (SEQ ID NO:149) and Ac-KSGGAA-$NH_2$ (SEQ ID NO:150) on heparin binding using heparin HPLC affinity column.

FIG. 36 shows that ginsentide TP1 antagonists monocyte adhesion and is five times more potent than known adhesion inhibitor FIG. 37 shows that several ginsentides are heparin binder and Heparin affinity chromatography can be used for affinity purification FIG. 38 shows the identification of a novel heparin binding sequence from ginsentide TP1. For recombinant expression of proteins, this new sequence can be inserted at the N-terminal or C-terminal to aid heparin affinity purification. For facilitating efficient cellular binding, heparin binding motifs are known to bind to heparan sulfate proteoglycan and form a major part of the extracellular matrix of cells. This new heparin binding motif can be conjugated to other materials to promote their attachment to cell surface. Therefore, this novel heparin binding sequence could be useful in peptide design and engineering to facilitate efficient cellular binding, as well as being a tag for affinity purification in recombinant expression Example 6. Ginsentides as Protective Agents Against Doxorubicin-Induced Cardiotoxicity Currently, four strategies have been applied to prevent the occurrence of DOX-induced cardiotoxicity. But these strategies still have unavoidable drawbacks.

The first strategy is to adjust the administration schedules of DOX. Some studies showed that administration of DOX via prolonged infusion can decrease the cardiotoxicity comparing with bolus administration (LEGHA, S. S., et al. Annals of Internal Medicine, 1982. 96(2): p. 133-139.). Nevertheless, a randomized trial has shown that infusion administration preferentially increases the tendency of developing metastasis in patients (Casper, E. S., et al. Cancer, 1991. 68(6): p. 1221-1229.).

The second approach is to modify the structure of DOX and synthesize analogues. The most common used structural analogs, epirubicin and mitoxantrone, have less cardiotoxicity than DOX, but their chemotherapeutic efficacy are lower than DOX (Lehenbauer Ludke, A. R., et al. Canadian journal of physiology and pharmacology, 2009. 87(10): p. 756-763.)

The third strategy is to develop the drug formulation of DOX to control the peak concentration after administration. Liposomal encapsulation of DOX can extends half-life of DOX and increases accumulation in tumor tissues rat rather than heart owing to its small size, but there still exists a possibility of cardiac dysfunction at high accumulative dosage (Abraham, S. A., et al. Methods in enzymology, 2005. 391: p. 71-97.).

The last scheme to reduce the risk of DOX-induced cardiotoxicity is combination with cardioprotective agents or compounds. However, they either interfere with therapeutic potentials of DOX or may induce secondary malignancies in cancer patients, including dexrazoxane (Tebbi, C. K., et al. Journal of Clinical Oncology, 2007. 25(5): p. 493-500), N-acetylcysteine (Myers, C., et al. Semin Oncol, 1983. 10(Suppl 1): p. 53-55), GSH, co-enzyme Q10, vitamin A and α-tocopherol (Legha, S. S., et al. Annals of the New York Academy of Sciences, 1982. 393(1): p. 411-417.).

Herein, our preliminary results show that ginsentides attenuated DOX-induced cardiotoxicity both in zebrafish model and rat cardiomyocytes. Also, ginsentides have no interference with anticancer capacity of DOX during combinational treatment on breast cancer cells.

Ginsentides, a novel class of cysteine-rich-peptides, are highly resistant to heat, acidic and enzymatic degradation, since they contain 31-33 amino acids with 8 cysteine residues and resemble a pseudo-cyclic cysteine-knot structure. In addition, pharmacokinetic profiles of ginsentides in mice have shown that they are non-toxic, orally bioavailable and relatively stable in blood. These advantages enhance ginsentides as a highly promising adjuvant cardioprotective agent during chemotherapy.

Technical Description of the Invention

The invention provides an approach to prevent DOX-induced cardiotoxicity by a combinational administration of DOX with ginsentides.

(1) Cardioprotection of Ginsentides in Zebrafish

In this invention, a zebrafish transgenic line Tg(cmlc2: gCaMP) (Chi, N.C., et al. PLoS Biol, 2008. 6(5): p. e109.), which expresses a calcium-sensitive green fluorescent protein (GFP) in cardiomyocytes was utilized to visualize and evaluate cardiac functions of zebrafish embryos.

Figure 39:
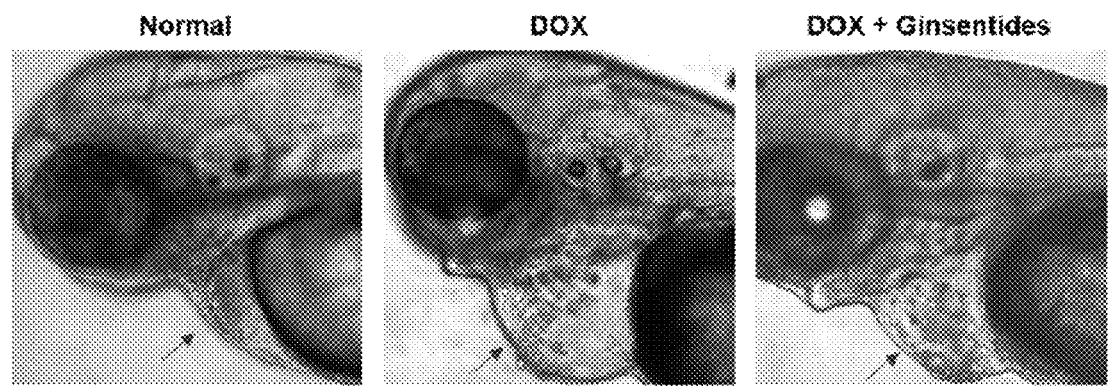
FIG. 39. Representative images of zebrafish embryos after DOX-treatment with or without ginsentide.
Figure 40:
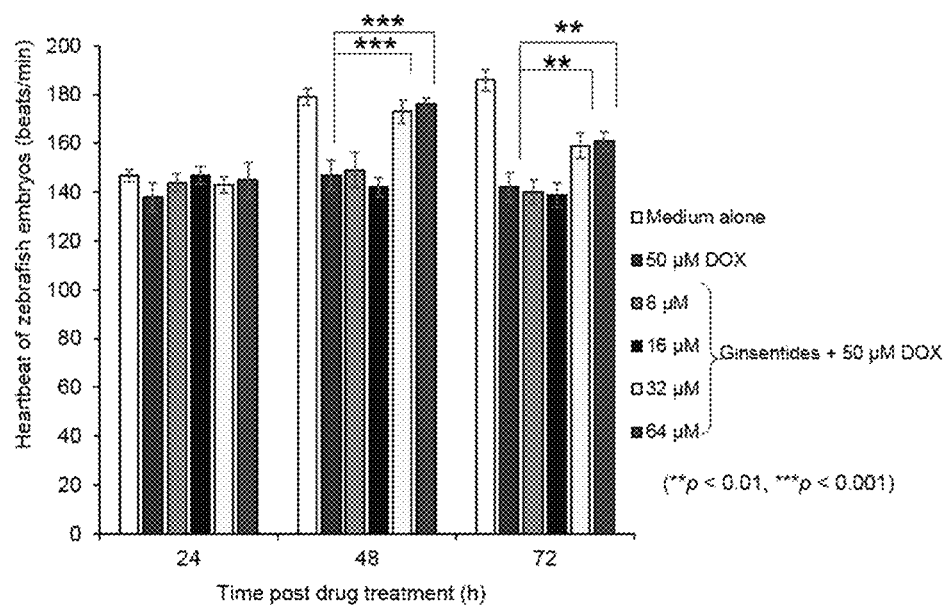
FIG. 40. Heartbeat of zebrafish embryos after ginsentides-treatment.

No adverse effect of ginsentides in zebrafish was found, even applied at high concentrations. The major side effects of DOX-induced cardiotoxicity on zebrafish embryos include (1) reduction of heartbeats, (2) ventricular contractility, and (3) triggering pericardial edema. Addition of ginsentides into DOX-treated zebrafish embryos restored the heartbeat rate near to normal level, and reduced the size of pericardial edema (FIGS. 39 and 40).

Figure 41:
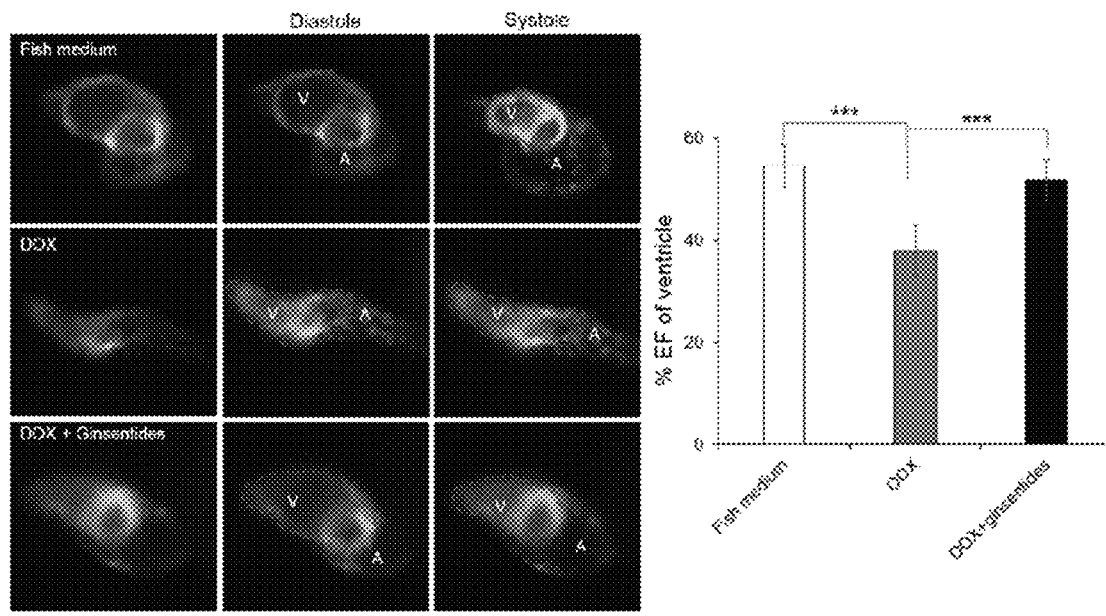
FIG. 41. Comparison of ventricular contractility after co-treatment of DOX with ginsentide.

To evaluate cardiac functions in zebrafish, ejection fraction (EF) were determined by measurement of ventricular volume at the end of systoles and diastoles. EF were markedly reduced after DOX-treatment, but was significantly increased and almost returned to normal after combinational treatment with ginsentides. (FIG. 41), demonstrating significant cardioprotection of ginsentides against DOX-induced cardiotoxicity in zebrafish.

Figure 42:
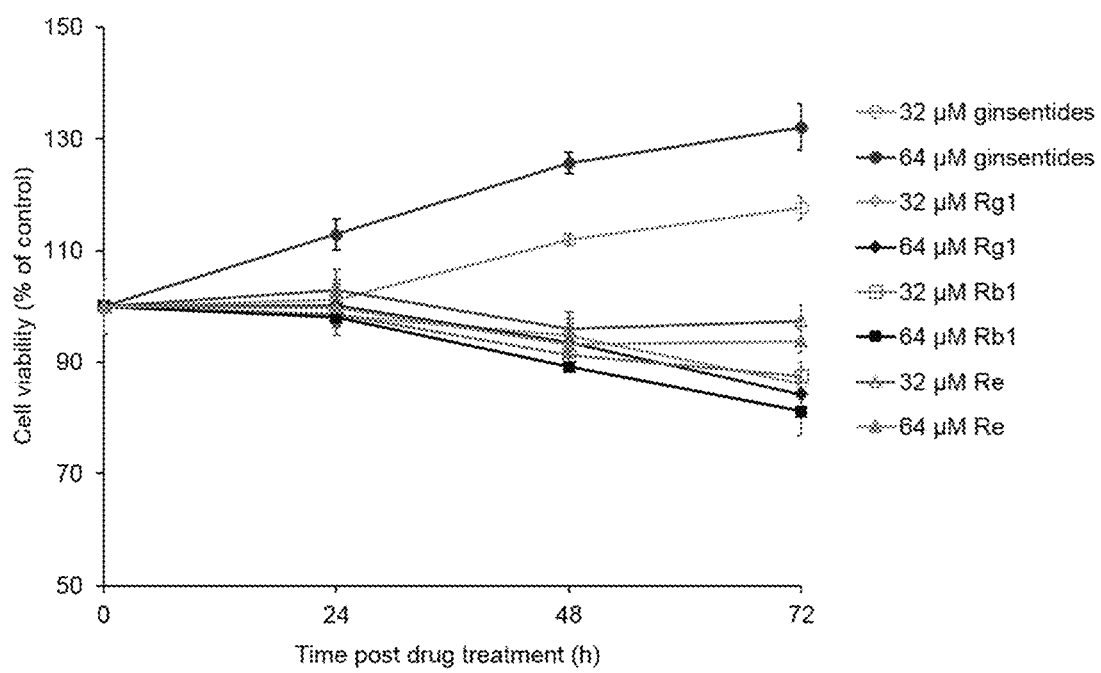
FIG. 42. Cell viability of H9c2 cells after treatment with ginsentides or ginsenosides.

To identify whether ginsentides can attenuate DOX-induced cardiotoxicity in cardiomyocytes, cell viability after drug treatment was measured by MTT assay. The results showed that ginsentides display no apparent toxicity in cardiomyoctes even at high concentration, and enhance the growth of cardiomyocytes compared to major components in *Panax ginseng*, ginsenoside Rg1, Rb1 and Re (FIG. 42).

Figure 43:
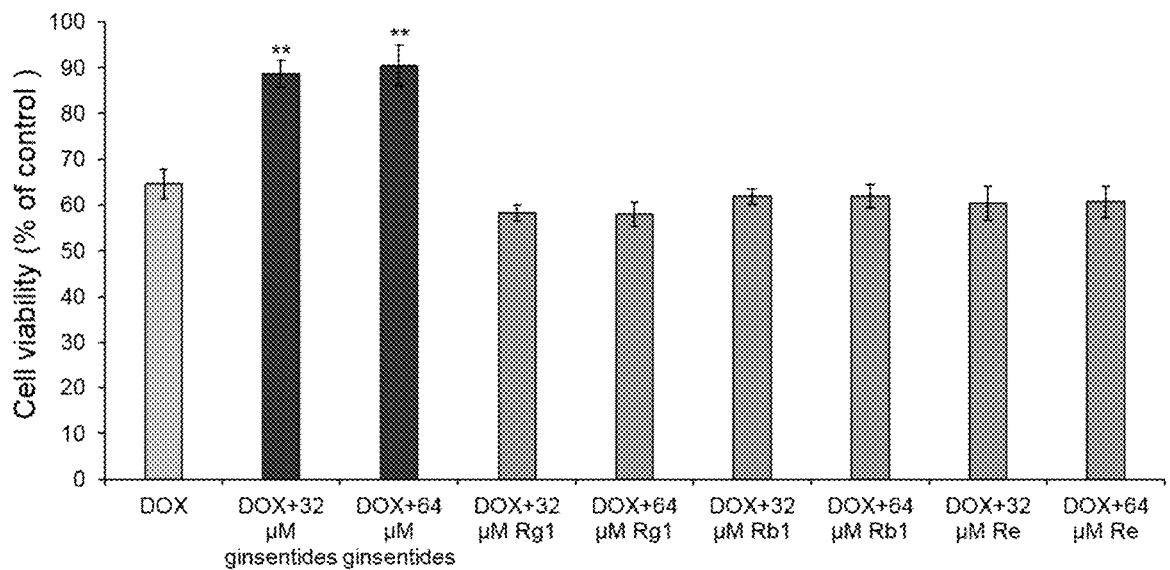
FIG. 43. Cell viability of H9c2 cells after co-treatment of DOX with ginsentides or ginsenosides Rg1, Rb1 and Re.

After 24 h co-treatment of DOX with ginsentides, the viability of H9c2 cells was enhanced by ~20% compared to the DOX-alone treatment (FIG. 43.). But ginsenoside Rg1, Rb1 and Re did not showed any protective effects on cardiomyoctes during DOX-treatment.

(2) No Interference of Anticancer Effects on Breast Cancer Cells

Figure 44:
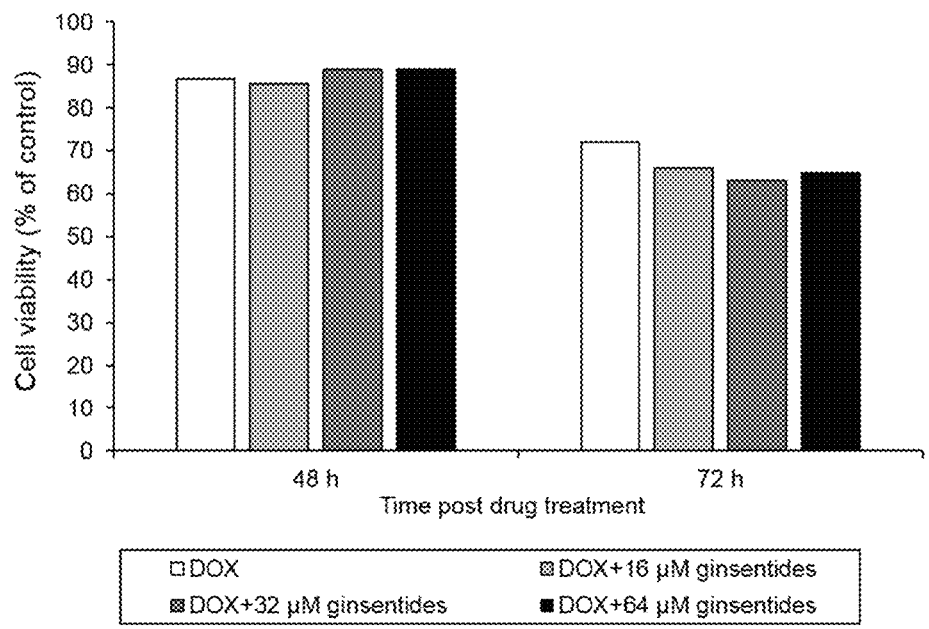
FIG. 44. Effects of ginsentides on cell viability in DOX-treated breast cancer cell line (MDA-MB-231).

Next, we studied whether ginsentides would reduce the anticancer effects of DOX on breast tumor cells. Cell viability of MDA-MB-231 cells was not enhanced after co-treatment of DOX with ginsentides (FIG. 44.). Ginsentides only exerted protective effects on cardiomyocytes and did not interfere with the therapeutic effects of DOX on tumor cells.

(3) Pharmacokinetics of Ginsentides in Mice

Figure 45:
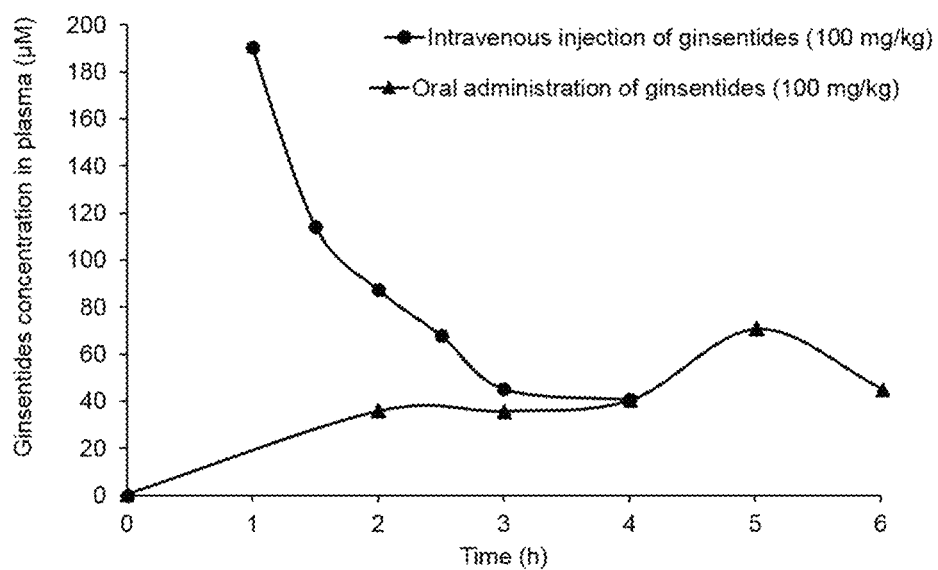
FIG. 45. Plasma concentration of ginsentides after intravenous injection and oral administration in mice.

Pharmacokinetic profiles of ginsentides in mice (FIG. 45.) show that they are orally bioavailable and relatively stable in blood. No discomfort symptoms were observed in mice after receiving ginsentides, and no death occurred during administration and after a month of administration. These advantages provide strong evidence for developing ginsentides as a therapeutic agent in clinical use.

Example 7. Ginsentides as Anti-Ageing and Adaptogenic Agents

Most of the anti-ageing agents are commonly grouped as antioxidant, which reduced oxidative stress and protect the cell from unwanted ageing related process. In this invention, Ginsentide TP1 is disclosed to be an anti-ageing agent, which directly prevents telomere shortening through reducing the level of telomeric repeat-binding factor 2 (TERF2).

Unlike antioxidant anti-ageing compounds, ginsentide TP1 not only prevents oxidative stress induced ageing but also slow down overall ageing process through blocking the telomere shortening process and promote adaptation to stress.

Figure 46:
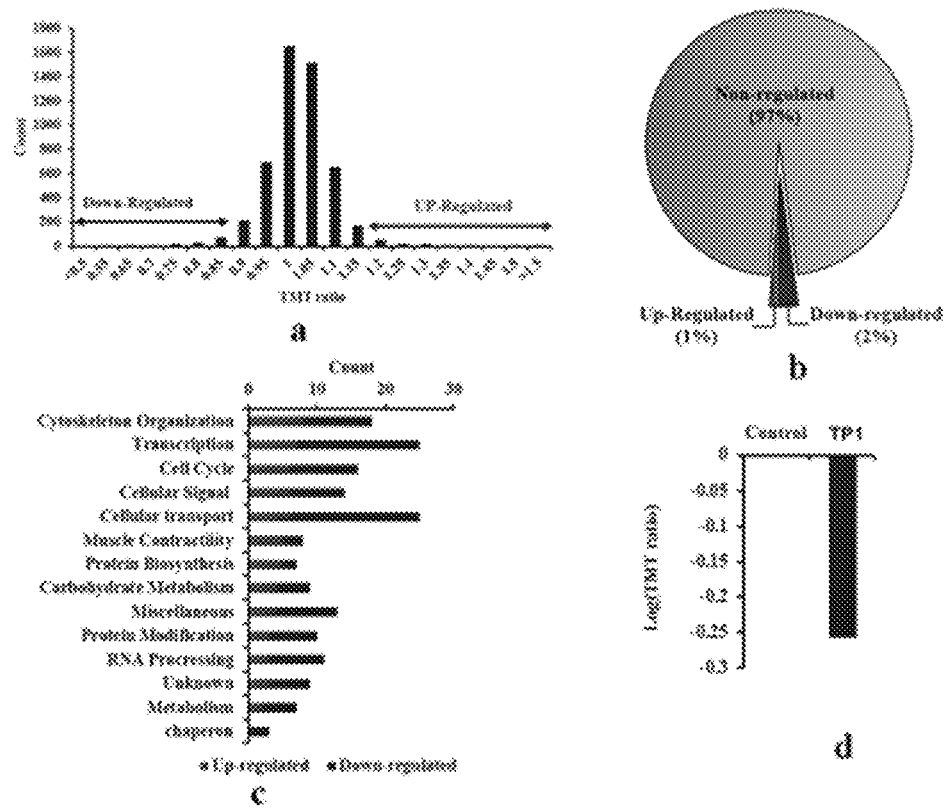
FIG. 46. Effect of ginsentide (TP1) upon HUVEC-CS cellular proteome. Cells were treated with ginsentide and whole cellular proteome was studied through TMT based quantitative proteomic approach. (a) TMT ratio distribution of the invented dataset. (b) Differently expressed proteins in HUVEC-CS cells during ginsentide treatment. (c). Functions classification of differentially regulated proteins upon ginsentide treatment. (d) Relative protein levels of TERF2 after ginsentide treatment.

Unlike conventional peptide drugs, ginsentide TP1 has been proven to be a potential orally active agent due to their excellent stability in both GI tract as well as serum.
Technical Description of the Invention To understand the function of ginsentide TP1 at molecular level, HUVEC-CS cells were treated with 1 µM TP1 for a 30 min period. After termination of the treatment, cells were collected through scraping and washed with ice cold PBS. Cells were lysed in urea lysis buffer (8 M urea in 25 mM TEAB supplemented with protease inhibitor cocktail). Digest 200 µg of protein each using in-solution trypsin digestion technique. Resultant tryptic peptides were labeled with TMT reagents, separated by reverse phase fractionation at high pH (pH~8) and analyzed using nano-HPLC coupled Q-Exactive mass spectrometer. Protein identification and quantification were performed using mascot search engine (version 2.4.1) using UniProtKB human protein database and we identified a total of 5058 proteins with a list of peptides and 1% FDR cutoff. Control condition was used as denominator for TMT based relative protein quantitation. Cutoff values of 0.85 and 1.17 were used as the cutoff level of protein abundance change (FIG. 46a). Using this approach, 62 and 113 proteins were identified as up- and down-regulated in the ginsentide-treated cells (FIG. 46b). The regulated proteins were classified according to their biological functions (FIG. 46c).

Interestingly the level of telomeric repeat-binding factor 2 (TERF2) was significantly decline after 30 min TP1 treatment (FIG. 46d). The reduction of TERF2 by TP1 should slow down the telomere shortening process and prevent cellular ageing. Therefore, ginsentide TP1 prevents the ageing process specifically in vascular cells and maintains the vascular flexibility. It will also reduce other aging related problems.

Figure 47:
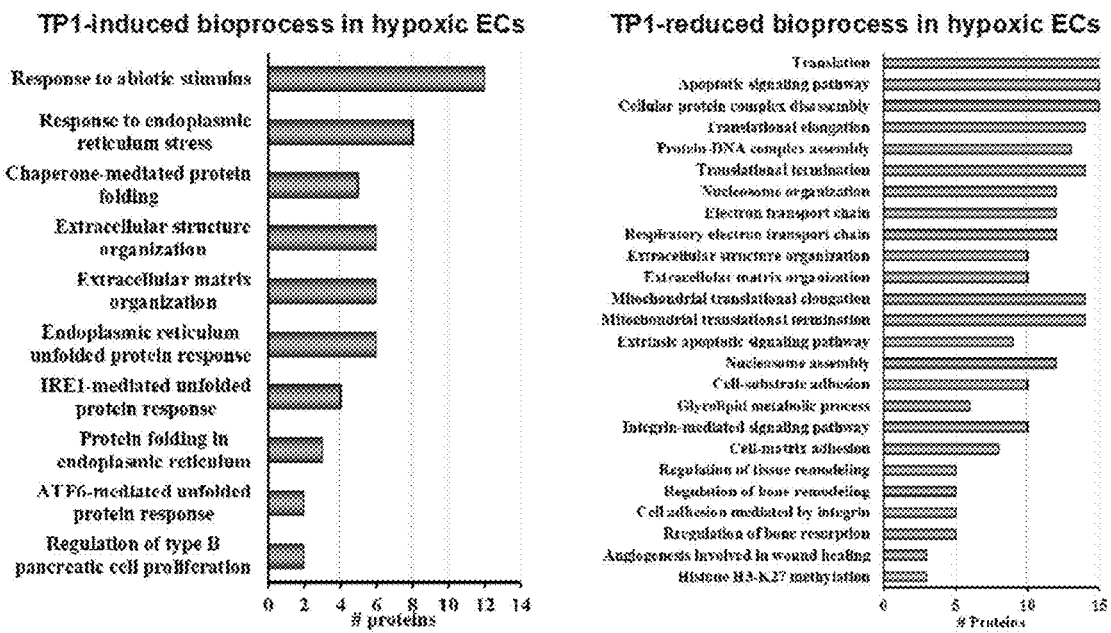
FIG. 47. Effect of ginsentide (TP1) on hypoxic HUVEC-CS cellular proteome.
Figure 48:
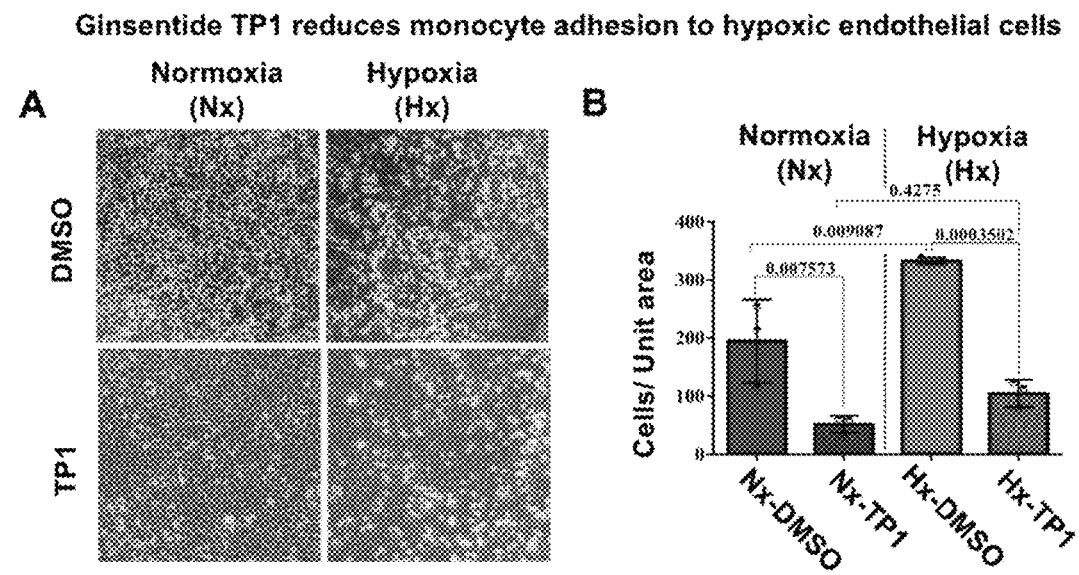
FIG. 48. Effects of ginsentide on leukocyte adhesion to hypoxic endothelial cells.
Figure 49:
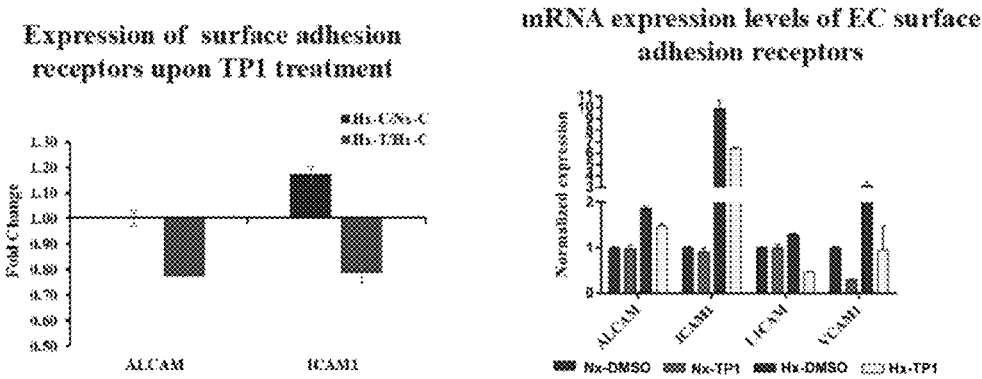
FIG. 49. Effects of ginsentide on hypoxia-induced adhesion molecule expressions in endothelial cells.
Figure 50:
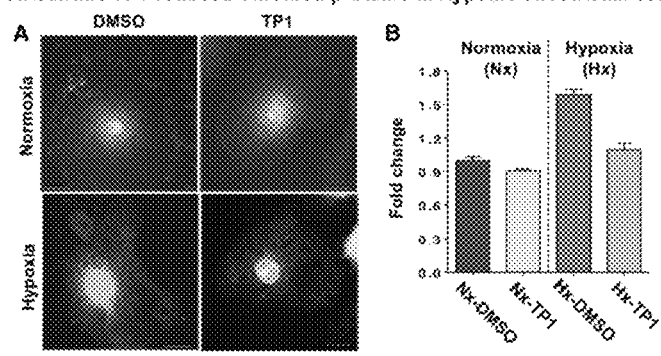
FIG. 50. Effects of ginsentide on the accumulation of unfolded protein in hypoxic endothelial cells.
Figure 51:
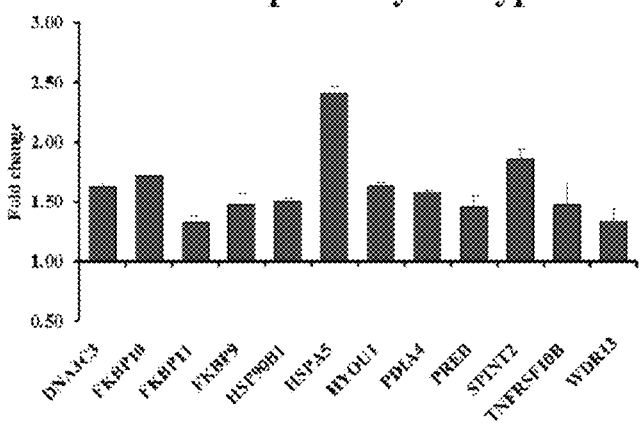
FIG. 51. Effects of ginsentide on the unfolded protein response pathway in hypoxic endothelial cells.
Figure 52:
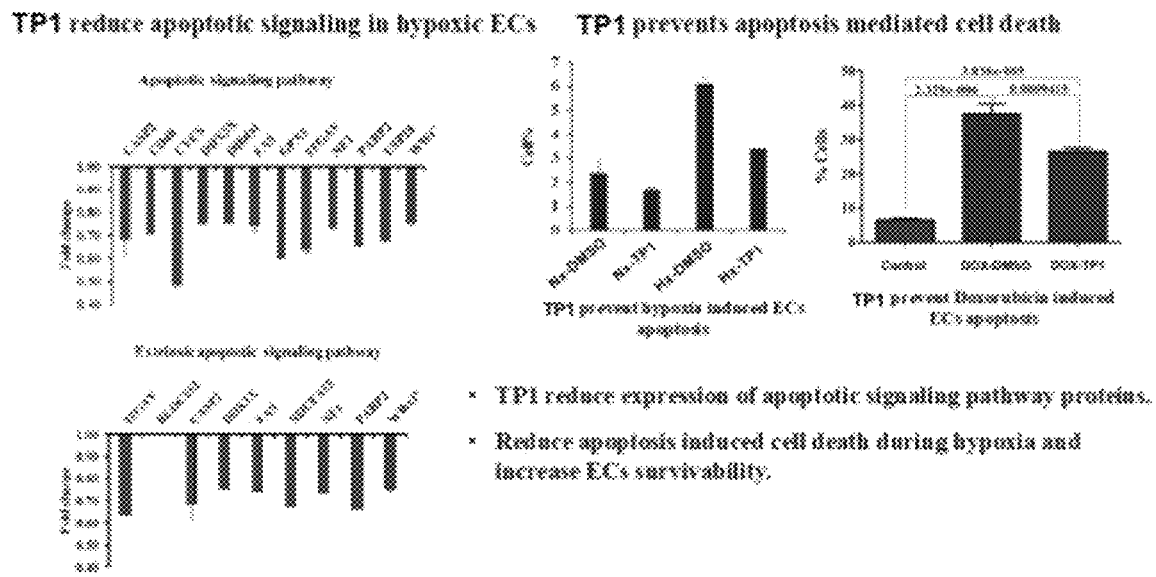
FIG. 52. Effects of ginsentide on apoptosis pathway in endothelial cells.
Figure 53:
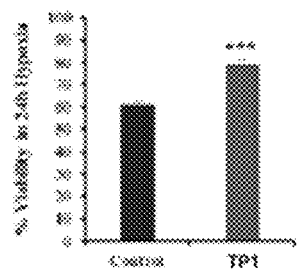
FIG. 53. Effects of ginsentides on the survivability of hypoxic endothelial cells.

FIG. 47 shows the effects of ginsentide TP1 on hypoxic endothelial cell proteome. Ginsentide TP1 induced unfolded protein response pathways in hypoxic endothelial cells. It also reduces apoptosis signaling pathways and reduced cell adhesion pathways.

FIG. 48-53 shows that ginsentide TP1 promotes adaptation of endothelials cells to hypoxic stress.

Figure 54:
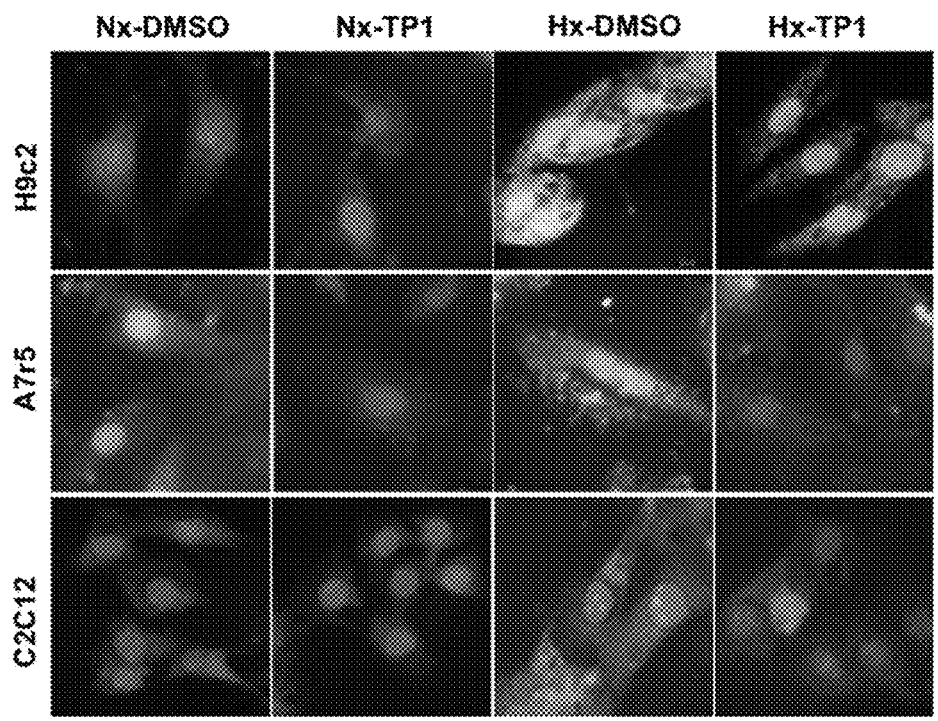
FIG. 54. Ginsentides reduced unfolded proteins in cardiomyocyte, vascular smooth muscle cells, and myocytes.

FIG. 54. Ginsentides reduced unfolded proteins in cardiomyocyte, vascular smooth muscle cells, and myocytes.

Figure 55:
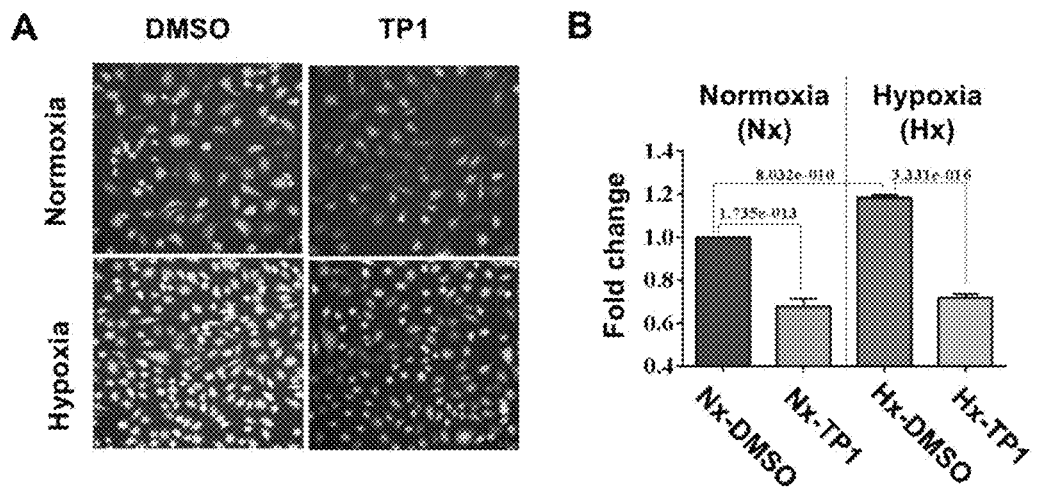
FIG. 55. Ginsentides reduced reactive oxygen species production in hypoxic endothelial cells.

FIG. 55. Ginsentides reduced reactive oxygen species production in hypoxic endothelial cells.

Figure 56:
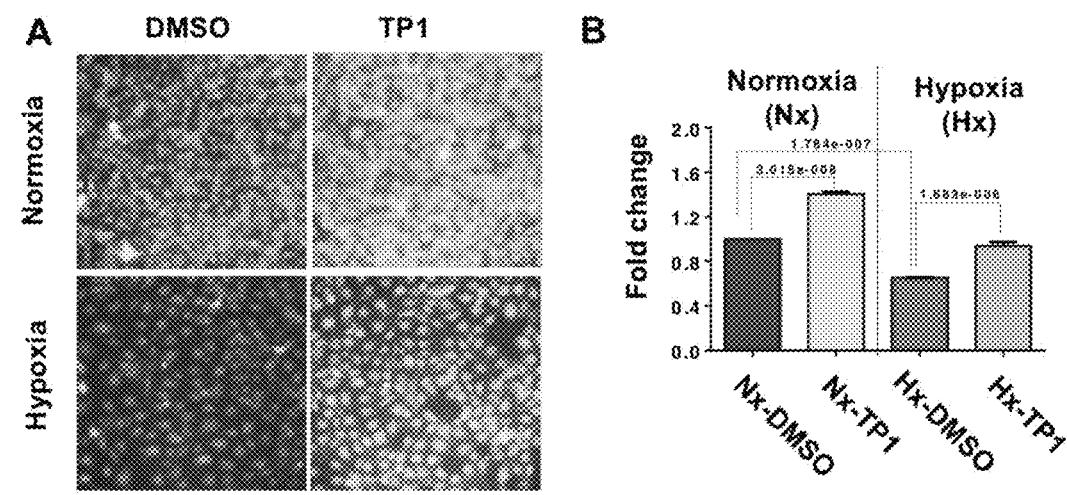
FIG. 56. Ginsentides increased nitric oxide production in hypoxic endothelial cells.
Figure 57:
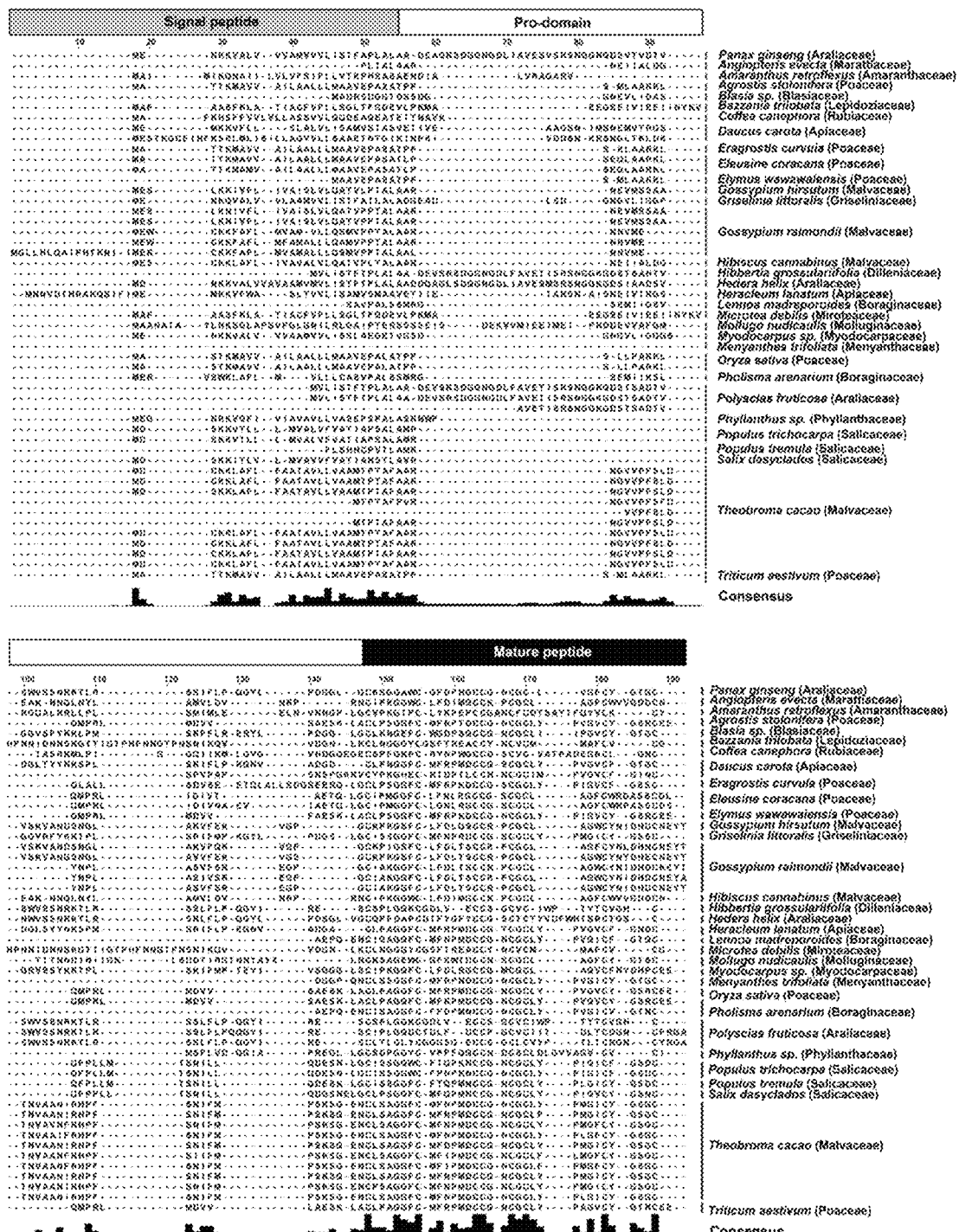
FIG. 57. Ginsentide-like precursor sequences from NCBI and OneKp transcriptome database. The amino acid sequences are set forth in SEQ ID NOs:151-200.

FIG. 56. Ginsentides increased nitric oxide production in hypoxic endothelial cells.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A method of treating anxiety in a subject in need thereof, the method comprising administering to the subject a pharmaceutical composition comprising a ginsentide or ginsentide-like peptide or a pharmaceutically acceptable salt, said ginsentide or ginsentide-like peptide having the amino acid sequence set forth in any one of SEQ ID NO:1-14.

2. The method of claim 1, wherein the ginsentide or ginsentide-like peptide has an amino acid sequence set forth is any one of SEQ ID NO:1, 3 or 8.

* * * * *

SEQUENCE LISTING

<160> NUMBER OF SEQ ID NOS: 200

<210> SEQ ID NO 1
<211> LENGTH: 31
<212> TYPE: PRT
<213> ORGANISM: Panax ginseng

<400> SEQUENCE: 1

Cys Lys Ser Gly Gly Ala Trp Cys Gly Phe Asp Pro His Gly Cys Cys
1               5                   10                  15

Gly Asn Cys Gly Cys Leu Val Gly Phe Cys Tyr Gly Thr Gly Cys
            20                  25                  30

<210> SEQ ID NO 2
<211> LENGTH: 31
<212> TYPE: PRT
<213> ORGANISM: Panax ginseng

<400> SEQUENCE: 2

Cys Lys Ser Ser Gly Ala Trp Cys Gly Phe Asp Pro His Gly Cys Cys
1               5                   10                  15

Gly Asn Cys Gly Cys Leu Val Gly Phe Cys Tyr Gly Thr Gly Cys
            20                  25                  30

<210> SEQ ID NO 3
<211> LENGTH: 31
<212> TYPE: PRT
<213> ORGANISM: Panax ginseng

<400> SEQUENCE: 3

Cys Lys Ser Ala Gly Thr Trp Cys Gly Phe Asp Pro His Gly Cys Cys
1               5                   10                  15

Gly Ser Cys Gly Cys Leu Val Gly Phe Cys Tyr Gly Val Ser Cys
            20                  25                  30

<210> SEQ ID NO 4
<211> LENGTH: 33
<212> TYPE: PRT
<213> ORGANISM: Panax ginseng

<400> SEQUENCE: 4

Cys Leu Lys Asn Gly Glu Phe Cys Trp Gly Asp Pro Ser Gly Cys Cys
1               5                   10                  15

Gly Asn Cys Gly Cys Leu Ile Ile Pro Gly Val Cys Tyr Gly Thr Gly
            20                  25                  30

Cys

<210> SEQ ID NO 5
<211> LENGTH: 31
<212> TYPE: PRT
<213> ORGANISM: Panax ginseng

<400> SEQUENCE: 5

Cys Lys Ser Ser Gly Ala Trp Cys Gly Phe Asp Pro His Gly Cys Cys
1               5                   10                  15

Gly Asn Cys Gly Cys Leu Val Gly Phe Cys Tyr Gly Thr Asp Cys
            20                  25                  30

<210> SEQ ID NO 6
<211> LENGTH: 31
<212> TYPE: PRT
<213> ORGANISM: Panax ginseng

<400> SEQUENCE: 6

Cys Ile Pro Gly Gly Gly Phe Cys Met Phe Glu Pro Leu Ser Cys Cys
1               5                   10                  15

Val Asn Cys Gly Cys Ile Leu Val Pro Gly Val Cys Tyr Cys Gly
            20                  25                  30

<210> SEQ ID NO 7
<211> LENGTH: 31
<212> TYPE: PRT
<213> ORGANISM: Panax ginseng

<400> SEQUENCE: 7

```
Cys Lys Ser Gly Gly Thr Trp Cys Gly Phe Asp Pro His Gly Cys Cys
1               5                   10                  15

Gly Asn Cys Gly Cys Leu Val Gly Phe Cys Tyr Gly Thr Gly Cys
            20                  25                  30
```

<210> SEQ ID NO 8
<211> LENGTH: 31
<212> TYPE: PRT
<213> ORGANISM: Panax quinquefolius

<400> SEQUENCE: 8

```
Cys Ile Ser Ser Gly Gly Trp Cys Gly Phe Asp Leu His Gly Cys Cys
1               5                   10                  15

Gly Asn Cys Gly Cys Leu Val Gly Phe Cys Tyr Gly Thr Gly Cys
            20                  25                  30
```

<210> SEQ ID NO 9
<211> LENGTH: 31
<212> TYPE: PRT
<213> ORGANISM: Panax quinquefolius

<400> SEQUENCE: 9

```
Cys Lys Ser Gly Gly Ser Trp Cys Gly Phe Asp Pro His Gly Cys Cys
1               5                   10                  15

Gly Asn Cys Gly Cys Leu Val Gly Phe Cys Tyr Gly Thr Gly Cys
            20                  25                  30
```

<210> SEQ ID NO 10
<211> LENGTH: 31
<212> TYPE: PRT
<213> ORGANISM: Panax quinquefolius

<400> SEQUENCE: 10

```
Cys Ile Phe Ser Gly Gly Trp Cys Gly Phe Asp Leu His Gly Cys Cys
1               5                   10                  15

Gly Asn Cys Gly Cys Leu Val Gly Phe Cys Tyr Gly Thr Gly Cys
            20                  25                  30
```

<210> SEQ ID NO 11
<211> LENGTH: 33
<212> TYPE: PRT
<213> ORGANISM: Panax quinquefolius

<400> SEQUENCE: 11

```
Cys Leu Lys Asn Gly Gln Phe Cys Trp Gly Asn Pro Ser Gly Cys Cys
1               5                   10                  15

Gly Asn Cys Gly Cys Leu Ile Ile Pro Gly Val Cys Tyr Gly Thr Gly
            20                  25                  30

Cys
```

<210> SEQ ID NO 12
<211> LENGTH: 31
<212> TYPE: PRT
<213> ORGANISM: Panax quinquefolius -continued

```
<400> SEQUENCE: 12

Cys Ile Pro Gly Gly Gly Phe Cys Met Phe Glu Pro Leu Ser Cys Cys
1               5                   10                  15

His Asn Cys Gly Cys Leu Leu Val Pro Gly Val Cys Tyr Cys Gly
            20                  25                  30

<210> SEQ ID NO 13
<211> LENGTH: 31
<212> TYPE: PRT
<213> ORGANISM: Panax notoginseng

<400> SEQUENCE: 13

Cys Ile Pro Asn Gly Gly Phe Cys Met Phe Glu Pro Leu Ser Cys Cys
1               5                   10                  15

Val Asn Cys Gly Cys Ile Leu Val Pro Gly Val Cys Tyr Cys Gly
            20                  25                  30

<210> SEQ ID NO 14
<211> LENGTH: 32
<212> TYPE: PRT
<213> ORGANISM: Panax quinquefolius

<400> SEQUENCE: 14

Cys Leu Lys Val Gly Lys Ile Cys Leu Gly Arg Gly Leu Lys Glu Cys
1               5                   10                  15

Cys Pro Ser Ala Thr Cys Gly Cys Leu Leu Gly Phe Cys Ile Lys Cys
            20                  25                  30

<210> SEQ ID NO 15
<211> LENGTH: 34
<212> TYPE: PRT
<213> ORGANISM: Angiopteris evecta

<400> SEQUENCE: 15

Cys Ile Pro Lys Gly Gly Trp Cys Leu Phe Asp Ile Met Gly Cys Cys
1               5                   10                  15

Lys Pro Cys Gly Cys Leu Ala Gly Phe Cys Trp Val Val Gly Asp Asp
            20                  25                  30

Cys Asn

<210> SEQ ID NO 16
<211> LENGTH: 36
<212> TYPE: PRT
<213> ORGANISM: Amaranthus retroflexus

<400> SEQUENCE: 16

Cys Val Pro Lys Gly Thr Pro Cys Leu Tyr Lys Pro Glu Pro Cys Cys
1               5                   10                  15

Gly Ala Asn Cys Phe Cys Asp Thr Ser Ala Tyr Thr Phe Gln Tyr Val
            20                  25                  30

Cys Lys Cys Tyr
        35

<210> SEQ ID NO 17
<211> LENGTH: 35
<212> TYPE: PRT
<213> ORGANISM: Agrostis stolonifera

<400> SEQUENCE: 17

Cys Leu Pro Ser Gly Gly Phe Cys Met Phe Arg Pro Thr Asp Cys Cys
1               5                   10                  15
```

```
Gly Asn Cys Gly Cys Leu Tyr Pro Val Gly Val Cys Tyr Gly Ser Arg
            20                  25                  30

Cys Glu Glu
        35

<210> SEQ ID NO 18
<211> LENGTH: 33
<212> TYPE: PRT
<213> ORGANISM: Blasia sp.

<400> SEQUENCE: 18

Cys Leu Lys Asn Gly Glu Phe Cys Trp Gly Asp Pro Ser Gly Cys Cys
1               5                  10                  15

Gly Asn Cys Gly Cys Leu Ile Ile Pro Gly Val Cys Tyr Gly Thr Gly
            20                  25                  30

Cys

<210> SEQ ID NO 19
<211> LENGTH: 30
<212> TYPE: PRT
<213> ORGANISM: Bazzania trilobata

<400> SEQUENCE: 19

Cys Leu Asn Gly Gly Tyr Cys Gly Ser Phe Thr Arg Glu Ala Cys
1               5                  10                  15

Cys Tyr Asn Cys Val Cys Met Met Ala Phe Cys Val Cys Gly
            20                  25                  30

<210> SEQ ID NO 20
<211> LENGTH: 35
<212> TYPE: PRT
<213> ORGANISM: Coffea canephora

<400> SEQUENCE: 20

Cys Ser Pro Phe Gly Lys Pro Cys Arg Tyr Asn Pro Trp Gly Cys Cys
1               5                  10                  15

Asp Ser Cys Val Cys Val Ala Thr Pro Ala Asp Glu Gly Arg Cys Leu
            20                  25                  30

Gly Asn Cys
        35

<210> SEQ ID NO 21
<211> LENGTH: 33
<212> TYPE: PRT
<213> ORGANISM: Daucus carota

<400> SEQUENCE: 21

Cys Leu Pro Asn Gly Gly Phe Cys Met Phe Arg Pro Met Asp Cys Cys
1               5                  10                  15

Gly Ser Cys Gly Cys Leu Tyr Pro Val Gly Val Cys Phe Gly Thr Gly
            20                  25                  30

Cys

<210> SEQ ID NO 22
<211> LENGTH: 33
<212> TYPE: PRT
<213> ORGANISM: Daucus carota

<400> SEQUENCE: 22

Cys Tyr Pro Lys Gly His Glu Cys Arg Thr Asp Pro Thr Leu Cys Cys
```

```
1               5                   10                  15
His Asn Cys Gly Cys Ile Met Pro Val Gly Val Cys Phe Gly Ile Asn
            20                  25                  30

Cys

<210> SEQ ID NO 23
<211> LENGTH: 33
<212> TYPE: PRT
<213> ORGANISM: Eragrostis curvula

<400> SEQUENCE: 23

Cys Leu Pro Ser Gly Gly Phe Cys Met Phe Arg Pro Lys Asp Cys Cys
1               5                   10                  15

Gly Ser Cys Gly Cys Leu Tyr Pro Ile Gly Val Cys Phe Gly Ser Ser
            20                  25                  30

Cys

<210> SEQ ID NO 24
<211> LENGTH: 35
<212> TYPE: PRT
<213> ORGANISM: Eleusine coracana

<400> SEQUENCE: 24

Cys Ile Pro Met Gly Gly Phe Cys Leu Phe Asn Leu Arg Gly Cys Cys
1               5                   10                  15

Gly Ser Cys Gly Cys Leu Ala Gly Phe Cys Trp Arg Asp Ala Ser Ser
            20                  25                  30

Cys Asp Leu
        35

<210> SEQ ID NO 25
<211> LENGTH: 35
<212> TYPE: PRT
<213> ORGANISM: Eleusine coracana

<400> SEQUENCE: 25

Cys Ile Pro Met Gly Gly Phe Cys Leu Gly Asn Leu Arg Gly Cys Cys
1               5                   10                  15

Gly Ser Cys Gly Cys Leu Ala Gly Phe Cys Trp Arg Pro Ala Ser Ser
            20                  25                  30

Cys Asp Ser
        35

<210> SEQ ID NO 26
<211> LENGTH: 35
<212> TYPE: PRT
<213> ORGANISM: Elymus wawawaiensis

<400> SEQUENCE: 26

Cys Leu Pro Ser Gly Gly Phe Cys Met Phe Arg Pro Lys Asp Cys Cys
1               5                   10                  15

Gly Asn Cys Gly Cys Leu Tyr Pro Ile Gly Val Cys Tyr Gly Ser Arg
            20                  25                  30

Cys Glu Glu
        35

<210> SEQ ID NO 27
<211> LENGTH: 37
<212> TYPE: PRT
<213> ORGANISM: Gossypium hirsutum
```

```
<400> SEQUENCE: 27

Cys Lys Pro Lys Gly Ser Phe Cys Leu Phe Asp Leu Gln Ser Cys Cys
1               5                   10                  15

Arg Pro Cys Gly Cys Leu Ala Gly Trp Cys Tyr Asn Ile Asp His Asp
            20                  25                  30

Cys Asn Glu Tyr Thr
            35

<210> SEQ ID NO 28
<211> LENGTH: 33
<212> TYPE: PRT
<213> ORGANISM: Griselinia littoralis

<400> SEQUENCE: 28

Cys Ile Ser Ser Gly Gly Phe Cys Met Phe Asn Pro Arg Asp Cys Cys
1               5                   10                  15

Gly Ser Cys Gly Cys Leu Tyr Pro Met Gly Ile Cys Tyr Gly Ser Ser
            20                  25                  30

Cys

<210> SEQ ID NO 29
<211> LENGTH: 37
<212> TYPE: PRT
<213> ORGANISM: Gossypium raimondii

<400> SEQUENCE: 29

Cys Lys Pro Ile Gly Ser Phe Cys Leu Phe Asp Leu Thr Ser Cys Cys
1               5                   10                  15

Arg Pro Cys Gly Cys Leu Ala Gly Phe Cys Tyr Asn Leu Asp His Asn
            20                  25                  30

Cys Asn Glu Tyr Thr
            35

<210> SEQ ID NO 30
<211> LENGTH: 37
<212> TYPE: PRT
<213> ORGANISM: Gossypium raimondii

<400> SEQUENCE: 30

Cys Lys Pro Lys Gly Ser Phe Cys Leu Phe Asp Leu Thr Ser Cys Cys
1               5                   10                  15

Arg Pro Cys Gly Cys Leu Ala Gly Trp Cys Tyr Asn Tyr Asp His Glu
            20                  25                  30

Cys Asn Glu Tyr Thr
            35

<210> SEQ ID NO 31
<211> LENGTH: 37
<212> TYPE: PRT
<213> ORGANISM: Gossypium raimondii

<400> SEQUENCE: 31

Cys Ile Ala Lys Gly Gly Phe Cys Leu Phe Asp Leu Thr Ser Cys Cys
1               5                   10                  15

Arg Pro Cys Gly Cys Leu Ala Gly Trp Cys Tyr Asn Ile Asp His Asp
            20                  25                  30

Cys Lys Glu Tyr Thr
            35
```

<210> SEQ ID NO 32
<211> LENGTH: 37
<212> TYPE: PRT
<213> ORGANISM: Gossypium raimondii

<400> SEQUENCE: 32

Cys Ile Ala Lys Gly Gly Phe Cys Leu Phe Asp Leu Thr Ser Cys Cys
1               5                   10                  15

Arg Pro Cys Gly Cys Leu Ala Gly Trp Cys Tyr Asn Ile Asp His Asp
            20                  25                  30

Cys Asn Glu Tyr Ala
        35

<210> SEQ ID NO 33
<211> LENGTH: 37
<212> TYPE: PRT
<213> ORGANISM: Gossypium raimondii

<400> SEQUENCE: 33

Cys Ile Ala Lys Gly Gly Phe Cys Leu Phe Asp Leu Thr Ser Cys Cys
1               5                   10                  15

Arg Pro Cys Gly Cys Leu Ala Gly Trp Cys Tyr Asn Ile Asp His Asp
            20                  25                  30

Cys Asn Glu Tyr Thr
        35

<210> SEQ ID NO 34
<211> LENGTH: 34
<212> TYPE: PRT
<213> ORGANISM: Hibiscus cannabinus

<400> SEQUENCE: 34

Cys Ile Pro Lys Gly Gly Trp Cys Leu Phe Asp Ile Met Gly Cys Cys
1               5                   10                  15

Lys Pro Cys Gly Cys Leu Ala Gly Phe Cys Trp Val Val Gly Asp Asp
            20                  25                  30

Cys Asn

<210> SEQ ID NO 35
<211> LENGTH: 31
<212> TYPE: PRT
<213> ORGANISM: Hibbertia grossulariifolia

<400> SEQUENCE: 35

Cys Ser Pro Leu Gly Gly Lys Cys Gly Asp Leu Val Glu Cys Cys Ser
1               5                   10                  15

Gly Cys Val Cys Ile Trp Pro Thr Tyr Thr Cys Val Gly His Cys
            20                  25                  30

<210> SEQ ID NO 36
<211> LENGTH: 37
<212> TYPE: PRT
<213> ORGANISM: Hedera helix

<400> SEQUENCE: 36

Cys Gln Pro Phe Asp Ala Pro Cys Asp Thr Phe Tyr Gly Phe Tyr Cys
1               5                   10                  15

Cys Gly Ser Cys Thr Cys Thr Tyr Val Asp Phe Trp His Thr Ser Arg
            20                  25                  30

Cys Thr Gly Ser Cys

-continued

```
<210> SEQ ID NO 37
<211> LENGTH: 33
<212> TYPE: PRT
<213> ORGANISM: Heracleum lanatum

<400> SEQUENCE: 37

Cys Leu Pro Ala Gly Gly Phe Cys Met Phe Arg Pro Met Asp Cys Cys
1               5                   10                  15

Gly Thr Cys Gly Cys Leu Tyr Pro Val Gly Val Cys Phe Gly Asn Asp
            20                  25                  30

Cys

<210> SEQ ID NO 38
<211> LENGTH: 33
<212> TYPE: PRT
<213> ORGANISM: Lennoa madreporoides

<400> SEQUENCE: 38

Cys Ile Gly Ala Gly Gly Phe Cys Met Phe Asn Pro Met Asp Cys Cys
1               5                   10                  15

Gly Asn Cys Gly Cys Leu Tyr Pro Val Gly Ile Cys Phe Gly Thr Gly
            20                  25                  30

Cys

<210> SEQ ID NO 39
<211> LENGTH: 30
<212> TYPE: PRT
<213> ORGANISM: Microtea madreporoides

<400> SEQUENCE: 39

Cys Leu Asn Gly Gly Gly Tyr Cys Gly Ser Phe Thr Arg Glu Ala Cys
1               5                   10                  15

Cys Tyr Asn Cys Val Cys Met Met Ala Phe Cys Val Cys Gly
            20                  25                  30

<210> SEQ ID NO 40
<211> LENGTH: 31
<212> TYPE: PRT
<213> ORGANISM: Mollugo nudicaulis

<400> SEQUENCE: 40

Cys Lys Ser Ala Gly Glu Trp Cys Gly Phe Ser Trp Thr Asp Cys Cys
1               5                   10                  15

Asn Ser Cys Gly Cys Leu Ala Gly Phe Cys Tyr Gly Thr Ser Cys
            20                  25                  30

<210> SEQ ID NO 41
<211> LENGTH: 35
<212> TYPE: PRT
<213> ORGANISM: Myodocarpus sp.

<400> SEQUENCE: 41

Cys Ile Pro Lys Gly Gly Phe Cys Leu Phe Asp Leu Arg Gly Cys Cys
1               5                   10                  15

Gly Met Cys Gly Cys Leu Ala Gly Val Cys Phe Asn Tyr Asp His Pro
            20                  25                  30

Cys Glu Glu
    35
```

<210> SEQ ID NO 42
<211> LENGTH: 33
<212> TYPE: PRT
<213> ORGANISM: Menyanthes trifoliata

<400> SEQUENCE: 42

Cys Leu Ser Ser Gly Gly Phe Cys Met Phe Arg Pro Asn Asp Cys Cys
1               5                   10                  15

Gly Asn Cys Gly Cys Leu Tyr Pro Val Gly Ile Cys Tyr Gly Thr Gly
            20                  25                  30

Cys

<210> SEQ ID NO 43
<211> LENGTH: 35
<212> TYPE: PRT
<213> ORGANISM: Oryza sativa

<400> SEQUENCE: 43

Cys Leu Pro Ala Gly Gly Phe Cys Met Phe Arg Pro Met Asp Cys Cys
1               5                   10                  15

Gly Asn Cys Gly Cys Leu Tyr Pro Val Gly Val Cys Tyr Gly Ser Arg
            20                  25                  30

Cys Glu Glu
        35

<210> SEQ ID NO 44
<211> LENGTH: 35
<212> TYPE: PRT
<213> ORGANISM: Pholisma arenarium

<400> SEQUENCE: 44

Cys Leu Pro Ala Gly Gly Phe Cys Met Phe Arg Pro Met Asp Cys Cys
1               5                   10                  15

Gly Asn Cys Gly Cys Leu Tyr Pro Val Gly Val Cys Tyr Gly Ser Arg
            20                  25                  30

Cys Glu Glu
        35

<210> SEQ ID NO 45
<211> LENGTH: 33
<212> TYPE: PRT
<213> ORGANISM: Pholisma arenarium

<400> SEQUENCE: 45

Cys Ile Ser Ala Gly Gly Phe Cys Phe Phe Asp Pro Met Asn Cys Cys
1               5                   10                  15

Gly Asn Cys Gly Cys Leu Tyr Pro Val Gly Ile Cys Val Gly Thr Asn
            20                  25                  30

Cys

<210> SEQ ID NO 46
<211> LENGTH: 31
<212> TYPE: PRT
<213> ORGANISM: Polyscias fruticosa

<400> SEQUENCE: 46

Cys Ser Pro Leu Gly Gly Lys Cys Gly Asp Leu Val Glu Cys Cys Ser
1               5                   10                  15

Gly Cys Val Cys Ile Trp Pro Thr Tyr Thr Cys Val Gly His Cys
            20                  25                  30

```
<210> SEQ ID NO 47
<211> LENGTH: 35
<212> TYPE: PRT
<213> ORGANISM: Polyscias fruticosa

<400> SEQUENCE: 47

Cys Ile Pro Leu Gly Gly Asp Cys Thr Asp Leu Phe Asp Cys Cys Pro
1               5                   10                  15

Gly Cys Val Cys Ile Ile Thr Asp Leu Thr Cys Asp Gly Asn Cys Phe
            20                  25                  30

Arg Gly Ala
        35

<210> SEQ ID NO 48
<211> LENGTH: 36
<212> TYPE: PRT
<213> ORGANISM: Polyscias fruticosa

<400> SEQUENCE: 48

Cys Leu Thr Leu Gly Leu Tyr Cys Gly Gly Ser Gly Glu Cys Cys
1               5                   10                  15

Ser Gly Cys Leu Cys Val Tyr Pro Thr Leu Thr Cys Arg Gly Asn Cys
            20                  25                  30

Tyr Arg Gly Ala
        35

<210> SEQ ID NO 49
<211> LENGTH: 34
<212> TYPE: PRT
<213> ORGANISM: Phyllanthus sp.

<400> SEQUENCE: 49

Cys Ser Asp Pro Gly Gly Tyr Cys Val Pro Phe Phe Gln Gly Cys Cys
1               5                   10                  15

Asn Asp Cys Ser Cys Leu Asp Leu Gly Val Val Ala Gly Val Cys Val
            20                  25                  30

Cys Ile

<210> SEQ ID NO 50
<211> LENGTH: 33
<212> TYPE: PRT
<213> ORGANISM: Populus trichocarpa

<400> SEQUENCE: 50

Cys Ile Ser Ser Gly Gly Trp Cys Phe Thr Gln Pro Lys Asn Cys Cys
1               5                   10                  15

Gly Asn Cys Gly Cys Leu Tyr Pro Ile Gly Ile Cys Phe Gly Ser Asp
            20                  25                  30

Cys

<210> SEQ ID NO 51
<211> LENGTH: 33
<212> TYPE: PRT
<213> ORGANISM: Populus trichocarpa

<400> SEQUENCE: 51

Cys Ile Ser Ser Gly Gly Trp Cys Phe Pro Asn Pro Lys Asn Cys Cys
1               5                   10                  15

Gly Asn Cys Gly Cys Leu Tyr Pro Ile Gly Ile Cys Phe Gly Ser Asp
```

```
                20                  25                  30
Cys

<210> SEQ ID NO 52
<211> LENGTH: 33
<212> TYPE: PRT
<213> ORGANISM: Populus tremula

<400> SEQUENCE: 52

Cys Ile Ser Ser Gly Gly Phe Cys Phe Thr Gln Pro Met Asn Cys Cys
1               5                   10                  15

Gly Asn Cys Gly Cys Leu Tyr Pro Leu Gly Ile Cys Tyr Gly Ser Asp
            20                  25                  30

Cys

<210> SEQ ID NO 53
<211> LENGTH: 33
<212> TYPE: PRT
<213> ORGANISM: Salix dasyclados

<400> SEQUENCE: 53

Cys Leu Pro Ser Gly Gly Phe Cys Met Phe Gln Pro Met Asn Cys Cys
1               5                   10                  15

Gly Asn Cys Gly Cys Leu Tyr Pro Ile Gly Val Cys Tyr Gly Ser Asn
            20                  25                  30

Cys

<210> SEQ ID NO 54
<211> LENGTH: 33
<212> TYPE: PRT
<213> ORGANISM: Theobroma cacao

<400> SEQUENCE: 54

Cys Leu Ser Ala Gly Gly Phe Cys Met Phe Asn Pro Met Asp Cys Cys
1               5                   10                  15

Gly Asn Cys Gly Cys Leu Tyr Pro Met Gly Ile Cys Tyr Gly Ser Gly
            20                  25                  30

Cys

<210> SEQ ID NO 55
<211> LENGTH: 33
<212> TYPE: PRT
<213> ORGANISM: Theobroma cacao

<400> SEQUENCE: 55

Cys Leu Ser Ala Gly Gly Phe Cys Met Phe Asn Pro Met Asp Cys Cys
1               5                   10                  15

Gly Asn Cys Gly Cys Leu Phe Pro Met Gly Ile Cys Tyr Gly Ser Gly
            20                  25                  30

Cys

<210> SEQ ID NO 56
<211> LENGTH: 33
<212> TYPE: PRT
<213> ORGANISM: Theobroma cacao

<400> SEQUENCE: 56

Cys Leu Ser Ala Gly Gly Phe Cys Met Phe Asn Pro Met Asp Cys Cys
1               5                   10                  15
```

Gly Asn Cys Gly Cys Leu Tyr Pro Met Gly Phe Cys Tyr Gly Ser Gly
            20                  25                  30

Cys

<210> SEQ ID NO 57
<211> LENGTH: 33
<212> TYPE: PRT
<213> ORGANISM: Theobroma cacao

<400> SEQUENCE: 57

Cys Leu Ser Ala Gly Gly Phe Cys Met Phe Asn Pro Met Asp Cys Cys
1               5                   10                  15

Gly Asn Cys Gly Cys Leu Tyr Pro Leu Gly Phe Cys Tyr Gly Ser Gly
            20                  25                  30

Cys

<210> SEQ ID NO 58
<211> LENGTH: 33
<212> TYPE: PRT
<213> ORGANISM: Theobroma cacao

<400> SEQUENCE: 58

Cys Leu Ser Ala Gly Gly Phe Cys Met Phe Asp Pro Met Asp Cys Cys
1               5                   10                  15

Gly Asn Cys Gly Cys Leu Tyr Pro Met Gly Ile Cys Tyr Gly Ser Gly
            20                  25                  30

Cys

<210> SEQ ID NO 59
<211> LENGTH: 33
<212> TYPE: PRT
<213> ORGANISM: Theobroma cacao

<400> SEQUENCE: 59

Cys Leu Ser Ala Gly Gly Phe Cys Met Phe Ile Pro Met Asp Cys Cys
1               5                   10                  15

Gly Asn Cys Gly Cys Leu Phe Leu Met Gly Phe Cys Tyr Gly Ser Gly
            20                  25                  30

Cys

<210> SEQ ID NO 60
<211> LENGTH: 33
<212> TYPE: PRT
<213> ORGANISM: Theobroma cacao

<400> SEQUENCE: 60

Cys Leu Ser Ala Gly Gly Phe Cys Met Phe Ile Pro Met Asp Cys Cys
1               5                   10                  15

Gly Asn Cys Gly Cys Leu Phe Pro Met Gly Phe Cys Tyr Gly Ser Gly
            20                  25                  30

Cys

<210> SEQ ID NO 61
<211> LENGTH: 33
<212> TYPE: PRT
<213> ORGANISM: Theobroma cacao

<400> SEQUENCE: 61

Cys Leu Ser Ala Gly Gly Phe Cys Met Phe Asn Pro Met Asp Cys Cys
1               5                   10                  15

Gly Asn Cys Gly Cys Leu Tyr Pro Met Gly Ile Cys Tyr Gly Ser Gly
            20                  25                  30

Cys

<210> SEQ ID NO 62
<211> LENGTH: 33
<212> TYPE: PRT
<213> ORGANISM: Theobroma cacao

<400> SEQUENCE: 62

Cys Pro Ser Ala Gly Gly Phe Cys Met Phe Asn Pro Met Asp Cys Cys
1               5                   10                  15

Gly Asn Cys Gly Cys Leu Tyr Pro Met Gly Ile Cys Tyr Gly Ser Gly
            20                  25                  30

Cys

<210> SEQ ID NO 63
<211> LENGTH: 33
<212> TYPE: PRT
<213> ORGANISM: Theobroma cacao

<400> SEQUENCE: 63

Cys Leu Ser Ala Gly Gly Phe Cys Met Phe Asn Pro Met Asp Cys Cys
1               5                   10                  15

Gly Asn Cys Gly Cys Leu Tyr Pro Leu Gly Ile Cys Tyr Gly Ser Gly
            20                  25                  30

Cys

<210> SEQ ID NO 64
<211> LENGTH: 35
<212> TYPE: PRT
<213> ORGANISM: Triticum aestivum

<400> SEQUENCE: 64

Cys Leu Pro Ala Gly Gly Phe Cys Met Phe Arg Pro Met Asp Cys Cys
1               5                   10                  15

Gly Asn Cys Gly Cys Leu Tyr Pro Ala Gly Val Cys Tyr Gly Thr Arg
            20                  25                  30

Cys Glu Glu
        35

<210> SEQ ID NO 65
<211> LENGTH: 408
<212> TYPE: PRT
<213> ORGANISM: artificial sequence
<220> FEATURE:
<223> OTHER INFORMATION: Maltose-binding protein

<400> SEQUENCE: 65

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

```
Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly
                405

<210> SEQ ID NO 66
<211> LENGTH: 5
<212> TYPE: PRT
<213> ORGANISM: artificial sequence
<220> FEATURE:
<223> OTHER INFORMATION: enterokinase cleavage sequence

<400> SEQUENCE: 66

Asp Asp Asp Asp Lys
1               5

<210> SEQ ID NO 67
```

<211> LENGTH: 444
<212> TYPE: PRT
<213> ORGANISM: artificial sequence
<220> FEATURE:
<223> OTHER INFORMATION: fusion protein

<400> SEQUENCE: 67

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

```
Glu Ala Leu Lys Asp Ala Gln Thr Asn Ser Ser Asn Asn Asn Asn
385                 390                 395                 400

Asn Asn Asn Asn Asn Asn Leu Gly Asp Asp Asp Lys Cys Lys Ser
                405                 410                 415

Gly Gly Ala Trp Cys Gly Phe Asp Pro His Gly Cys Cys Gly Asn Cys
        420                 425                 430

Gly Cys Leu Val Gly Phe Cys Tyr Gly Thr Gly Cys
        435                 440
```

<210> SEQ ID NO 68
<211> LENGTH: 444
<212> TYPE: PRT
<213> ORGANISM: artificial sequence
<220> FEATURE:
<223> OTHER INFORMATION: fusion protein

<400> SEQUENCE: 68

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300
```

-continued

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Lys Ser
            405                 410                 415

Ser Gly Ala Trp Cys Gly Phe Asp Pro His Gly Cys Cys Gly Asn Cys
        420                 425                 430

Gly Cys Leu Val Gly Phe Cys Tyr Gly Thr Gly Cys
    435                 440

<210> SEQ ID NO 69
<211> LENGTH: 444
<212> TYPE: PRT
<213> ORGANISM: artificial sequence
<220> FEATURE:
<223> OTHER INFORMATION: fusion protein

<400> SEQUENCE: 69

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220
```

-continued

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
        260                 265                 270

Leu Pro Thr Phe Lys Gly Gln Pro Ser Lys Pro Phe Val Gly Val Leu
    275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Lys Ser
            405                 410                 415

Ala Gly Thr Trp Cys Gly Phe Asp Pro His Gly Cys Cys Gly Ser Cys
        420                 425                 430

Gly Cys Leu Val Gly Phe Cys Tyr Gly Val Ser Cys
        435                 440

<210> SEQ ID NO 70
<211> LENGTH: 446
<212> TYPE: PRT
<213> ORGANISM: artificial sequence
<220> FEATURE:
<223> OTHER INFORMATION: fusion protein

<400> SEQUENCE: 70

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
            85                  90                  95

Ala Gln Ser Gly Leu Leu Ala Glu Ile Thr Pro Asp Lys Ala Phe Gln
        100                 105                 110

Asp Lys Leu Tyr Pro Phe Thr Trp Asp Ala Val Arg Tyr Asn Gly Lys
    115                 120                 125

Leu Ile Ala Tyr Pro Ile Ala Val Glu Ala Leu Ser Leu Ile Tyr Asn
130                 135                 140

```
Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Lys
                405                 410                 415

Asn Gly Glu Phe Cys Trp Gly Asp Pro Ser Gly Cys Cys Gly Asn Cys
            420                 425                 430

Gly Cys Leu Ile Ile Pro Gly Val Cys Tyr Gly Thr Gly Cys
            435                 440                 445

<210> SEQ ID NO 71
<211> LENGTH: 444
<212> TYPE: PRT
<213> ORGANISM: artificial sequence
<220> FEATURE:
<223> OTHER INFORMATION: fusion protein

<400> SEQUENCE: 71

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
50                  55                  60
```

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
             85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Lys Ser
                405                 410                 415

Ser Gly Ala Trp Cys Gly Phe Asp Pro His Gly Cys Cys Gly Asn Cys
            420                 425                 430

Gly Cys Leu Val Gly Phe Cys Tyr Gly Thr Asp Cys
        435                 440

<210> SEQ ID NO 72
<211> LENGTH: 444
<212> TYPE: PRT
<213> ORGANISM: artificial sequence
<220> FEATURE:

<223> OTHER INFORMATION: fusion protein

<400> SEQUENCE: 72

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ile Pro
            405                 410                 415

Gly Gly Gly Phe Cys Met Phe Glu Pro Leu Ser Cys Val Asn Cys
            420                 425                 430

Gly Cys Ile Leu Val Pro Gly Val Cys Tyr Cys Gly
            435                 440

<210> SEQ ID NO 73
<211> LENGTH: 444
<212> TYPE: PRT
<213> ORGANISM: artificial sequence
<220> FEATURE:
<223> OTHER INFORMATION: fusion protein

<400> SEQUENCE: 73

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

-continued

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Lys Ser
            405                 410                 415

Gly Gly Thr Trp Cys Gly Phe Asp Pro His Gly Cys Cys Gly Asn Cys
            420                 425                 430

Gly Cys Leu Val Gly Phe Cys Tyr Gly Thr Gly Cys
            435                 440

<210> SEQ ID NO 74
<211> LENGTH: 444
<212> TYPE: PRT
<213> ORGANISM: artificial sequence
<220> FEATURE:
<223> OTHER INFORMATION: fusion protein

<400> SEQUENCE: 74

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

```
Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ile Ser
            405                 410                 415

Ser Gly Gly Trp Cys Gly Phe Asp Leu His Gly Cys Cys Gly Asn Cys
            420                 425                 430

Gly Cys Leu Val Gly Phe Cys Tyr Gly Thr Gly Cys
            435                 440

<210> SEQ ID NO 75
<211> LENGTH: 444
<212> TYPE: PRT
<213> ORGANISM: artificial sequence
<220> FEATURE:
<223> OTHER INFORMATION: fusion protein

<400> SEQUENCE: 75

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65              70                  75                  80

Asp Gly Pro Asp Ile Ile Phe Trp Ala His Asp Arg Phe Gly Gly Tyr
            85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145             150                 155                 160
```

```
Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Lys Ser
                405                 410                 415

Gly Gly Ser Trp Cys Gly Phe Asp Pro His Gly Cys Cys Gly Asn Cys
            420                 425                 430

Gly Cys Leu Val Gly Phe Cys Tyr Gly Thr Gly Cys
        435                 440

<210> SEQ ID NO 76
<211> LENGTH: 444
<212> TYPE: PRT
<213> ORGANISM: artificial sequence
<220> FEATURE:
<223> OTHER INFORMATION: fusion protein

<400> SEQUENCE: 76

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80
```

```
Asp Gly Pro Asp Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
130             135                 140

Lys Asp Leu Leu Pro Asn Pro Pro Lys Thr Trp Glu Glu Ile Pro Ala
145             150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210             215                 220

Ile Lys Asn Lys His Met Asn Ala Asp Thr Asp Tyr Ser Ile Ala Glu
225             230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305             310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385             390                 395                 400

Asn Asn Asn Asn Asn Leu Gly Asp Asp Asp Lys Cys Ile Phe
            405                 410                 415

Ser Gly Gly Trp Cys Gly Phe Asp Leu His Gly Cys Cys Gly Asn Cys
            420                 425                 430

Gly Cys Leu Val Gly Phe Cys Tyr Gly Thr Gly Cys
            435                 440

<210> SEQ ID NO 77
<211> LENGTH: 446
<212> TYPE: PRT
<213> ORGANISM: artificial sequence
<220> FEATURE:
<223> OTHER INFORMATION: fusion protein

<400> SEQUENCE: 77
```

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Leu Lys
                405                 410                 415

Asn Gly Gln Phe Cys Trp Gly Asn Pro Ser Gly Cys Cys Gly Asn Cys
```

```
                420            425            430
Gly Cys Leu Ile Ile Pro Gly Val Cys Tyr Gly Thr Gly Cys
        435            440            445

<210> SEQ ID NO 78
<211> LENGTH: 444
<212> TYPE: PRT
<213> ORGANISM: artificial sequence
<220> FEATURE:
<223> OTHER INFORMATION: fusion protein

<400> SEQUENCE: 78

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
```

-continued

```
                    340                 345                 350
Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Pro
            405                 410                 415

Gly Gly Gly Phe Cys Met Phe Glu Pro Leu Ser Cys Cys His Asn Cys
            420                 425                 430

Gly Cys Leu Leu Val Pro Gly Val Cys Tyr Cys Gly
            435                 440

<210> SEQ ID NO 79
<211> LENGTH: 444
<212> TYPE: PRT
<213> ORGANISM: artificial sequence
<220> FEATURE:
<223> OTHER INFORMATION: fusion protein

<400> SEQUENCE: 79

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
```

```
                    260                 265                 270
Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ile Pro
                405                 410                 415

Asn Gly Gly Phe Cys Met Phe Glu Pro Leu Ser Cys Cys Val Asn Cys
            420                 425                 430

Gly Cys Ile Leu Val Pro Gly Val Cys Tyr Cys Gly
            435                 440

<210> SEQ ID NO 80
<211> LENGTH: 445
<212> TYPE: PRT
<213> ORGANISM: artificial sequence
<220> FEATURE:
<223> OTHER INFORMATION: fusion protein

<400> SEQUENCE: 80

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
```

180                 185                 190
Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Lys
                405                 410                 415

Val Gly Lys Ile Cys Leu Gly Arg Gly Leu Lys Glu Cys Cys Pro Ser
            420                 425                 430

Ala Thr Cys Gly Cys Leu Leu Gly Phe Cys Ile Lys Cys
        435                 440                 445

<210> SEQ ID NO 81
<211> LENGTH: 447
<212> TYPE: PRT
<213> ORGANISM: artificial sequence
<220> FEATURE:
<223> OTHER INFORMATION: fusion protein

<400> SEQUENCE: 81

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln 100                 105                 110
Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ile Pro
            405                 410                 415

Lys Gly Gly Trp Cys Leu Phe Asp Ile Met Gly Cys Cys Lys Pro Cys
            420                 425                 430

Gly Cys Leu Ala Gly Phe Cys Trp Val Val Gly Asp Asp Cys Asn
            435                 440                 445

<210> SEQ ID NO 82
<211> LENGTH: 449
<212> TYPE: PRT
<213> ORGANISM: artificial sequence
<220> FEATURE:
<223> OTHER INFORMATION: fusion protein

<400> SEQUENCE: 82

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys

```
                20              25              30
Leu Val Ile Trp Ile Asn Gly Asp Lys Gly Tyr Asn Gly Leu Ala Glu
            35              40              45
Val Gly Lys Lys Phe Glu Lys Asp Thr Gly Ile Lys Val Thr Val Glu
    50              55              60
His Pro Asp Lys Leu Glu Glu Lys Phe Pro Gln Val Ala Ala Thr Gly
65              70              75              80
Asp Gly Pro Asp Ile Ile Phe Trp Ala His Asp Arg Phe Gly Gly Tyr
                85              90              95
Ala Gln Ser Gly Leu Leu Ala Glu Ile Thr Pro Asp Lys Ala Phe Gln
            100             105             110
Asp Lys Leu Tyr Pro Phe Thr Trp Asp Ala Val Arg Tyr Asn Gly Lys
        115             120             125
Leu Ile Ala Tyr Pro Ile Ala Val Glu Ala Leu Ser Leu Ile Tyr Asn
        130             135             140
Lys Asp Leu Leu Pro Asn Pro Pro Lys Thr Trp Glu Glu Ile Pro Ala
145             150             155             160
Leu Asp Lys Glu Leu Lys Ala Lys Gly Lys Ser Ala Leu Met Phe Asn
            165             170             175
Leu Gln Glu Pro Tyr Phe Thr Trp Pro Leu Ile Ala Ala Asp Gly Gly
            180             185             190
Tyr Ala Phe Lys Tyr Glu Asn Gly Lys Tyr Asp Ile Lys Asp Val Gly
            195             200             205
Val Asp Asn Ala Gly Ala Lys Ala Gly Leu Thr Phe Leu Val Asp Leu
        210             215             220
Ile Lys Asn Lys His Met Asn Ala Asp Thr Asp Tyr Ser Ile Ala Glu
225             230             235             240
Ala Ala Phe Asn Lys Gly Glu Thr Ala Met Thr Ile Asn Gly Pro Trp
            245             250             255
Ala Trp Ser Asn Ile Asp Thr Ser Lys Val Asn Tyr Gly Val Thr Val
            260             265             270
Leu Pro Thr Phe Lys Gly Gln Pro Ser Lys Pro Phe Val Gly Val Leu
        275             280             285
Ser Ala Gly Ile Asn Ala Ala Ser Pro Asn Lys Glu Leu Ala Lys Glu
        290             295             300
Phe Leu Glu Asn Tyr Leu Leu Thr Asp Glu Gly Leu Glu Ala Val Asn
305             310             315             320
Lys Asp Lys Pro Leu Gly Ala Val Ala Leu Lys Ser Tyr Glu Glu Glu
            325             330             335
Leu Val Lys Asp Pro Arg Ile Ala Ala Thr Met Glu Asn Ala Gln Lys
            340             345             350
Gly Glu Ile Met Pro Asn Ile Pro Gln Met Ser Ala Phe Trp Tyr Ala
            355             360             365
Val Arg Thr Ala Val Ile Asn Ala Ala Ser Gly Arg Gln Thr Val Asp
        370             375             380
Glu Ala Leu Lys Asp Ala Gln Thr Asn Ser Ser Ser Asn Asn Asn Asn
385             390             395             400
Asn Asn Asn Asn Asn Leu Gly Asp Asp Asp Lys Cys Val Pro
            405             410             415
Lys Gly Thr Pro Cys Leu Tyr Lys Pro Glu Pro Cys Cys Gly Ala Asn
            420             425             430
Cys Phe Cys Asp Thr Ser Ala Tyr Thr Phe Gln Tyr Val Cys Lys Cys
            435             440             445
```

Tyr

<210> SEQ ID NO 83
<211> LENGTH: 448
<212> TYPE: PRT
<213> ORGANISM: artificial sequence
<220> FEATURE:
<223> OTHER INFORMATION: fusion protein

<400> SEQUENCE: 83

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

```
Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Pro
                405                 410                 415

Ser Gly Gly Phe Cys Met Phe Arg Pro Thr Asp Cys Cys Gly Asn Cys
            420                 425                 430

Gly Cys Leu Tyr Pro Val Gly Val Cys Tyr Gly Ser Arg Cys Glu Glu
            435                 440                 445
```

<210> SEQ ID NO 84
<211> LENGTH: 446
<212> TYPE: PRT
<213> ORGANISM: artificial sequence
<220> FEATURE:
<223> OTHER INFORMATION: fusion protein

<400> SEQUENCE: 84

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270
```

```
Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Lys
                405                 410                 415

Asn Gly Glu Phe Cys Trp Gly Asp Pro Ser Gly Cys Cys Gly Asn Cys
        420                 425                 430

Gly Cys Leu Ile Ile Pro Gly Val Cys Tyr Gly Thr Gly Cys
        435                 440                 445

<210> SEQ ID NO 85
<211> LENGTH: 443
<212> TYPE: PRT
<213> ORGANISM: artificial sequence
<220> FEATURE:
<223> OTHER INFORMATION: fusion protein

<400> SEQUENCE: 85

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190
```

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Asn
                405                 410                 415

Gly Gly Gly Tyr Cys Gly Ser Phe Thr Arg Glu Ala Cys Cys Tyr Asn
            420                 425                 430

Cys Val Cys Met Met Ala Phe Cys Val Cys Gly
            435                 440

<210> SEQ ID NO 86
<211> LENGTH: 448
<212> TYPE: PRT
<213> ORGANISM: artificial sequence
<220> FEATURE:
<223> OTHER INFORMATION: fusion protein

<400> SEQUENCE: 86

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

```
Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Lys Thr Trp Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ser Pro
                405                 410                 415

Phe Gly Lys Pro Cys Arg Tyr Asn Pro Trp Gly Cys Cys Asp Ser Cys
            420                 425                 430

Val Cys Val Ala Thr Pro Ala Asp Glu Gly Arg Cys Leu Gly Asn Cys
    435                 440                 445

<210> SEQ ID NO 87
<211> LENGTH: 446
<212> TYPE: PRT
<213> ORGANISM: artificial sequence
<220> FEATURE:
<223> OTHER INFORMATION: fusion protein

<400> SEQUENCE: 87

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30
```

-continued

```
Leu Val Ile Trp Ile Asn Gly Asp Lys Gly Tyr Asn Gly Leu Ala Glu
         35                  40                  45
Val Gly Lys Lys Phe Glu Lys Asp Thr Gly Ile Lys Val Thr Val Glu
 50                  55                  60
His Pro Asp Lys Leu Glu Glu Lys Phe Pro Gln Val Ala Ala Thr Gly
 65                  70                  75                  80
Asp Gly Pro Asp Ile Ile Phe Trp Ala His Asp Arg Phe Gly Gly Tyr
                 85                  90                  95
Ala Gln Ser Gly Leu Leu Ala Glu Ile Thr Pro Asp Lys Ala Phe Gln
            100                 105                 110
Asp Lys Leu Tyr Pro Phe Thr Trp Asp Ala Val Arg Tyr Asn Gly Lys
            115                 120                 125
Leu Ile Ala Tyr Pro Ile Ala Val Glu Ala Leu Ser Leu Ile Tyr Asn
            130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
            195                 200                 205
Val Asp Asn Ala Gly Ala Lys Ala Gly Leu Thr Phe Leu Val Asp Leu
            210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
                245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
            275                 280                 285
Ser Ala Gly Ile Asn Ala Ala Ser Pro Asn Lys Glu Leu Ala Lys Glu
            290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
                325                 330                 335
Leu Val Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
            355                 360                 365
Val Arg Thr Ala Val Ile Asn Ala Ala Ser Gly Arg Gln Thr Val Asp
            370                 375                 380
Glu Ala Leu Lys Asp Ala Gln Thr Asn Ser Ser Ser Asn Asn Asn Asn
385                 390                 395                 400
Asn Asn Asn Asn Asn Leu Gly Asp Asp Asp Lys Cys Leu Pro
                405                 410                 415
Asn Gly Gly Phe Cys Met Phe Arg Pro Met Asp Cys Cys Gly Ser Cys
            420                 425                 430
Gly Cys Leu Tyr Pro Val Gly Val Cys Phe Gly Thr Gly Cys
            435                 440                 445
```

<210> SEQ ID NO 88
<211> LENGTH: 446
<212> TYPE: PRT
<213> ORGANISM: artificial sequence
<220> FEATURE:
<223> OTHER INFORMATION: fusion protein

<400> SEQUENCE: 88

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
```

```
              370                 375                 380
Glu Ala Leu Lys Asp Ala Gln Thr Asn Ser Ser Asn Asn Asn
385                 390                 395                 400

Asn Asn Asn Asn Asn Leu Gly Asp Asp Asp Lys Cys Tyr Pro
                405                 410                 415

Lys Gly His Glu Cys Arg Thr Asp Pro Thr Leu Cys Cys His Asn Cys
            420                 425                 430

Gly Cys Ile Met Pro Val Gly Val Cys Phe Gly Ile Asn Cys
            435                 440                 445

<210> SEQ ID NO 89
<211> LENGTH: 446
<212> TYPE: PRT
<213> ORGANISM: artificial sequence
<220> FEATURE:
<223> OTHER INFORMATION: fusion protein

<400> SEQUENCE: 89

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
```

```
                290                 295                 300
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Pro
                405                 410                 415

Ser Gly Gly Phe Cys Met Phe Arg Pro Lys Asp Cys Cys Gly Ser Cys
                420                 425                 430

Gly Cys Leu Tyr Pro Ile Gly Val Cys Phe Gly Ser Ser Cys
                435                 440                 445

<210> SEQ ID NO 90
<211> LENGTH: 448
<212> TYPE: PRT
<213> ORGANISM: artificial sequence
<220> FEATURE:
<223> OTHER INFORMATION: fusion protein

<400> SEQUENCE: 90

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
                35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
                130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
```

```
                210                 215                 220
Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
                290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Pro
                405                 410                 415

Met Gly Gly Phe Cys Leu Phe Asn Leu Arg Gly Cys Cys Gly Ser Cys
                420                 425                 430

Gly Cys Leu Ala Gly Phe Cys Trp Arg Asp Ala Ser Ser Cys Asp Leu
                435                 440                 445
```

<210> SEQ ID NO 91
<211> LENGTH: 448
<212> TYPE: PRT
<213> ORGANISM: artificial sequence
<220> FEATURE:
<223> OTHER INFORMATION: fusion protein

<400> SEQUENCE: 91

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
                35                  40                  45

Val Gly Lys Lys Phe Glu Lys Asp Thr Gly Ile Lys Val Thr Val Glu
                50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
```

```
            130                 135                 140
Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ile Pro
                405                 410                 415

Met Gly Gly Phe Cys Leu Gly Asn Leu Arg Gly Cys Cys Gly Ser Cys
            420                 425                 430

Gly Cys Leu Ala Gly Phe Cys Trp Arg Pro Ala Ser Ser Cys Asp Ser
        435                 440                 445

<210> SEQ ID NO 92
<211> LENGTH: 448
<212> TYPE: PRT
<213> ORGANISM: artificial sequence
<220> FEATURE:
<223> OTHER INFORMATION: fusion protein

<400> SEQUENCE: 92

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
```

```
                50              55              60
His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Pro
                405                 410                 415

Ser Gly Gly Phe Cys Met Phe Arg Pro Lys Asp Cys Cys Gly Asn Cys
            420                 425                 430

Gly Cys Leu Tyr Pro Ile Gly Val Cys Tyr Gly Ser Arg Cys Glu Glu
            435                 440                 445

<210> SEQ ID NO 93
<211> LENGTH: 450
<212> TYPE: PRT
<213> ORGANISM: artificial sequence
```

<220> FEATURE:
<223> OTHER INFORMATION: fusion protein

<400> SEQUENCE: 93

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400
```

```
Asn Asn Asn Asn Asn Leu Gly Asp Asp Asp Lys Cys Lys Pro
            405                 410                 415

Lys Gly Ser Phe Cys Leu Phe Asp Leu Gln Ser Cys Cys Arg Pro Cys
            420                 425                 430

Gly Cys Leu Ala Gly Trp Cys Tyr Asn Ile Asp His Asp Cys Asn Glu
        435                 440                 445

Tyr Thr
    450

<210> SEQ ID NO 94
<211> LENGTH: 446
<212> TYPE: PRT
<213> ORGANISM: artificial sequence
<220> FEATURE:
<223> OTHER INFORMATION: fusion protein

<400> SEQUENCE: 94

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300
```

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Ser
            405                 410                 415

Ser Gly Gly Phe Cys Met Phe Asn Pro Arg Asp Cys Cys Gly Ser Cys
            420                 425                 430

Gly Cys Leu Tyr Pro Met Gly Ile Cys Tyr Gly Ser Ser Cys
            435                 440                 445

<210> SEQ ID NO 95
<211> LENGTH: 450
<212> TYPE: PRT
<213> ORGANISM: artificial sequence
<220> FEATURE:
<223> OTHER INFORMATION: fusion protein

<400> SEQUENCE: 95

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220
```

```
Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
        260                 265                 270

Leu Pro Thr Phe Lys Gly Gln Pro Ser Lys Pro Phe Val Gly Val Leu
    275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Lys Pro
                405                 410                 415

Ile Gly Ser Phe Cys Leu Phe Asp Leu Thr Ser Cys Cys Arg Pro Cys
            420                 425                 430

Gly Cys Leu Ala Gly Phe Cys Tyr Asn Leu Asp His Asn Cys Asn Glu
            435                 440                 445

Tyr Thr
    450

<210> SEQ ID NO 96
<211> LENGTH: 450
<212> TYPE: PRT
<213> ORGANISM: artificial sequence
<220> FEATURE:
<223> OTHER INFORMATION: fusion protein

<400> SEQUENCE: 96

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
            85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125
```

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Lys Pro
                405                 410                 415

Lys Gly Ser Phe Cys Leu Phe Asp Leu Thr Ser Cys Cys Arg Pro Cys
            420                 425                 430

Gly Cys Leu Ala Gly Trp Cys Tyr Asn Tyr Asp His Glu Cys Asn Glu
        435                 440                 445

Tyr Thr
    450

<210> SEQ ID NO 97
<211> LENGTH: 450
<212> TYPE: PRT
<213> ORGANISM: artificial sequence
<220> FEATURE:
<223> OTHER INFORMATION: fusion protein

<400> SEQUENCE: 97

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

```
Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                    85                  90                  95

Ala Gln Ser Gly Leu Leu Ala Glu Ile Thr Pro Asp Lys Ala Phe Gln
               100                 105                 110

Asp Lys Leu Tyr Pro Phe Thr Trp Asp Ala Val Arg Tyr Asn Gly Lys
           115                 120                 125

Leu Ile Ala Tyr Pro Ile Ala Val Glu Ala Leu Ser Leu Ile Tyr Asn
       130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ile Ala
                405                 410                 415

Lys Gly Gly Phe Cys Leu Phe Asp Leu Thr Ser Cys Cys Arg Pro Cys
            420                 425                 430

Gly Cys Leu Ala Gly Trp Cys Tyr Asn Ile Asp His Asp Cys Lys Glu
        435                 440                 445
```

Tyr Thr
    450

<210> SEQ ID NO 98
<211> LENGTH: 450
<212> TYPE: PRT
<213> ORGANISM: artificial sequence
<220> FEATURE:
<223> OTHER INFORMATION: fusion protein

<400> SEQUENCE: 98

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
          355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ile Ala
            405                 410                 415

Lys Gly Gly Phe Cys Leu Phe Asp Leu Thr Ser Cys Cys Arg Pro Cys
                420                 425                 430

Gly Cys Leu Ala Gly Trp Cys Tyr Asn Ile Asp His Asp Cys Asn Glu
        435                 440                 445

Tyr Ala
    450

<210> SEQ ID NO 99
<211> LENGTH: 450
<212> TYPE: PRT
<213> ORGANISM: artificial sequence
<220> FEATURE:
<223> OTHER INFORMATION: fusion protein

<400> SEQUENCE: 99

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

-continued

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Ala
                405                 410                 415

Lys Gly Gly Phe Cys Leu Phe Asp Leu Thr Ser Cys Cys Arg Pro Cys
            420                 425                 430

Gly Cys Leu Ala Gly Trp Cys Tyr Asn Ile Asp His Asp Cys Asn Glu
        435                 440                 445

Tyr Thr
    450

<210> SEQ ID NO 100
<211> LENGTH: 447
<212> TYPE: PRT
<213> ORGANISM: artificial sequence
<220> FEATURE:
<223> OTHER INFORMATION: fusion protein

<400> SEQUENCE: 100

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160
```

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ile Pro
                405                 410                 415

Lys Gly Gly Trp Cys Leu Phe Asp Ile Met Gly Cys Cys Lys Pro Cys
            420                 425                 430

Gly Cys Leu Ala Gly Phe Cys Trp Val Val Gly Asp Asp Cys Asn
        435                 440                 445

<210> SEQ ID NO 101
<211> LENGTH: 444
<212> TYPE: PRT
<213> ORGANISM: artificial sequence
<220> FEATURE:
<223> OTHER INFORMATION: fusion protein

<400> SEQUENCE: 101

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ser Pro
                405                 410                 415

Leu Gly Gly Lys Cys Gly Asp Leu Val Glu Cys Cys Ser Gly Cys Val
            420                 425                 430

Cys Ile Trp Pro Thr Tyr Thr Cys Val Gly His Cys
            435                 440

<210> SEQ ID NO 102
<211> LENGTH: 450
<212> TYPE: PRT
<213> ORGANISM: artificial sequence
<220> FEATURE:
<223> OTHER INFORMATION: fusion protein

<400> SEQUENCE: 102

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                      70                  75                  80

Asp Gly Pro Asp Ile Ile Phe Trp Ala His Asp Arg Phe Gly Gly Tyr
                    85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
        370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Gln Pro
                405                 410                 415

Phe Asp Ala Pro Cys Asp Thr Phe Tyr Gly Phe Tyr Cys Cys Gly Ser
```

```
                420             425             430
Cys Thr Cys Thr Tyr Val Asp Phe Trp His Thr Ser Arg Cys Thr Gly
        435                 440                 445

Ser Cys
    450

<210> SEQ ID NO 103
<211> LENGTH: 446
<212> TYPE: PRT
<213> ORGANISM: artificial sequence
<220> FEATURE:
<223> OTHER INFORMATION: fusion protein

<400> SEQUENCE: 103

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
```

```
                    325                 330                 335
Leu Val Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
            355                 360                 365
Val Arg Thr Ala Val Ile Asn Ala Ala Ser Gly Arg Gln Thr Val Asp
            370                 375                 380
Glu Ala Leu Lys Asp Ala Gln Thr Asn Ser Ser Ser Asn Asn Asn Asn
385                 390                 395                 400
Asn Asn Asn Asn Asn Leu Gly Asp Asp Asp Lys Cys Leu Pro
            405                 410                 415
Ala Gly Gly Phe Cys Met Phe Arg Pro Met Asp Cys Cys Gly Thr Cys
            420                 425                 430
Gly Cys Leu Tyr Pro Val Gly Val Cys Phe Gly Asn Asp Cys
            435                 440                 445

<210> SEQ ID NO 104
<211> LENGTH: 446
<212> TYPE: PRT
<213> ORGANISM: artificial sequence
<220> FEATURE:
<223> OTHER INFORMATION: fusion protein

<400> SEQUENCE: 104

Met Lys Ile Lys Thr Gly Ala Arg Ile Leu Ala Leu Ser Ala Leu Thr
1               5                   10                  15
Thr Met Met Phe Ser Ala Ser Ala Leu Ala Lys Ile Glu Glu Gly Lys
            20                  25                  30
Leu Val Ile Trp Ile Asn Gly Asp Lys Gly Tyr Asn Gly Leu Ala Glu
        35                  40                  45
Val Gly Lys Lys Phe Glu Lys Asp Thr Gly Ile Lys Val Thr Val Glu
    50                  55                  60
His Pro Asp Lys Leu Glu Glu Lys Phe Pro Gln Val Ala Ala Thr Gly
65                  70                  75                  80
Asp Gly Pro Asp Ile Ile Phe Trp Ala His Asp Arg Phe Gly Gly Tyr
                85                  90                  95
Ala Gln Ser Gly Leu Leu Ala Glu Ile Thr Pro Asp Lys Ala Phe Gln
            100                 105                 110
Asp Lys Leu Tyr Pro Phe Thr Trp Asp Ala Val Arg Tyr Asn Gly Lys
        115                 120                 125
Leu Ile Ala Tyr Pro Ile Ala Val Glu Ala Leu Ser Leu Ile Tyr Asn
    130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
        195                 200                 205
Val Asp Asn Ala Gly Ala Lys Ala Gly Leu Thr Phe Leu Val Asp Leu
    210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
```

```
                        245                 250                 255
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Gly
                405                 410                 415

Ala Gly Gly Phe Cys Met Phe Asn Pro Met Asp Cys Cys Gly Asn Cys
            420                 425                 430

Gly Cys Leu Tyr Pro Val Gly Ile Cys Phe Gly Thr Gly Cys
            435                 440                 445

<210> SEQ ID NO 105
<211> LENGTH: 443
<212> TYPE: PRT
<213> ORGANISM: artificial sequence
<220> FEATURE:
<223> OTHER INFORMATION: fusion protein

<400> SEQUENCE: 105

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
```

```
            165                 170                 175
Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Leu Asn
            405                 410                 415

Gly Gly Gly Tyr Cys Gly Ser Phe Thr Arg Glu Ala Cys Cys Tyr Asn
            420                 425                 430

Cys Val Cys Met Met Ala Phe Cys Val Cys Gly
            435                 440

<210> SEQ ID NO 106
<211> LENGTH: 444
<212> TYPE: PRT
<213> ORGANISM: artificial sequence
<220> FEATURE:
<223> OTHER INFORMATION: fusion protein

<400> SEQUENCE: 106

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
            50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
```

```
                85                  90                  95
Ala Gln Ser Gly Leu Leu Ala Glu Ile Thr Pro Asp Lys Ala Phe Gln
            100                 105                 110
Asp Lys Leu Tyr Pro Phe Thr Trp Asp Ala Val Arg Tyr Asn Gly Lys
            115                 120                 125
Leu Ile Ala Tyr Pro Ile Ala Val Glu Ala Leu Ser Leu Ile Tyr Asn
            130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
            165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
            195                 200                 205
Val Asp Asn Ala Gly Ala Lys Ala Gly Leu Thr Phe Leu Val Asp Leu
            210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
            245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
            275                 280                 285
Ser Ala Gly Ile Asn Ala Ala Ser Pro Asn Lys Glu Leu Ala Lys Glu
            290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
            325                 330                 335
Leu Val Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
            355                 360                 365
Val Arg Thr Ala Val Ile Asn Ala Ala Ser Gly Arg Gln Thr Val Asp
            370                 375                 380
Glu Ala Leu Lys Asp Ala Gln Thr Asn Ser Ser Ser Asn Asn Asn Asn
385                 390                 395                 400
Asn Asn Asn Asn Asn Leu Gly Asp Asp Asp Lys Cys Lys Ser
            405                 410                 415
Ala Gly Glu Trp Cys Gly Phe Ser Trp Thr Asp Cys Cys Asn Ser Cys
            420                 425                 430
Gly Cys Leu Ala Gly Phe Cys Tyr Gly Thr Ser Cys
            435                 440

<210> SEQ ID NO 107
<211> LENGTH: 448
<212> TYPE: PRT
<213> ORGANISM: artificial sequence
<220> FEATURE:
<223> OTHER INFORMATION: fusion protein

<400> SEQUENCE: 107

Met Lys Ile Lys Thr Gly Ala Arg Ile Leu Ala Leu Ser Ala Leu Thr
```

-continued

```
1               5                    10                   15
Thr Met Met Phe Ser Ala Ser Ala Leu Ala Lys Ile Glu Glu Gly Lys
                20                  25                  30
Leu Val Ile Trp Ile Asn Gly Asp Lys Gly Tyr Asn Gly Leu Ala Glu
                35                  40                  45
Val Gly Lys Lys Phe Glu Lys Asp Thr Gly Ile Lys Val Thr Val Glu
                50                  55                  60
His Pro Asp Lys Leu Glu Glu Lys Phe Pro Gln Val Ala Ala Thr Gly
65                  70                  75                  80
Asp Gly Pro Asp Ile Ile Phe Trp Ala His Asp Arg Phe Gly Gly Tyr
                    85                  90                  95
Ala Gln Ser Gly Leu Leu Ala Glu Ile Thr Pro Asp Lys Ala Phe Gln
                100                 105                 110
Asp Lys Leu Tyr Pro Phe Thr Trp Asp Ala Val Arg Tyr Asn Gly Lys
                115                 120                 125
Leu Ile Ala Tyr Pro Ile Ala Val Glu Ala Leu Ser Leu Ile Tyr Asn
                130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
                180                 185                 190
Tyr Ala Phe Lys Tyr Glu Asn Gly Lys Tyr Asp Ile Lys Asp Val Gly
                195                 200                 205
Val Asp Asn Ala Gly Ala Lys Ala Gly Leu Thr Phe Leu Val Asp Leu
                210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
                245                 250                 255
Ala Trp Ser Asn Ile Asp Thr Ser Lys Val Asn Tyr Gly Val Thr Val
                260                 265                 270
Leu Pro Thr Phe Lys Gly Gln Pro Ser Lys Pro Phe Val Gly Val Leu
                275                 280                 285
Ser Ala Gly Ile Asn Ala Ala Ser Pro Asn Lys Glu Leu Ala Lys Glu
                290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
                325                 330                 335
Leu Val Lys Asp Pro Arg Ile Ala Ala Thr Met Glu Asn Ala Gln Lys
                340                 345                 350
Gly Glu Ile Met Pro Asn Ile Pro Gln Met Ser Ala Phe Trp Tyr Ala
                355                 360                 365
Val Arg Thr Ala Val Ile Asn Ala Ala Ser Gly Arg Gln Thr Val Asp
                370                 375                 380
Glu Ala Leu Lys Asp Ala Gln Thr Asn Ser Ser Ser Asn Asn Asn Asn
385                 390                 395                 400
Asn Asn Asn Asn Asn Leu Gly Asp Asp Asp Lys Cys Ile Pro
                    405                 410                 415
Lys Gly Gly Phe Cys Leu Phe Asp Leu Arg Gly Cys Cys Gly Met Cys
                420                 425                 430
```

```
Gly Cys Leu Ala Gly Val Cys Phe Asn Tyr Asp His Pro Cys Glu Glu
            435                 440                 445
```

<210> SEQ ID NO 108
<211> LENGTH: 446
<212> TYPE: PRT
<213> ORGANISM: artificial sequence
<220> FEATURE:
<223> OTHER INFORMATION: fusion protein

<400> SEQUENCE: 108

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350
```

```
Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Ser
                405                 410                 415

Ser Gly Gly Phe Cys Met Phe Arg Pro Asn Asp Cys Cys Gly Asn Cys
            420                 425                 430

Gly Cys Leu Tyr Pro Val Gly Ile Cys Tyr Gly Thr Gly Cys
            435                 440                 445

<210> SEQ ID NO 109
<211> LENGTH: 448
<212> TYPE: PRT
<213> ORGANISM: artificial sequence
<220> FEATURE:
<223> OTHER INFORMATION: fusion protein

<400> SEQUENCE: 109

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270
```

```
Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Pro
            405                 410                 415

Ala Gly Gly Phe Cys Met Phe Arg Pro Met Asp Cys Cys Gly Asn Cys
            420                 425                 430

Gly Cys Leu Tyr Pro Val Gly Val Cys Tyr Gly Ser Arg Cys Glu Glu
            435                 440                 445
```

<210> SEQ ID NO 110
<211> LENGTH: 448
<212> TYPE: PRT
<213> ORGANISM: artificial sequence
<220> FEATURE:
<223> OTHER INFORMATION: fusion protein

<400> SEQUENCE: 110

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190
```

```
Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Leu Pro
                405                 410                 415

Ala Gly Gly Phe Cys Met Phe Arg Pro Met Asp Cys Cys Gly Asn Cys
                420                 425                 430

Gly Cys Leu Tyr Pro Val Gly Val Cys Tyr Gly Ser Arg Cys Glu Glu
            435                 440                 445
```

<210> SEQ ID NO 111
<211> LENGTH: 446
<212> TYPE: PRT
<213> ORGANISM: artificial sequence
<220> FEATURE:
<223> OTHER INFORMATION: fusion protein

<400> SEQUENCE: 111

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110
```

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Ser
                405                 410                 415

Ala Gly Gly Phe Cys Phe Phe Asp Pro Met Asn Cys Cys Gly Asn Cys
            420                 425                 430

Gly Cys Leu Tyr Pro Val Gly Ile Cys Val Gly Thr Asn Cys
        435                 440                 445

<210> SEQ ID NO 112
<211> LENGTH: 444
<212> TYPE: PRT
<213> ORGANISM: artificial sequence
<220> FEATURE:
<223> OTHER INFORMATION: fusion protein

<400> SEQUENCE: 112

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

```
Leu Val Ile Trp Ile Asn Gly Asp Lys Gly Tyr Asn Gly Leu Ala Glu
             35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Ser Pro
                405                 410                 415

Leu Gly Gly Lys Cys Gly Asp Leu Val Glu Cys Cys Ser Gly Cys Val
            420                 425                 430

Cys Ile Trp Pro Thr Tyr Thr Cys Val Gly His Cys
        435                 440
```

<210> SEQ ID NO 113
<211> LENGTH: 448
<212> TYPE: PRT
<213> ORGANISM: artificial sequence
<220> FEATURE:
<223> OTHER INFORMATION: fusion protein

<400> SEQUENCE: 113

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Pro
                405                 410                 415

Leu Gly Gly Asp Cys Thr Asp Leu Phe Asp Cys Cys Pro Gly Cys Val
                420                 425                 430

Cys Ile Ile Thr Asp Leu Thr Cys Asp Gly Asn Cys Phe Arg Gly Ala
                435                 440                 445

<210> SEQ ID NO 114
<211> LENGTH: 449
<212> TYPE: PRT
<213> ORGANISM: artificial sequence
<220> FEATURE:
<223> OTHER INFORMATION: fusion protein

<400> SEQUENCE: 114

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285
```

```
Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Thr
                405                 410                 415

Leu Gly Leu Tyr Cys Gly Gly Ser Gly Glu Cys Cys Ser Gly Cys
            420                 425                 430

Leu Cys Val Tyr Pro Thr Leu Thr Cys Arg Gly Asn Cys Tyr Arg Gly
            435                 440                 445

Ala

<210> SEQ ID NO 115
<211> LENGTH: 447
<212> TYPE: PRT
<213> ORGANISM: artificial sequence
<220> FEATURE:
<223> OTHER INFORMATION: fusion protein

<400> SEQUENCE: 115

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
```

```
              195                 200                 205
Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ser Asp
                405                 410                 415

Pro Gly Gly Tyr Cys Val Pro Phe Phe Gln Gly Cys Cys Asn Asp Cys
                420                 425                 430

Ser Cys Leu Asp Leu Gly Val Val Ala Gly Val Cys Val Cys Ile
                435                 440                 445

<210> SEQ ID NO 116
<211> LENGTH: 446
<212> TYPE: PRT
<213> ORGANISM: artificial sequence
<220> FEATURE:
<223> OTHER INFORMATION: fusion protein

<400> SEQUENCE: 116

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
```

```
            115                 120                 125
Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Ile Ser
                405                 410                 415

Ser Gly Gly Trp Cys Phe Thr Gln Pro Lys Asn Cys Cys Gly Asn Cys
            420                 425                 430

Gly Cys Leu Tyr Pro Ile Gly Ile Cys Phe Gly Ser Asp Cys
        435                 440                 445

<210> SEQ ID NO 117
<211> LENGTH: 446
<212> TYPE: PRT
<213> ORGANISM: artificial sequence
<220> FEATURE:
<223> OTHER INFORMATION: fusion protein

<400> SEQUENCE: 117

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
```

35                  40                  45
Val Gly Lys Lys Phe Glu Lys Asp Thr Gly Ile Lys Val Thr Val Glu
                50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                    85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
                130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
                290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Ile Ser
                405                 410                 415

Ser Gly Gly Trp Cys Phe Pro Asn Pro Lys Asn Cys Cys Gly Asn Cys
                420                 425                 430

Gly Cys Leu Tyr Pro Ile Gly Ile Cys Phe Gly Ser Asp Cys
                435                 440                 445

<210> SEQ ID NO 118

<211> LENGTH: 446
<212> TYPE: PRT
<213> ORGANISM: artificial sequence
<220> FEATURE:
<223> OTHER INFORMATION: fusion protein

<400> SEQUENCE: 118

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380
```

```
Glu Ala Leu Lys Asp Ala Gln Thr Asn Ser Ser Asn Asn Asn Asn
385                 390                 395                 400

Asn Asn Asn Asn Asn Leu Gly Asp Asp Asp Lys Cys Ile Ser
            405                 410                 415

Ser Gly Gly Phe Cys Phe Thr Gln Pro Met Asn Cys Cys Gly Asn Cys
        420                 425                 430

Gly Cys Leu Tyr Pro Leu Gly Ile Cys Tyr Gly Ser Asp Cys
        435                 440                 445

<210> SEQ ID NO 119
<211> LENGTH: 446
<212> TYPE: PRT
<213> ORGANISM: artificial sequence
<220> FEATURE:
<223> OTHER INFORMATION: fusion protein

<400> SEQUENCE: 119

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300
```

-continued

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Pro
                405                 410                 415

Ser Gly Gly Phe Cys Met Phe Gln Pro Met Asn Cys Cys Gly Asn Cys
            420                 425                 430

Gly Cys Leu Tyr Pro Ile Gly Val Cys Tyr Gly Ser Asn Cys
        435                 440                 445

<210> SEQ ID NO 120
<211> LENGTH: 446
<212> TYPE: PRT
<213> ORGANISM: artificial sequence
<220> FEATURE:
<223> OTHER INFORMATION: fusion protein

<400> SEQUENCE: 120

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220
```

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Ser
            405                 410                 415

Ala Gly Gly Phe Cys Met Phe Asn Pro Met Asp Cys Cys Gly Asn Cys
            420                 425                 430

Gly Cys Leu Tyr Pro Met Gly Ile Cys Tyr Gly Ser Gly Cys
            435                 440                 445

<210> SEQ ID NO 121
<211> LENGTH: 446
<212> TYPE: PRT
<213> ORGANISM: artificial sequence
<220> FEATURE:
<223> OTHER INFORMATION: fusion protein

<400> SEQUENCE: 121

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
            85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

-continued

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
        180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Ser
                405                 410                 415

Ala Gly Gly Phe Cys Met Phe Asn Pro Met Asp Cys Cys Gly Asn Cys
        420                 425                 430

Gly Cys Leu Phe Pro Met Gly Ile Cys Tyr Gly Ser Gly Cys
            435                 440                 445

<210> SEQ ID NO 122
<211> LENGTH: 446
<212> TYPE: PRT
<213> ORGANISM: artificial sequence
<220> FEATURE:
<223> OTHER INFORMATION: fusion protein

<400> SEQUENCE: 122

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
             85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Ser
                405                 410                 415

Ala Gly Gly Phe Cys Met Phe Asn Pro Met Asp Cys Cys Gly Asn Cys
            420                 425                 430

Gly Cys Leu Tyr Pro Met Gly Phe Cys Tyr Gly Ser Gly Cys
        435                 440                 445

<210> SEQ ID NO 123
<211> LENGTH: 446
<212> TYPE: PRT
<213> ORGANISM: artificial sequence
<220> FEATURE:

<223> OTHER INFORMATION: fusion protein

<400> SEQUENCE: 123

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400
```

```
Asn Asn Asn Asn Asn Asn Leu Gly Asp Asp Asp Asp Lys Cys Leu Ser
                405                 410                 415

Ala Gly Gly Phe Cys Met Phe Asn Pro Met Asp Cys Cys Gly Asn Cys
            420                 425                 430

Gly Cys Leu Tyr Pro Leu Gly Phe Cys Tyr Gly Ser Gly Cys
        435                 440                 445

<210> SEQ ID NO 124
<211> LENGTH: 446
<212> TYPE: PRT
<213> ORGANISM: artificial sequence
<220> FEATURE:
<223> OTHER INFORMATION: fusion protein

<400> SEQUENCE: 124

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320
```

```
Lys Asp Lys Pro Leu Gly Ala Val Ala Leu Lys Ser Tyr Glu Glu Glu
            325                 330                 335

Leu Val Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Asn Asn Asn Asn Asn
385                 390                 395                 400

Asn Asn Asn Asn Asn Leu Gly Asp Asp Asp Lys Cys Leu Ser
            405                 410                 415

Ala Gly Gly Phe Cys Met Phe Asp Pro Met Asp Cys Cys Gly Asn Cys
        420                 425                 430

Gly Cys Leu Tyr Pro Met Gly Ile Cys Tyr Gly Ser Gly Cys
            435                 440                 445

<210> SEQ ID NO 125
<211> LENGTH: 446
<212> TYPE: PRT
<213> ORGANISM: artificial sequence
<220> FEATURE:
<223> OTHER INFORMATION: fusion protein

<400> SEQUENCE: 125

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240
```

```
Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
                370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Asp Lys Cys Leu Ser
                405                 410                 415

Ala Gly Gly Phe Cys Met Phe Asn Pro Met Asp Cys Cys Gly Asn Cys
                420                 425                 430

Gly Cys Leu Tyr Pro Leu Gly Ile Cys Tyr Gly Ser Gly Cys
            435                 440                 445

<210> SEQ ID NO 126
<211> LENGTH: 446
<212> TYPE: PRT
<213> ORGANISM: artificial sequence
<220> FEATURE:
<223> OTHER INFORMATION: fusion protein

<400> SEQUENCE: 126

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160
```

```
Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
        180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Ser
                405                 410                 415

Ala Gly Gly Phe Cys Met Phe Ile Pro Met Asp Cys Cys Gly Asn Cys
            420                 425                 430

Gly Cys Leu Phe Pro Met Gly Phe Cys Tyr Gly Ser Gly Cys
        435                 440                 445

<210> SEQ ID NO 127
<211> LENGTH: 446
<212> TYPE: PRT
<213> ORGANISM: artificial sequence
<220> FEATURE:
<223> OTHER INFORMATION: fusion protein

<400> SEQUENCE: 127

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80
```

```
Asp Gly Pro Asp Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Leu Ser
                405                 410                 415

Ala Gly Gly Phe Cys Met Phe Asn Pro Met Asp Cys Cys Gly Asn Cys
            420                 425                 430

Gly Cys Leu Tyr Pro Met Gly Ile Cys Tyr Gly Ser Gly Cys
        435                 440                 445

<210> SEQ ID NO 128
<211> LENGTH: 446
<212> TYPE: PRT
<213> ORGANISM: artificial sequence
<220> FEATURE:
<223> OTHER INFORMATION: fusioni protein

<400> SEQUENCE: 128
```

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Asp Lys Cys Pro Ser
                405                 410                 415

Ala Gly Gly Phe Cys Met Phe Asn Pro Met Asp Cys Cys Gly Asn Cys
```

420                 425                 430
Gly Cys Leu Tyr Pro Met Gly Ile Cys Tyr Gly Ser Gly Cys
            435                 440                 445

<210> SEQ ID NO 129
<211> LENGTH: 446
<212> TYPE: PRT
<213> ORGANISM: artificial sequence
<220> FEATURE:
<223> OTHER INFORMATION: fusion protein

<400> SEQUENCE: 129

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Val Lys Asp Pro Arg Ile Ala Ala Thr Met Glu Asn Ala Gln Lys

```
                    340                 345                 350
Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Asp Asp Asp Lys Cys Leu Ser
                405                 410                 415

Ala Gly Gly Phe Cys Met Phe Asn Pro Met Asp Cys Cys Gly Asn Cys
                420                 425                 430

Gly Cys Leu Tyr Pro Leu Gly Ile Cys Tyr Gly Ser Gly Cys
                435                 440                 445

<210> SEQ ID NO 130
<211> LENGTH: 448
<212> TYPE: PRT
<213> ORGANISM: artificial sequence
<220> FEATURE:
<223> OTHER INFORMATION: fusion protein

<400> SEQUENCE: 130

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
```

260                 265                 270
Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Val Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
            370                 375                 380

Glu Ala Leu Lys Asp Ala Gln Thr Asn Ser Ser Ser Asn Asn Asn Asn
385                 390                 395                 400

Asn Asn Asn Asn Asn Asn Leu Gly Asp Asp Asp Lys Cys Leu Pro
                405                 410                 415

Ala Gly Gly Phe Cys Met Phe Arg Pro Met Asp Cys Cys Gly Asn Cys
                420                 425                 430

Gly Cys Leu Tyr Pro Ala Gly Val Cys Tyr Gly Thr Arg Cys Glu Glu
                435                 440                 445

<210> SEQ ID NO 131
<211> LENGTH: 25
<212> TYPE: PRT
<213> ORGANISM: artificial sequence
<220> FEATURE:
<223> OTHER INFORMATION: artificial sequence

<400> SEQUENCE: 131

Cys Lys Ser Gly Gly Ala Trp Cys Gly Phe Asp Pro His Gly Cys Cys
1               5                   10                  15

Gly Asn Cys Gly Cys Leu Val Gly Phe
            20                  25

<210> SEQ ID NO 132
<211> LENGTH: 29
<212> TYPE: PRT
<213> ORGANISM: artificial sequence
<220> FEATURE:
<223> OTHER INFORMATION: artifical sequence

<400> SEQUENCE: 132

Ser Gly Gly Ala Trp Cys Gly Phe Asp Pro His Gly Cys Cys Gly Asn
1               5                   10                  15

Cys Gly Cys Leu Val Gly Phe Cys Tyr Gly Thr Gly Cys
            20                  25

<210> SEQ ID NO 133
<211> LENGTH: 121
<212> TYPE: PRT
<213> ORGANISM: Panax ginseng

<400> SEQUENCE: 133

Met Glu Asn Lys Lys Val Ala Leu Val Val Ala Met Val Val Val
1               5                   10                  15

Leu Ile Ser Thr Phe Ala Pro Leu Ala Leu Ala Ala Asp Glu Ala Gly

```
                20                  25                  30

Arg Ser Asp Gly Gly Asn Gly Asp Leu Ile Ala Val Glu Ser Val Ser
            35                  40                  45

Arg Ser Asn Gly Gly Asn Gly Asp Ser Val Thr Val Asp Thr Val Ser
        50                  55                  60

Trp Val Ser Ser Asn Arg Lys Thr Leu Arg Ser Ser Ile Phe Leu Pro
65                  70                  75                  80

Gln Gly Tyr Leu Pro Asp Gly Leu Gly Cys Lys Ser Gly Gly Ala
            85                  90                  95

Trp Cys Gly Phe Asp Pro His Gly Cys Cys Gly Asn Cys Gly Cys Leu
            100                 105                 110

Val Gly Phe Cys Tyr Gly Thr Gly Cys
            115                 120

<210> SEQ ID NO 134
<211> LENGTH: 121
<212> TYPE: PRT
<213> ORGANISM: Panax ginseng

<400> SEQUENCE: 134

Met Glu Asn Lys Lys Val Ala Leu Val Val Ala Met Val Val Val
1               5                   10                  15

Leu Ile Ser Thr Phe Ala Pro Leu Ala Leu Ala Ala Asp Glu Ala Gly
            20                  25                  30

Arg Ser Asp Gly Gly Asn Gly Asp Leu Ile Ala Val Glu Ser Val Ser
            35                  40                  45

Arg Ser Asn Gly Gly Asn Gly Asp Ser Val Thr Val Asp Thr Val Ser
        50                  55                  60

Trp Val Ser Ser Asn Arg Lys Thr Leu Arg Ser Ser Ile Phe Leu Pro
65                  70                  75                  80

Gln Gly Tyr Leu Pro Asp Gly Leu Gly Cys Lys Ser Ser Gly Ala
            85                  90                  95

Trp Cys Gly Phe Asp Pro His Gly Cys Cys Gly Asn Cys Gly Cys Leu
            100                 105                 110

Val Gly Phe Cys Tyr Gly Thr Gly Cys
            115                 120

<210> SEQ ID NO 135
<211> LENGTH: 115
<212> TYPE: PRT
<213> ORGANISM: Panax ginseng

<400> SEQUENCE: 135

Asn Lys Lys Val Ala Leu Val Val Val Ala Met Val Val Val Leu Ile
1               5                   10                  15

Ser Thr Val Ala Pro Leu Ala Met Ala Val Asp Asp Ala Gly Ser Ser
            20                  25                  30

Asp Gly Leu Ile Ala Val Glu Ser Val Ser Arg Ser Asn Gly Gly Asn
            35                  40                  45

Gly Asp Ser Val Ala Val Asp Thr Val Ser Trp Val Ser Ser Asn Arg
        50                  55                  60

Lys Thr Leu Arg Ser Lys Ile Phe Leu Pro Gln Gly Tyr Leu Pro Asp
65                  70                  75                  80

Gly Gly Leu Gly Cys Lys Ser Ala Gly Thr Trp Cys Gly Phe Asp Pro
            85                  90                  95

His Gly Cys Cys Gly Ser Cys Gly Cys Leu Val Gly Phe Cys Tyr Gly
```

```
                    100                 105                 110

Val Ser Cys
        115

<210> SEQ ID NO 136
<211> LENGTH: 42
<212> TYPE: PRT
<213> ORGANISM: Panax ginseng

<400> SEQUENCE: 136

Glu Ile Leu Pro Asp Gly Gly Leu Gly Cys Leu Lys Asn Gly Glu Phe
1               5                   10                  15

Cys Trp Gly Asp Pro Ser Gly Cys Cys Gly Asn Cys Gly Cys Leu Ile
            20                  25                  30

Ile Pro Gly Val Cys Tyr Gly Thr Gly Cys
        35                  40

<210> SEQ ID NO 137
<211> LENGTH: 121
<212> TYPE: PRT
<213> ORGANISM: Panax ginseng

<400> SEQUENCE: 137

Met Glu Asn Lys Lys Val Ala Leu Val Val Ala Met Val Val
1               5                   10                  15

Leu Ile Ser Thr Phe Ala Pro Leu Ala Leu Ala Ala Asp Glu Ala Gly
            20                  25                  30

Ser Ser Asp Gly Gly Asn Gly Asp Leu Ile Ala Val Glu Ser Val Ser
        35                  40                  45

Arg Ser Asn Gly Phe Asn Gly Asp Ser Val Ala Val Asp Thr Val Ser
    50                  55                  60

Arg Val Ser Ser Asn Arg Lys Thr Leu Arg Ser Asn Ile Phe Leu Pro
65                  70                  75                  80

Gln Gly Tyr Leu Pro Asp Gly Leu Gly Cys Lys Ser Ser Gly Ala
                85                  90                  95

Trp Cys Gly Phe Asp Pro His Gly Cys Cys Gly Asn Cys Gly Cys Leu
            100                 105                 110

Val Gly Phe Cys Tyr Gly Thr Asp Cys
        115                 120

<210> SEQ ID NO 138
<211> LENGTH: 108
<212> TYPE: PRT
<213> ORGANISM: Panax ginseng

<400> SEQUENCE: 138

Met Glu Asn Lys Lys Val Ala Leu Val Val Leu Leu Ala Ala Met Ala
1               5                   10                  15

Val Leu Thr Asp Leu Thr Leu Ala Thr Asp Asp Lys Ala Gly His Ser
            20                  25                  30

Asp Gly Gly Ala Asp Arg Ser Asn Gly Asn Glu Val Leu Ile Asp
        35                  40                  45

Ala Pro Gly Arg Ala Ser Val Tyr Lys Asn Leu Pro Leu Ser Arg Phe
    50                  55                  60

Phe Leu Arg Glu Lys Tyr Leu Pro Asp Gly Leu Gly Cys Ile Pro
65                  70                  75                  80

Gly Gly Gly Phe Cys Met Phe Glu Pro Leu Ser Cys Cys Val Asn Cys
                85                  90                  95
```

```
Gly Cys Ile Leu Val Pro Gly Val Cys Tyr Cys Gly
            100                 105
```

<210> SEQ ID NO 139
<211> LENGTH: 121
<212> TYPE: PRT
<213> ORGANISM: Panax ginseng

<400> SEQUENCE: 139

```
Met Glu Asn Lys Lys Val Ala Leu Val Val Ala Met Val Val Val
1               5                   10                  15

Leu Ile Ser Thr Phe Ala Pro Leu Ala Leu Ala Ala Asp Glu Ala Gly
            20                  25                  30

Arg Ser Asp Gly Gly Asn Gly Asp Leu Ile Ala Val Glu Ser Val Ser
        35                  40                  45

Arg Ser Asn Gly Gly Asn Gly Asp Ser Val Thr Val Asp Thr Val Ser
        50                  55                  60

Trp Val Ser Ser Asn Arg Lys Thr Leu Arg Ser Ser Ile Phe Leu Pro
65                  70                  75                  80

Gln Gly Tyr Leu Pro Asp Gly Gly Leu Gly Cys Lys Ser Gly Gly Thr
                85                  90                  95

Trp Cys Gly Phe Asp Pro His Gly Cys Cys Gly Asn Cys Gly Cys Leu
            100                 105                 110

Val Gly Phe Cys Tyr Gly Thr Gly Cys
            115                 120
```

<210> SEQ ID NO 140
<211> LENGTH: 121
<212> TYPE: PRT
<213> ORGANISM: Panax quinquefolius

<400> SEQUENCE: 140

```
Met Asp Asn Lys Lys Val Ala Leu Val Val Ala Met Val Val Val
1               5                   10                  15

Leu Ile Ser Thr Phe Ala Pro Leu Ala Leu Ala Ala Asp Glu Ala Gly
            20                  25                  30

Arg Ser Asp Gly Gly Asn Gly Asp Leu Ile Ala Val Glu Ser Val Ser
        35                  40                  45

Arg Ser Asn Gly Gly Asn Gly Asp Ser Val Thr Val Asp Thr Val Ser
        50                  55                  60

Trp Val Ser Ser Asn Arg Lys Thr Leu Arg Ser Ser Ile Phe Leu Pro
65                  70                  75                  80

Gln Gly Tyr Leu Pro Asp Gly Gly Leu Gly Cys Ile Ser Ser Gly Gly
                85                  90                  95

Trp Cys Gly Phe Asp Leu His Gly Cys Cys Gly Asn Cys Gly Cys Leu
            100                 105                 110

Val Gly Phe Cys Tyr Gly Thr Gly Cys
            115                 120
```

<210> SEQ ID NO 141
<211> LENGTH: 113
<212> TYPE: PRT
<213> ORGANISM: Panax quinquefolius

<400> SEQUENCE: 141

```
Val Ala Val Ala Met Val Val Val Leu Ile Ser Thr Phe Ala Pro Leu
1               5                   10                  15
```

Ala Leu Ala Ala Asp Glu Ala Gly Arg Ser Asp Gly Gly Asn Gly Asp
                    20                  25                  30

Leu Ile Ala Val Glu Ser Val Ser Arg Ser Asn Gly Asn Gly Asp
                35                  40                  45

Ser Val Thr Val Asp Thr Val Ser Trp Val Ser Ser Asn Arg Lys Thr
 50                      55                  60

Leu Arg Ser Ser Ile Phe Leu Pro Gln Gly Tyr Leu Pro Asp Gly Gly
 65                  70                  75                  80

Leu Gly Cys Lys Ser Gly Gly Ser Trp Cys Gly Phe Cys Pro His Gly
                    85                  90                  95

Cys Cys Gly Asn Cys Gly Cys Leu Val Gly Phe Cys Tyr Gly Thr Gly
                100                 105                 110

Cys

<210> SEQ ID NO 142
<211> LENGTH: 121
<212> TYPE: PRT
<213> ORGANISM: Panax quinquefolius

<400> SEQUENCE: 142

Met Asp Asn Lys Lys Val Ala Leu Val Val Ala Met Val Val Val
 1               5                  10                  15

Leu Ile Ser Thr Phe Ala Pro Leu Ala Leu Ala Ala Asp Glu Ala Gly
                    20                  25                  30

Arg Ser Asp Gly Gly Asn Gly Asp Leu Ile Ala Val Glu Ser Val Ser
                35                  40                  45

Arg Ser Asn Gly Gly Asn Gly Asp Ser Val Thr Val Asp Thr Val Ser
 50                      55                  60

Trp Val Ser Ser Asn Arg Lys Thr Leu Arg Ser Ser Ile Phe Leu Pro
 65                  70                  75                  80

Gln Gly Tyr Leu Pro Asp Gly Gly Leu Gly Cys Ile Phe Ser Gly Gly
                    85                  90                  95

Trp Cys Gly Phe Asp Leu His Gly Cys Cys Gly Asn Cys Gly Cys Leu
                100                 105                 110

Val Gly Phe Cys Tyr Gly Thr Gly Cys
                115                 120

<210> SEQ ID NO 143
<211> LENGTH: 41
<212> TYPE: PRT
<213> ORGANISM: Panax quinquefolius

<400> SEQUENCE: 143

Ala Leu Pro Asp Gly Gly Leu Gly Cys Leu Lys Asn Gly Gln Phe Cys
 1               5                  10                  15

Trp Gly Asn Pro Ser Gly Cys Cys Gly Asn Cys Gly Cys Leu Ile Ile
                    20                  25                  30

Pro Gly Val Cys Tyr Gly Thr Gly Cys
                35                  40

<210> SEQ ID NO 144
<211> LENGTH: 94
<212> TYPE: PRT
<213> ORGANISM: Panax quinquefolius

<400> SEQUENCE: 144

Met Val Val Leu Thr Asp Leu Ile Leu Ala Ala Asp Asp Met Ala Asp
 1               5                  10                  15

His Ser Asp Gly Gly Thr Asp Ile Ser Asp Gly Gly Asn Glu Val Leu
            20                  25                  30

Ile Asp Ala Ser Ala Gly Val Ser Phe Tyr Lys Lys Leu Pro Met Ser
        35                  40                  45

Arg Phe Phe Leu Arg Glu Arg Tyr Leu Pro Asp Gly Leu Gly Cys
    50                  55                  60

Ile Pro Gly Gly Phe Cys Met Phe Glu Pro Leu Ser Cys Cys His
65              70                  75                  80

Asn Cys Gly Cys Leu Leu Val Pro Gly Val Cys Tyr Cys Gly
                85                  90

<210> SEQ ID NO 145
<211> LENGTH: 94
<212> TYPE: PRT
<213> ORGANISM: Panax notoginseng

<400> SEQUENCE: 145

Met Ala Val Leu Thr Asp Leu Thr Leu Ala Ala Asp Asp Lys Ala Gly
1               5                   10                  15

His Ser Asp Gly Gly Ala Asp Arg Ser Asp Gly Gly Asn Glu Val Leu
            20                  25                  30

Ile Asp Ala Pro Gly Gly Ala Ser Val Tyr Lys Asn Leu Pro Leu Ser
        35                  40                  45

Arg Phe Phe Leu Arg Glu Lys Tyr Leu Pro Asp Gly Leu Gly Cys
    50                  55                  60

Ile Pro Asn Gly Gly Phe Cys Met Phe Glu Pro Leu Ser Cys Cys Val
65              70                  75                  80

Asn Cys Gly Cys Ile Leu Val Pro Gly Val Cys Tyr Cys Gly
                85                  90

<210> SEQ ID NO 146
<211> LENGTH: 83
<212> TYPE: PRT
<213> ORGANISM: Panax quinquefolius

<400> SEQUENCE: 146

Met Glu Asn Lys Lys Val Ala Val Met Val Val Leu Ala Ile Met
1               5                   10                  15

Leu Ala Leu Ala Ile Ala Ser Arg Glu Ala Gly His Ser Gly Asp Asp
            20                  25                  30

Pro Gly Thr Gly Val Arg Lys Met Leu Arg Pro Glu Ile Ile Asp Pro
        35                  40                  45

Asp Gly Ser Cys Leu Lys Val Gly Lys Ile Cys Leu Gly Arg Gly Leu
    50                  55                  60

Lys Glu Cys Cys Pro Ser Ala Thr Cys Gly Cys Leu Leu Gly Phe Cys
65              70                  75                  80

Ile Lys Cys

<210> SEQ ID NO 147
<211> LENGTH: 6
<212> TYPE: PRT
<213> ORGANISM: artificial sequence
<220> FEATURE:
<223> OTHER INFORMATION: artificial sequence
<220> FEATURE:
<221> NAME/KEY: MISC_FEATURE
<222> LOCATION: (1)..(1)
<223> OTHER INFORMATION: X is Ac-K
<220> FEATURE:

```
<221> NAME/KEY: MISC_FEATURE
<222> LOCATION: (6)..(6)
<223> OTHER INFORMATION: X is W-NH2

<400> SEQUENCE: 147

Xaa Ser Gly Gly Ala Xaa
1               5

<210> SEQ ID NO 148
<211> LENGTH: 6
<212> TYPE: PRT
<213> ORGANISM: artificial sequence
<220> FEATURE:
<223> OTHER INFORMATION: artificial sequence
<220> FEATURE:
<221> NAME/KEY: MISC_FEATURE
<222> LOCATION: (1)..(1)
<223> OTHER INFORMATION: X is Ac-A
<220> FEATURE:
<221> NAME/KEY: MISC_FEATURE
<222> LOCATION: (6)..(6)
<223> OTHER INFORMATION: X is W-NH2

<400> SEQUENCE: 148

Xaa Ser Gly Gly Ala Xaa
1               5

<210> SEQ ID NO 149
<211> LENGTH: 6
<212> TYPE: PRT
<213> ORGANISM: artificial sequence
<220> FEATURE:
<223> OTHER INFORMATION: artificial sequence
<220> FEATURE:
<221> NAME/KEY: MISC_FEATURE
<222> LOCATION: (1)..(1)
<223> OTHER INFORMATION: X is Ac-K
<220> FEATURE:
<221> NAME/KEY: MISC_FEATURE
<222> LOCATION: (6)..(6)
<223> OTHER INFORMATION: X is W-NH2

<400> SEQUENCE: 149

Xaa Ala Gly Gly Ala Xaa
1               5

<210> SEQ ID NO 150
<211> LENGTH: 6
<212> TYPE: PRT
<213> ORGANISM: artificial sequence
<220> FEATURE:
<223> OTHER INFORMATION: artificial sequence
<220> FEATURE:
<221> NAME/KEY: MISC_FEATURE
<222> LOCATION: (1)..(1)
<223> OTHER INFORMATION: X is Ac-K
<220> FEATURE:
<221> NAME/KEY: MISC_FEATURE
<222> LOCATION: (6)..(6)
<223> OTHER INFORMATION: X is A-NH2

<400> SEQUENCE: 150

Xaa Ser Gly Gly Ala Xaa
1               5

<210> SEQ ID NO 151
<211> LENGTH: 71
<212> TYPE: PRT
<213> ORGANISM: Angiopteris evecta

<400> SEQUENCE: 151
```

Pro Leu Thr Ala Leu Ala Ala Arg Asn Glu Ile Ile Ala Leu Asp Gly
1               5                   10                  15

Glu Ala Lys Asn Asn Gln Leu Asn Tyr Leu Ala Met Val Leu Asp Val
            20                  25                  30

Asn Arg Pro Arg Asn Cys Ile Pro Lys Gly Gly Trp Cys Leu Phe Asp
            35                  40                  45

Ile Met Gly Cys Cys Lys Pro Cys Gly Cys Leu Ala Gly Phe Cys Trp
50                  55                  60

Val Val Gly Asp Asp Cys Asn
65                  70

<210> SEQ ID NO 152
<211> LENGTH: 106
<212> TYPE: PRT
<213> ORGANISM: Amaranthus retroflexus

<400> SEQUENCE: 152

Met Ala Ile Met Ile Lys Gln Asn Ala Ile Ile Leu Val Leu Val Phe
1               5                   10                  15

Ser Ile Phe Leu Leu Val Thr Lys Pro His Ser Ala Ser Ala Glu Asn
            20                  25                  30

Asp Ile Ala Leu Val Arg Ala Gln Ala Arg Val Arg Gly Gln Ala Leu
            35                  40                  45

Arg Arg Leu Leu Pro Leu Ser Met Ile Met Leu Glu Glu Leu Asn Val
50                  55                  60

Asn Asn Gly Pro Leu Gly Cys Val Pro Lys Gly Thr Pro Cys Leu Tyr
65                  70                  75                  80

Lys Pro Glu Pro Cys Cys Gly Ala Asn Cys Phe Cys Asp Thr Ser Ala
                85                  90                  95

Tyr Thr Phe Gln Tyr Val Cys Lys Cys Tyr
            100                 105

<210> SEQ ID NO 153
<211> LENGTH: 88
<212> TYPE: PRT
<213> ORGANISM: Agrostis stolonifera
<220> FEATURE:
<221> NAME/KEY: misc_feature
<222> LOCATION: (25)..(25)
<223> OTHER INFORMATION: Xaa can be any naturally occurring amino acid

<400> SEQUENCE: 153

Met Ala Thr Thr Lys Met Ala Val Val Ala Ile Leu Ala Ala Leu Leu
1               5                   10                  15

Leu Met Ala Ala Val Glu Pro Ala Xaa Ala Thr Pro Pro Ser Met Leu
            20                  25                  30

Ala Ala Arg Lys Leu Gln Met Pro Arg Leu Met Asp Val Val Ser Ala
            35                  40                  45

Glu Ser Lys Leu Ala Cys Leu Pro Ser Gly Gly Phe Cys Met Phe Arg
50                  55                  60

Pro Thr Asp Cys Cys Gly Asn Cys Gly Cys Leu Tyr Pro Val Gly Val
65                  70                  75                  80

Cys Tyr Gly Ser Arg Cys Glu Glu
                85

<210> SEQ ID NO 154
<211> LENGTH: 83
<212> TYPE: PRT

<213> ORGANISM: Blasia sp.

<400> SEQUENCE: 154

Met Ala Asp Arg Ser Asp Gly Gly Thr Asp Ser Ser Asp Gly Gly Asn
1               5                   10                  15

Glu Val Leu Ile Asp Ala Ser Gly Gly Val Ser Phe Tyr Lys Lys Leu
            20                  25                  30

Pro Met Ser Arg Phe Phe Leu Arg Glu Arg Tyr Leu Pro Asp Gly Gly
        35                  40                  45

Leu Gly Cys Leu Lys Asn Gly Glu Phe Cys Trp Gly Asp Pro Ser Gly
    50                  55                  60

Cys Cys Gly Asn Cys Gly Cys Leu Ile Ile Pro Gly Val Cys Tyr Gly
65                  70                  75                  80

Thr Gly Cys

<210> SEQ ID NO 155
<211> LENGTH: 116
<212> TYPE: PRT
<213> ORGANISM: Bazzania trilobata

<400> SEQUENCE: 155

Met Ala Pro Ala Ala Ser Phe Lys Leu Ala Thr Ile Ala Cys Phe Val
1               5                   10                  15

Phe Leu Leu Ser Gly Leu Thr Phe Gly Asp Glu Val Leu Pro Lys Met
            20                  25                  30

Ala Glu Glu Gly Ser Glu Ile Val Ile Glu Gly Ile Ile Asn Tyr Lys
        35                  40                  45

Val His Pro Asn Asn Ile Asp Asn Asn Ser Lys Gly Thr Thr Ile Gly
    50                  55                  60

Thr Pro His Phe Asn Asn Gly Thr Pro Asn Ser Asn Ile Lys Gln Val
65                  70                  75                  80

Val Asp Gly Asn Leu Lys Cys Leu Asn Gly Gly Tyr Cys Gly Ser
            85                  90                  95

Phe Thr Arg Glu Ala Cys Cys Tyr Asn Cys Val Cys Met Met Ala Phe
            100                 105                 110

Cys Val Cys Gly
        115

<210> SEQ ID NO 156
<211> LENGTH: 99
<212> TYPE: PRT
<213> ORGANISM: Coffea canephora

<400> SEQUENCE: 156

Met Ala Phe Lys His Ser Phe Phe Val Val Leu Val Leu Leu Ala Ser
1               5                   10                  15

Ser Val Val Leu Gly Gln Asp Glu Ala Gly Glu Ala Thr Glu Thr Thr
            20                  25                  30

Asn Ala Val Lys Thr Ala Ser Arg Lys Met Leu Pro Ile Gly Gly Gln
        35                  40                  45

Ile Ile Lys Met Leu Gly Val Gly Val His Asp Gly Gln Glu Gly Glu
    50                  55                  60

Cys Ser Pro Phe Gly Lys Pro Cys Arg Tyr Asn Pro Trp Gly Cys Cys
65                  70                  75                  80

Asp Ser Cys Val Cys Val Ala Thr Pro Ala Asp Glu Gly Arg Cys Leu
            85                  90                  95

Gly Asn Cys

<210> SEQ ID NO 157
<211> LENGTH: 104
<212> TYPE: PRT
<213> ORGANISM: Daucus carota

<400> SEQUENCE: 157

```
Met Glu Met Lys Lys Val Phe Leu Leu Ser Leu Ala Leu Val Leu Ile
1               5                   10                  15

Ser Ala Met Val Ser Thr Ala Ser Val Glu Thr Ile Val Glu Ala Ala
            20                  25                  30

Gly Ser Asn Ile Met Ser Asn Glu Met Val Thr Arg Gly Ser Asp Gly
        35                  40                  45

Leu Thr Tyr Tyr Asn Lys Ser Pro Leu Ser Arg Ile Phe Leu Pro Lys
    50                  55                  60

Gly Asn Val Ala Asp Gly Asp Cys Leu Pro Asn Gly Gly Phe Cys Met
65                  70                  75                  80

Phe Arg Pro Met Asp Cys Cys Gly Ser Cys Gly Cys Leu Tyr Pro Val
                85                  90                  95

Gly Val Cys Phe Gly Thr Gly Cys
            100
```

<210> SEQ ID NO 158
<211> LENGTH: 106
<212> TYPE: PRT
<213> ORGANISM: Daucus carota

<400> SEQUENCE: 158

```
Met Glu Ser Thr Lys Gly Cys Glu Ile His Phe Lys Ser Arg Leu Met
1               5                   10                  15

Leu Ile Ser Ile Leu Leu Ala Gly Val Val Leu Leu Ser Ala Ala Glu
            20                  25                  30

Thr Asn Thr Gly Ile Lys Ile Asn Pro Lys Ile Val Asp Asp Ser Asn
        35                  40                  45

Lys Arg Ser Asn Gly Leu Thr Lys Leu Asp Lys Ser Pro Val Pro Ala
    50                  55                  60

Pro Ser Asn Ser Pro Gly Lys Arg Val Cys Tyr Pro Lys Gly His Glu
65                  70                  75                  80

Cys Arg Thr Asp Pro Thr Leu Cys Cys His Asn Cys Gly Cys Ile Met
                85                  90                  95

Pro Val Gly Val Cys Phe Gly Ile Asn Cys
            100                 105
```

<210> SEQ ID NO 159
<211> LENGTH: 97
<212> TYPE: PRT
<213> ORGANISM: Eragrostis curvula

<400> SEQUENCE: 159

```
Met Ala Thr Thr Lys Met Ala Val Val Ala Ile Leu Ala Ala Leu Leu
1               5                   10                  15

Leu Met Ala Ala Val Glu Pro Ala Ser Ala Thr Pro Pro Ser Lys Leu
            20                  25                  30

Ala Ala Arg Lys Leu Gln Leu Ala Leu Leu Ser Asp Val Ser Glu Glu
        35                  40                  45

Thr Gln Leu Ala Leu Leu Ser Asp Gly Ser Glu Glu Arg Gln Leu Gly
    50                  55                  60
```

Cys Leu Pro Ser Gly Gly Phe Cys Met Phe Arg Pro Lys Asp Cys Cys
65                  70                  75                  80

Gly Ser Cys Gly Cys Leu Tyr Pro Ile Gly Val Cys Phe Gly Ser Ser
                85                  90                  95

Cys

<210> SEQ ID NO 160
<211> LENGTH: 89
<212> TYPE: PRT
<213> ORGANISM: Eleusine coracana

<400> SEQUENCE: 160

Met Ala Thr Thr Lys Met Ala Val Val Ala Ile Leu Ala Ala Leu Leu
1               5                   10                  15

Leu Met Ala Ala Val Glu Pro Ala Ser Ala Thr Leu Pro Ser Glu Gln
                20                  25                  30

Leu Ala Ala Arg Lys Leu Gln Met Pro Arg Leu Ile Asp Ile Val Thr
            35                  40                  45

Ala Glu Thr Gln Leu Gly Cys Ile Pro Met Gly Gly Phe Cys Leu Phe
        50                  55                  60

Asn Leu Arg Gly Cys Cys Gly Ser Cys Gly Cys Leu Ala Gly Phe Cys
65                  70                  75                  80

Trp Arg Asp Ala Ser Ser Cys Asp Leu
                85

<210> SEQ ID NO 161
<211> LENGTH: 93
<212> TYPE: PRT
<213> ORGANISM: Eleusine coracana

<400> SEQUENCE: 161

Met Ala Thr Thr Lys Met Ala Met Val Ala Ile Leu Ala Ala Leu Leu
1               5                   10                  15

Leu Met Ala Ala Val Glu Pro Ala Ser Ala Thr Leu Pro Ser Glu Gln
                20                  25                  30

Leu Ala Ala Arg Lys Leu Gln Met Pro Arg Leu Ile Asp Ile Val Asn
            35                  40                  45

Ala Glu Val Ile Ala Glu Thr Gln Leu Gly Cys Ile Pro Met Gly Gly
        50                  55                  60

Phe Cys Leu Gly Asn Leu Arg Gly Cys Cys Gly Ser Cys Gly Cys Leu
65                  70                  75                  80

Ala Gly Phe Cys Trp Arg Pro Ala Ser Ser Cys Asp Ser
                85                  90

<210> SEQ ID NO 162
<211> LENGTH: 71
<212> TYPE: PRT
<213> ORGANISM: Elymus wawawaiensis

<400> SEQUENCE: 162

Met Ala Ala Val Glu Pro Ala Ser Ala Thr Pro Pro Ser Met Leu Ala
1               5                   10                  15

Ala Arg Lys Leu Gln Met Pro Arg Leu Met Asp Val Val Phe Ala Glu
                20                  25                  30

Ser Lys Leu Ala Cys Leu Pro Ser Gly Gly Phe Cys Met Phe Arg Pro
            35                  40                  45

Lys Asp Cys Cys Gly Asn Cys Gly Cys Leu Tyr Pro Ile Gly Val Cys

```
                  50                  55                  60

Tyr Gly Ser Arg Cys Glu Glu
 65                  70

<210> SEQ ID NO 163
<211> LENGTH: 96
<212> TYPE: PRT
<213> ORGANISM: Gossypium hirsutum

<400> SEQUENCE: 163

Met Glu Ser Leu Lys Lys Ile Val Phe Leu Ile Val Ala Ile Ser Leu
 1               5                  10                  15

Val Leu Gln Ala Thr Val Leu Pro Thr Ala Leu Ala Ala Arg Asn Glu
                20                  25                  30

Val Met Ser Ser Ala Ala Val Ser Lys Val Ala Asn Asp Ser Asn Gly
            35                  40                  45

Leu Ala Lys Val Phe Glu Lys Val Gly Pro Gly Cys Lys Pro Lys Gly
        50                  55                  60

Ser Phe Cys Leu Phe Asp Leu Gln Ser Cys Cys Arg Pro Cys Gly Cys
 65                  70                  75                  80

Leu Ala Gly Trp Cys Tyr Asn Ile Asp His Asp Cys Asn Glu Tyr Thr
                85                  90                  95

<210> SEQ ID NO 164
<211> LENGTH: 104
<212> TYPE: PRT
<213> ORGANISM: Griselinia littoralis

<400> SEQUENCE: 164

Met Glu Asn Lys Gln Val Ala Leu Val Val Leu Ala Ala Met Val Val
 1               5                  10                  15

Leu Ile Ser Thr Phe Ala Thr Leu Ala Leu Ala Asp Gly Glu Ala Asp
                20                  25                  30

Leu Ser Asp Gly Asn Gly Val Leu Ile Gly Gly Pro Gly Gly Val Arg
            35                  40                  45

Phe Tyr Lys Lys Thr Pro Leu Ser Arg Ile Phe Met Pro Lys Gly Tyr
        50                  55                  60

Leu Pro Asp Gly Ser Leu Gly Cys Ile Ser Ser Gly Gly Phe Cys Met
 65                  70                  75                  80

Phe Asn Pro Arg Asp Cys Cys Gly Ser Cys Gly Cys Leu Tyr Pro Met
                85                  90                  95

Gly Ile Cys Tyr Gly Ser Ser Cys
            100

<210> SEQ ID NO 165
<211> LENGTH: 96
<212> TYPE: PRT
<213> ORGANISM: Gossypium raimondii

<400> SEQUENCE: 165

Met Glu Ser Leu Lys Asn Ile Val Phe Leu Ile Val Ala Ile Ser Leu
 1               5                  10                  15

Val Leu Gln Ala Thr Val Pro Pro Thr Ala Leu Ala Ala Arg Asn Glu
                20                  25                  30

Val Met Ser Ser Ala Ala Val Ser Lys Val Ala Asn Asp Ser Asn Gly
            35                  40                  45

Leu Ala Lys Val Phe Gln Lys Val Gly Pro Gly Cys Lys Pro Ile Gly
        50                  55                  60
```

Ser Phe Cys Leu Phe Asp Leu Thr Ser Cys Cys Arg Pro Cys Gly Cys
65                  70                  75                  80

Leu Ala Gly Phe Cys Tyr Asn Leu Asp His Asn Cys Asn Glu Tyr Thr
                85                  90                  95

<210> SEQ ID NO 166
<211> LENGTH: 96
<212> TYPE: PRT
<213> ORGANISM: Gossypium raimondii

<400> SEQUENCE: 166

Met Glu Ser Leu Lys Asn Ile Val Phe Leu Ile Val Ala Ile Ser Leu
1               5                   10                  15

Val Leu Gln Ala Thr Val Pro Pro Thr Ala Leu Ala Ala Arg Asn Glu
                20                  25                  30

Val Met Ser Ser Ala Ala Val Ser Lys Val Ala Asn Gly Ser Asn Gly
            35                  40                  45

Leu Ala Val Val Phe Glu Lys Val Gly Ser Gly Cys Lys Pro Lys Gly
        50                  55                  60

Ser Phe Cys Leu Phe Asp Leu Thr Ser Cys Cys Arg Pro Cys Gly Cys
65                  70                  75                  80

Leu Ala Gly Trp Cys Tyr Asn Tyr Asp His Glu Cys Asn Glu Tyr Thr
                85                  90                  95

<210> SEQ ID NO 167
<211> LENGTH: 85
<212> TYPE: PRT
<213> ORGANISM: Gossypium raimondii

<400> SEQUENCE: 167

Met Glu Trp Cys Lys Lys Phe Ala Phe Leu Met Val Ala Met Val Leu
1               5                   10                  15

Leu Gln Ser Met Val Pro Pro Thr Ala Leu Ala Ala Arg Asn Asn Val
                20                  25                  30

Met Glu Tyr Asn Pro Leu Ala Ser Val Phe Ser Arg Glu Gly Pro Gly
            35                  40                  45

Cys Ile Ala Lys Gly Gly Phe Cys Leu Phe Asp Leu Thr Ser Cys Cys
        50                  55                  60

Arg Pro Cys Gly Cys Leu Ala Gly Trp Cys Tyr Asn Ile Asp His Asp
65                  70                  75                  80

Cys Lys Glu Tyr Thr
                85

<210> SEQ ID NO 168
<211> LENGTH: 86
<212> TYPE: PRT
<213> ORGANISM: Gossypium raimondii

<400> SEQUENCE: 168

Met Glu Trp Cys Lys Lys Phe Ala Phe Leu Met Phe Ala Met Ala Leu
1               5                   10                  15

Leu Leu Gln Ala Met Val Pro Pro Thr Ala Leu Ala Ala Arg Asn Asn
                20                  25                  30

Val Met Glu Tyr Asn Pro Leu Ala Ser Ile Val Ser Arg Glu Gly Pro
            35                  40                  45

Gly Cys Ile Ala Lys Gly Gly Phe Cys Leu Phe Asp Leu Thr Ser Cys
        50                  55                  60

Cys Arg Pro Cys Gly Cys Leu Ala Gly Trp Cys Tyr Asn Ile Asp His
65                  70                  75                  80

Asp Cys Asn Glu Tyr Ala
                85

<210> SEQ ID NO 169
<211> LENGTH: 102
<212> TYPE: PRT
<213> ORGANISM: Gossypium raimondii

<400> SEQUENCE: 169

Met Gly Leu Leu His Leu Gln Ala Ile Pro His Thr Lys Asn Ile Ile
1               5                   10                  15

Met Glu Arg Cys Lys Lys Phe Ala Phe Leu Met Val Ala Met Ala Leu
                20                  25                  30

Leu Leu Gln Ser Met Val Pro Pro Thr Ala Leu Ala Ala Leu Asn Asn
            35                  40                  45

Val Met Glu Tyr Asn Pro Leu Ala Ser Val Phe Ser Arg Glu Gly Pro
50                  55                  60

Gly Cys Ile Ala Lys Gly Gly Phe Cys Leu Phe Asp Leu Thr Ser Cys
65                  70                  75                  80

Cys Arg Pro Cys Gly Cys Leu Ala Gly Trp Cys Tyr Asn Ile Asp His
                85                  90                  95

Asp Cys Asn Glu Tyr Thr
                100

<210> SEQ ID NO 170
<211> LENGTH: 93
<212> TYPE: PRT
<213> ORGANISM: Hibiscus cannabinus

<400> SEQUENCE: 170

Met Glu Ser Cys Lys Lys Leu Ala Phe Leu Ile Val Ala Val Ala Leu
1               5                   10                  15

Val Leu Gln Ala Thr Val Pro Leu Thr Ala Leu Ala Ala Arg Asn Glu
                20                  25                  30

Ile Ile Ala Leu Asp Gly Glu Ala Lys Asn Asn Gln Leu Asn Tyr Leu
            35                  40                  45

Ala Met Val Leu Asp Val Asn Arg Pro Arg Asn Cys Ile Pro Lys Gly
50                  55                  60

Gly Trp Cys Leu Phe Asp Ile Met Gly Cys Cys Lys Pro Cys Gly Cys
65                  70                  75                  80

Leu Ala Gly Phe Cys Trp Val Val Gly Asp Cys Asn
                85                  90

<210> SEQ ID NO 171
<211> LENGTH: 104
<212> TYPE: PRT
<213> ORGANISM: Hibbertia grossulariifolia

<400> SEQUENCE: 171

Met Val Leu Ile Ser Thr Phe Thr Pro Leu Ala Leu Ala Ala Asp Glu
1               5                   10                  15

Val Ser Arg Ser Asp Gly Gly Asn Gly Asp Leu Phe Ala Val Glu Thr
                20                  25                  30

Ile Ser Arg Ser Asn Gly Gly Lys Gly Asp Ser Thr Ser Ala His Thr
            35                  40                  45

Val Ser Trp Val Ser Ser Asn Arg Lys Thr Leu Arg Ser Ser Leu Phe

```
                      50                   55                    60
Leu Pro Gln Gly Tyr Ile Arg Glu Ser Cys Ser Pro Leu Gly Lys
 65                  70                  75                   80

Cys Gly Asp Leu Val Glu Cys Cys Ser Gly Cys Val Cys Ile Trp Pro
                     85                  90                  95

Thr Tyr Thr Cys Val Gly His Cys
               100

<210> SEQ ID NO 172
<211> LENGTH: 131
<212> TYPE: PRT
<213> ORGANISM: Hedera helix

<400> SEQUENCE: 172

Met Asp Asn Lys Lys Val Ala Leu Val Val Ala Val Ala Ala Met Val
 1               5                  10                  15

Met Val Leu Ile Ser Thr Phe Thr Pro Leu Ala Leu Ala Ala Asp Asp
                20                  25                  30

Gln Ala Gly Leu Ser Asp Gly Gly Asn Gly Asp Leu Ile Ala Val Glu
            35                  40                  45

Ser Met Ser Arg Ser Asn Gly Gly Lys Gly Asp Ser Ile Ala Ala Asp
 50                 55                  60

Ser Val Asn Trp Val Ser Ser Asn Arg Lys Thr Leu Arg Ser Arg Leu
 65                 70                  75                  80

Phe Leu Pro Gln Gly Tyr Leu Pro Asp Ser Gly Leu Val Gly Cys Gln
                85                  90                  95

Pro Phe Asp Ala Pro Cys Asp Thr Phe Tyr Gly Phe Tyr Cys Cys Gly
               100                 105                 110

Ser Cys Thr Cys Thr Tyr Val Asp Phe Trp His Thr Ser Arg Cys Thr
               115                 120                 125

Gly Ser Cys
       130

<210> SEQ ID NO 173
<211> LENGTH: 119
<212> TYPE: PRT
<213> ORGANISM: Heracleum lanatum

<400> SEQUENCE: 173

Met Asn Asn Val Asp Thr His Arg Ala Lys Gln Ser Ile Phe Ile Met
 1               5                  10                  15

Glu Met Lys Lys Val Phe Trp Ala Ser Leu Thr Val Val Leu Ile Ser
                20                  25                  30

Ala Met Val Ser Met Ala Ala Val Glu Thr Ile Ile Glu Thr Ala Arg
            35                  40                  45

Ser Asn Ala Ile Ser Asn Glu Ile Val Thr Arg Gly Ser Asp Gly Leu
 50                 55                  60

Ser Tyr Tyr Asn Lys Ser Pro Met Ser Arg Ile Phe Leu Pro Glu Gly
 65                 70                  75                  80

Asn Val Ala Asp Gly Ala Cys Leu Pro Ala Gly Gly Phe Cys Met Phe
                85                  90                  95

Arg Pro Met Asp Cys Cys Gly Thr Cys Gly Cys Leu Tyr Pro Val Gly
               100                 105                 110

Val Cys Phe Gly Asn Asp Cys
               115
```

```
<210> SEQ ID NO 174
<211> LENGTH: 58
<212> TYPE: PRT
<213> ORGANISM: Lennoa madreporoides

<400> SEQUENCE: 174

Ser Ala Val Pro Ala Leu Ser Ser Met Arg Gly Ser Glu Met Ile Ile
1               5                   10                  15

Gln Ser Val Ala Glu Pro Gln Glu Asn Cys Ile Gly Ala Gly Gly Phe
            20                  25                  30

Cys Met Phe Asn Pro Met Asp Cys Cys Gly Asn Cys Gly Cys Leu Tyr
        35                  40                  45

Pro Val Gly Ile Cys Phe Gly Thr Gly Cys
    50                  55

<210> SEQ ID NO 175
<211> LENGTH: 116
<212> TYPE: PRT
<213> ORGANISM: Microtea madreporoides

<400> SEQUENCE: 175

Met Ala Pro Ala Ala Ser Phe Lys Leu Ala Thr Ile Ala Cys Phe Val
1               5                   10                  15

Phe Leu Leu Ser Gly Leu Thr Phe Gly Asp Glu Val Leu Pro Lys Met
            20                  25                  30

Ala Glu Glu Gly Ser Glu Ile Val Ile Glu Ile Ile Asn Tyr Lys
        35                  40                  45

Val His Pro Asn Ile Asp Asn Asn Ser Lys Gly Thr Thr Ile Gly
    50                  55                  60

Thr Pro His Phe Asn Asn Gly Thr Pro Asn Ser Asn Ile Lys Gln Val
65                  70                  75                  80

Val Asp Gly Asn Leu Lys Cys Leu Asn Gly Gly Tyr Cys Gly Ser
            85                  90                  95

Phe Thr Arg Glu Ala Cys Cys Tyr Asn Cys Val Cys Met Met Ala Phe
        100                 105                 110

Cys Val Cys Gly
        115

<210> SEQ ID NO 176
<211> LENGTH: 125
<212> TYPE: PRT
<213> ORGANISM: Mollugo nudicaulis
<220> FEATURE:
<221> NAME/KEY: misc_feature
<222> LOCATION: (92)..(92)
<223> OTHER INFORMATION: Xaa can be any naturally occurring amino acid

<400> SEQUENCE: 176

Met Ala Ala Asn Ala Thr Ala Tyr Leu Asn Lys Ser Gly Leu Ala Pro
1               5                   10                  15

Ser Val Pro Gly Leu Gly Asn Ile Leu Arg Leu Gly Ala Ile Pro Thr
            20                  25                  30

Glu Arg Ser Ser Ser Ser Glu Ile Ser Asp Glu Lys Val Val Met Ile
        35                  40                  45

Glu Glu Ile Met Glu Ile Pro Arg Asp Asp Glu Val Val Ala Phe Gly
    50                  55                  60

Met Thr Thr Thr Asn Asn Asp Ile Asn Ile Gly Lys Leu Ser Asp
65                  70                  75                  80

Asp Thr Ile Arg Gly Thr Asn Asn Tyr Ala Tyr Xaa Leu Arg Cys Lys
```

```
                        85                  90                  95

Ser Ala Gly Glu Trp Cys Gly Phe Ser Trp Thr Asp Cys Cys Asn Ser
                100                 105                 110

Cys Gly Cys Leu Ala Gly Phe Cys Tyr Gly Thr Ser Cys
            115                 120                 125

<210> SEQ ID NO 177
<211> LENGTH: 103
<212> TYPE: PRT
<213> ORGANISM: Myodocarpus sp.

<400> SEQUENCE: 177

Met Glu Asn Lys Lys Val Ala Leu Val Val Ala Ala Met Val Val
1               5                   10                  15

Leu Ile Ser Ser Leu Ala Glu Gly Glu Thr Val Gly Ser Asp Gly Asn
                20                  25                  30

Gly Val Leu Ile Gly Gly Gly Ser Gly Arg Val Ser Ser Tyr Lys Arg
            35                  40                  45

Thr Pro Leu Ser Lys Ile Phe Met Pro Thr Glu Tyr Ile Val Ser Gly
        50                  55                  60

Gly Gly Leu Ser Cys Ile Pro Lys Gly Gly Phe Cys Leu Phe Asp Leu
65                  70                  75                  80

Arg Gly Cys Cys Gly Met Cys Gly Cys Leu Ala Gly Val Cys Phe Asn
                85                  90                  95

Tyr Asp His Pro Cys Glu Glu
            100

<210> SEQ ID NO 178
<211> LENGTH: 39
<212> TYPE: PRT
<213> ORGANISM: Menyanthes trifoliata

<400> SEQUENCE: 178

Asp Gly Gly Pro Gln Asn Cys Leu Ser Ser Gly Gly Phe Cys Met Phe
1               5                   10                  15

Arg Pro Asn Asp Cys Cys Gly Asn Cys Gly Cys Leu Tyr Pro Val Gly
                20                  25                  30

Ile Cys Tyr Gly Thr Gly Cys
        35

<210> SEQ ID NO 179
<211> LENGTH: 88
<212> TYPE: PRT
<213> ORGANISM: Oryza sativa

<400> SEQUENCE: 179

Met Ala Ser Thr Lys Met Ala Val Val Ala Ile Leu Ala Ala Leu Leu
1               5                   10                  15

Leu Met Ala Ala Val Glu Pro Ala Leu Ala Thr Pro Pro Ser Leu Leu
                20                  25                  30

Pro Ala Arg Lys Leu Gln Met Pro Arg Leu Met Asp Val Val Ser Ala
            35                  40                  45

Glu Ser Lys Leu Ala Cys Leu Pro Ala Gly Gly Phe Cys Met Phe Arg
        50                  55                  60

Pro Met Asp Cys Cys Gly Asn Cys Gly Cys Leu Tyr Pro Val Gly Val
65                  70                  75                  80

Cys Tyr Gly Ser Arg Cys Glu Glu
                85
```

<210> SEQ ID NO 180
<211> LENGTH: 88
<212> TYPE: PRT
<213> ORGANISM: Pholisma arenarium

<400> SEQUENCE: 180

Met Ala Ser Thr Lys Met Ala Val Val Ala Ile Leu Ala Ala Leu Leu
1               5                   10                  15

Leu Met Ala Ala Val Glu Pro Ala Leu Ala Thr Pro Pro Ser Leu Leu
            20                  25                  30

Pro Ala Arg Lys Leu Gln Met Pro Arg Leu Met Asp Val Val Ser Ala
        35                  40                  45

Glu Ser Lys Leu Ala Cys Leu Pro Ala Gly Gly Phe Cys Met Phe Arg
    50                  55                  60

Pro Met Asp Cys Cys Gly Asn Cys Gly Cys Leu Tyr Pro Val Gly Val
65                  70                  75                  80

Cys Tyr Gly Ser Arg Cys Glu Glu
                85

<210> SEQ ID NO 181
<211> LENGTH: 75
<212> TYPE: PRT
<213> ORGANISM: Pholisma arenarium

<400> SEQUENCE: 181

Met Glu Arg Val Ser Trp Lys Leu Ala Phe Leu Met Val Leu Leu Leu
1               5                   10                  15

Cys Ala Ser Val Pro Ala Leu Ser Ser Met Arg Gly Ser Glu Met Ile
            20                  25                  30

Ile Lys Ser Leu Ala Glu Pro Gln Glu Asn Cys Ile Ser Ala Gly Gly
        35                  40                  45

Phe Cys Phe Phe Asp Pro Met Asn Cys Cys Gly Asn Cys Gly Cys Leu
    50                  55                  60

Tyr Pro Val Gly Ile Cys Val Gly Thr Asn Cys
65                  70                  75

<210> SEQ ID NO 182
<211> LENGTH: 104
<212> TYPE: PRT
<213> ORGANISM: Polyscias fruticosa

<400> SEQUENCE: 182

Met Val Leu Ile Ser Thr Phe Thr Pro Leu Ala Leu Ala Ala Asp Glu
1               5                   10                  15

Val Ser Arg Ser Asp Gly Gly Asn Gly Asp Leu Phe Ala Val Glu Thr
            20                  25                  30

Ile Ser Arg Ser Asn Gly Gly Lys Gly Asp Ser Thr Ser Ala Asp Thr
        35                  40                  45

Val Ser Trp Val Ser Ser Asn Arg Lys Thr Leu Arg Ser Ser Leu Phe
    50                  55                  60

Leu Pro Gln Gly Tyr Ile Arg Glu Ser Cys Ser Pro Leu Gly Gly Lys
65                  70                  75                  80

Cys Gly Asp Leu Val Glu Cys Cys Ser Gly Cys Val Cys Ile Trp Pro
                85                  90                  95

Thr Tyr Thr Cys Val Gly His Cys
            100

<210> SEQ ID NO 183
<211> LENGTH: 109
<212> TYPE: PRT
<213> ORGANISM: Polyscias fruticosa

<400> SEQUENCE: 183

Met Val Leu Ile Ser Thr Phe Thr Pro Leu Ala Leu Ala Ala Asp Glu
1               5                   10                  15

Val Ser Arg Ser Asp Gly Gly Asn Gly Asp Leu Phe Ala Val Glu Thr
            20                  25                  30

Ile Ser Arg Ser Asn Gly Gly Lys Gly Asp Ser Thr Ser Ala Asp Thr
        35                  40                  45

Val Ser Trp Val Ser Ser Asn Arg Lys Thr Leu Arg Ser Ser Leu Phe
    50                  55                  60

Leu Pro Gln Gln Gly Tyr Ile Arg Glu Ser Cys Ile Pro Leu Gly Gly
65                  70                  75                  80

Asp Cys Thr Asp Leu Phe Asp Cys Cys Pro Gly Cys Val Cys Ile Ile
                85                  90                  95

Thr Asp Leu Thr Cys Asp Gly Asn Cys Phe Arg Gly Ala
            100                 105

<210> SEQ ID NO 184
<211> LENGTH: 81
<212> TYPE: PRT
<213> ORGANISM: Polyscias fruticosa

<400> SEQUENCE: 184

Ala Val Glu Thr Ile Ser Arg Ser Asn Gly Gly Lys Gly Asp Ser Thr
1               5                   10                  15

Ser Ala Asp Thr Val Ser Trp Val Ser Ser Asn Arg Lys Thr Leu Arg
            20                  25                  30

Ser Ser Leu Phe Leu Pro Gln Gly Tyr Ile Arg Glu Ser Cys Leu Thr
        35                  40                  45

Leu Gly Leu Tyr Cys Gly Gly Ser Gly Glu Cys Cys Ser Gly Cys
    50                  55                  60

Leu Cys Val Tyr Pro Thr Leu Thr Cys Arg Gly Asn Cys Tyr Arg Gly
65                  70                  75                  80

Ala

<210> SEQ ID NO 185
<211> LENGTH: 84
<212> TYPE: PRT
<213> ORGANISM: Phyllanthus sp.

<400> SEQUENCE: 185

Met Glu Gly Asn Arg Lys Val Gly Phe Ile Val Ile Ala Val Ala Val
1               5                   10                  15

Leu Leu Val Ala Ser Glu Pro Ser Pro Ala Leu Ala Ser Arg Asn Trp
            20                  25                  30

Pro Met Ser Phe Leu Val Asp Gln Gly Ile Ala Pro Arg Glu Gly Leu
        35                  40                  45

Leu Gly Cys Ser Asp Pro Gly Tyr Cys Val Pro Phe Phe Gln Gly
    50                  55                  60

Cys Cys Asn Asp Cys Ser Cys Leu Asp Leu Gly Val Val Ala Gly Val
65                  70                  75                  80

Cys Val Cys Ile

<210> SEQ ID NO 186
<211> LENGTH: 80
<212> TYPE: PRT
<213> ORGANISM: Populus trichocarpa

<400> SEQUENCE: 186

Met Asp Ser Lys Lys Val Thr Leu Leu Met Val Ala Leu Val Phe
1               5                   10                  15

Val Ala Thr Ile Ala Pro Ser Ala Leu Ala Met Arg Gln Phe Pro Leu
            20                  25                  30

Leu Met Thr Ser Asn Ile Leu Leu Gln Asp Glu Ser Asn Leu Gly Cys
        35                  40                  45

Ile Ser Ser Gly Gly Trp Cys Phe Thr Gln Pro Lys Asn Cys Cys Gly
    50                  55                  60

Asn Cys Gly Cys Leu Tyr Pro Ile Gly Ile Cys Phe Gly Ser Asp Cys
65                  70                  75                  80

<210> SEQ ID NO 187
<211> LENGTH: 80
<212> TYPE: PRT
<213> ORGANISM: Populus trichocarpa

<400> SEQUENCE: 187

Met Asp Ser Lys Lys Val Thr Leu Leu Met Val Ala Leu Val Phe
1               5                   10                  15

Val Ala Thr Ile Ala Pro Ser Ala Leu Ala Met Arg Gln Phe Pro Leu
            20                  25                  30

Leu Met Thr Ser Asn Ile Leu Leu Gln Asp Glu Ser Asn Leu Gly Cys
        35                  40                  45

Ile Ser Ser Gly Gly Trp Cys Phe Pro Asn Pro Lys Asn Cys Cys Gly
    50                  55                  60

Asn Cys Gly Cys Leu Tyr Pro Ile Gly Ile Cys Phe Gly Ser Asp Cys
65                  70                  75                  80

<210> SEQ ID NO 188
<211> LENGTH: 65
<212> TYPE: PRT
<213> ORGANISM: Populus tremula

<400> SEQUENCE: 188

Phe Leu Ser His His Cys Pro Val Thr Leu Ala Met Arg Gln Phe Pro
1               5                   10                  15

Leu Leu Met Thr Ser Asn Ile Leu Leu Gln Asp Glu Ser Lys Leu Gly
            20                  25                  30

Cys Ile Ser Ser Gly Gly Phe Cys Phe Thr Gln Pro Met Asn Cys Cys
        35                  40                  45

Gly Asn Cys Gly Cys Leu Tyr Pro Leu Gly Ile Cys Tyr Gly Ser Asp
    50                  55                  60

Cys
65

<210> SEQ ID NO 189
<211> LENGTH: 81
<212> TYPE: PRT
<213> ORGANISM: Salix dasyclados

<400> SEQUENCE: 189

Met Asp Ser Lys Lys Ile Thr Leu Val Leu Met Val Ala Val Val Phe
1               5                   10                  15

```
Val Ala Thr Ile Ala His Ser Thr Leu Ala Val Arg Gln Phe Pro Pro
            20                  25                  30

Leu Leu Thr Ser Asn Ile Leu Leu Gln Asp Gly Ser Asn Glu Leu Gly
            35                  40                  45

Cys Leu Pro Ser Gly Gly Phe Cys Met Phe Gln Pro Met Asn Cys Cys
 50                      55                  60

Gly Asn Cys Gly Cys Leu Tyr Pro Ile Gly Val Cys Tyr Gly Ser Asn
 65                  70                  75                  80

Cys

<210> SEQ ID NO 190
<211> LENGTH: 94
<212> TYPE: PRT
<213> ORGANISM: Theobroma cacao

<400> SEQUENCE: 190

Met Asp Cys Lys Lys Leu Ala Phe Leu Phe Ala Ala Thr Ala Val Leu
 1               5                  10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Ile Arg His Pro
            35                  40                  45

Phe Ser Asn Ile Phe Met Pro Ser Lys Ser Gly Glu Asn Cys Leu Ser
 50                      55                  60

Ala Gly Gly Phe Cys Met Phe Asn Pro Met Asp Cys Cys Gly Asn Cys
 65                  70                  75                  80

Gly Cys Leu Tyr Pro Met Gly Ile Cys Tyr Gly Ser Gly Cys
                 85                  90

<210> SEQ ID NO 191
<211> LENGTH: 94
<212> TYPE: PRT
<213> ORGANISM: Theobroma cacao

<400> SEQUENCE: 191

Met Asp Cys Lys Lys Leu Ala Phe Leu Phe Ala Ala Thr Ala Val Leu
 1               5                  10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Ile Arg His Pro
            35                  40                  45

Phe Ser Asn Ile Phe Met Pro Ser Lys Ser Gly Glu Asn Cys Leu Ser
 50                      55                  60

Ala Gly Gly Phe Cys Met Phe Asn Pro Met Asp Cys Cys Gly Asn Cys
 65                  70                  75                  80

Gly Cys Leu Phe Pro Met Gly Ile Cys Tyr Gly Ser Gly Cys
                 85                  90

<210> SEQ ID NO 192
<211> LENGTH: 94
<212> TYPE: PRT
<213> ORGANISM: Theobroma cacao

<400> SEQUENCE: 192

Met Asp Ser Lys Lys Leu Ala Phe Leu Phe Ala Ala Thr Ala Val Leu
 1               5                  10                  15

Leu Val Ala Ala Met Thr Pro Thr Ala Phe Ala Ala Arg Asn Gly Val
```

```
                20                  25                  30
Val Pro Phe Ser Leu Asp Thr Asn Val Ala Val Asn Phe Arg His Pro
            35                  40                  45

Phe Ser Asn Ile Phe Met Pro Ser Lys Ser Gly Glu Asn Cys Leu Ser
        50                  55                  60

Ala Gly Gly Phe Cys Met Phe Asn Pro Met Asp Cys Cys Gly Asn Cys
65                  70                  75                  80

Gly Cys Leu Tyr Pro Met Gly Phe Cys Tyr Gly Ser Gly Cys
                85                  90
```

<210> SEQ ID NO 193
<211> LENGTH: 74
<212> TYPE: PRT
<213> ORGANISM: Theobroma cacao

<400> SEQUENCE: 193

```
Met Thr Pro Thr Ala Phe Pro Val Arg Asn Gly Val Val Pro Phe Ser
1               5                   10                  15

Phe Asp Thr Asn Val Ala Ala Ile Phe Arg His Pro Phe Ser Asn Ile
                20                  25                  30

Phe Met Pro Ser Lys Ser Gly Glu Asn Cys Leu Ser Ala Gly Gly Phe
            35                  40                  45

Cys Met Phe Asn Pro Met Asp Cys Cys Gly Asn Cys Gly Cys Leu Tyr
        50                  55                  60

Pro Leu Gly Phe Cys Tyr Gly Ser Gly Cys
65                  70
```

<210> SEQ ID NO 194
<211> LENGTH: 63
<212> TYPE: PRT
<213> ORGANISM: Theobroma cacao

<400> SEQUENCE: 194

```
Val Val Pro Phe Ser Leu Asp Thr Asn Val Ala Ala Asn Ile Arg His
1               5                   10                  15

Pro Phe Ser Asn Ile Phe Met Pro Ser Lys Ser Gly Glu Asn Cys Leu
                20                  25                  30

Ser Ala Gly Gly Phe Cys Met Phe Asp Pro Met Asp Cys Cys Gly Asn
            35                  40                  45

Cys Gly Cys Leu Tyr Pro Met Gly Ile Cys Tyr Gly Ser Gly Cys
        50                  55                  60
```

<210> SEQ ID NO 195
<211> LENGTH: 74
<212> TYPE: PRT
<213> ORGANISM: Theobroma cacao

<400> SEQUENCE: 195

```
Met Thr Pro Thr Ala Phe Ala Ala Arg Asn Gly Val Val Pro Phe Ser
1               5                   10                  15

Leu Asp Thr Asn Val Ala Ala Asn Phe Arg His Pro Phe Ser Ile Ile
                20                  25                  30

Phe Met Pro Ser Lys Ser Gly Glu Asn Cys Leu Ser Ala Gly Gly Phe
            35                  40                  45

Cys Met Phe Ile Pro Met Asp Cys Cys Gly Asn Cys Gly Cys Leu Phe
        50                  55                  60

Leu Met Gly Phe Cys Tyr Gly Ser Gly Cys
65                  70
```

<210> SEQ ID NO 196
<211> LENGTH: 94
<212> TYPE: PRT
<213> ORGANISM: Theobroma cacao

<400> SEQUENCE: 196

Met Asp Cys Lys Arg Leu Ala Phe Leu Phe Ala Ala Thr Ala Val Leu
1               5                   10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Phe Arg His Pro
        35                  40                  45

Phe Ser Asn Ile Phe Met Pro Ser Lys Ser Gly Glu Asn Cys Leu Ser
    50                  55                  60

Ala Gly Gly Phe Cys Met Phe Ile Pro Met Asp Cys Cys Gly Asn Cys
65                  70                  75                  80

Gly Cys Leu Phe Pro Met Gly Phe Cys Tyr Gly Ser Gly Cys
                85                  90

<210> SEQ ID NO 197
<211> LENGTH: 94
<212> TYPE: PRT
<213> ORGANISM: Theobroma cacao

<400> SEQUENCE: 197

Met Asp Cys Lys Lys Leu Ala Phe Leu Phe Ala Ala Thr Ala Val Leu
1               5                   10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Ile Arg His Pro
        35                  40                  45

Phe Ser Asn Ile Phe Met Pro Ser Lys Ser Gly Glu Asn Cys Leu Ser
    50                  55                  60

Ala Gly Gly Phe Cys Met Phe Asn Pro Met Asp Cys Cys Gly Asn Cys
65                  70                  75                  80

Gly Cys Leu Tyr Pro Met Gly Ile Cys Tyr Gly Ser Gly Cys
                85                  90

<210> SEQ ID NO 198
<211> LENGTH: 94
<212> TYPE: PRT
<213> ORGANISM: Theobroma cacao

<400> SEQUENCE: 198

Met Asp Cys Lys Lys Leu Ala Phe Leu Phe Ala Ala Thr Ala Val Leu
1               5                   10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Ile Arg His Pro
        35                  40                  45

Phe Ser Asn Ile Phe Met Pro Ser Lys Ser Gly Glu Asn Cys Pro Ser
    50                  55                  60

Ala Gly Gly Phe Cys Met Phe Asn Pro Met Asp Cys Cys Gly Asn Cys
65                  70                  75                  80

Gly Cys Leu Tyr Pro Met Gly Ile Cys Tyr Gly Ser Gly Cys
                85                  90

```
<210> SEQ ID NO 199
<211> LENGTH: 94
<212> TYPE: PRT
<213> ORGANISM: Theobroma cacao

<400> SEQUENCE: 199

Met Asp Cys Lys Lys Leu Ala Phe Leu Phe Ala Ala Thr Ala Val Leu
1               5                   10                  15

Leu Val Ala Ala Met Thr Pro Thr Ala Phe Ala Ala Arg Asn Gly Val
            20                  25                  30

Val Pro Phe Ser Leu Asp Thr Asn Val Ala Ala Asn Ile Arg His Pro
            35                  40                  45

Phe Ser Asn Ile Phe Met Pro Ser Lys Ser Gly Glu Asn Cys Leu Ser
        50                  55                  60

Ala Gly Gly Phe Cys Met Phe Asn Pro Met Asp Cys Cys Gly Asn Cys
65                  70                  75                  80

Gly Cys Leu Tyr Pro Leu Gly Ile Cys Tyr Gly Ser Gly Cys
                85                  90

<210> SEQ ID NO 200
<211> LENGTH: 88
<212> TYPE: PRT
<213> ORGANISM: Triticum aestivum

<400> SEQUENCE: 200

Met Ala Thr Thr Lys Met Ala Val Val Ala Ile Leu Ala Ala Leu Leu
1               5                   10                  15

Leu Met Ala Ala Val Glu Pro Ala Ser Ala Thr Pro Pro Ser Met Leu
            20                  25                  30

Ala Ala Arg Lys Leu Gln Met Pro Arg Leu Met Asp Val Val Leu Ala
            35                  40                  45

Glu Ser Lys Leu Ala Cys Leu Pro Ala Gly Gly Phe Cys Met Phe Arg
        50                  55                  60

Pro Met Asp Cys Cys Gly Asn Cys Gly Cys Leu Tyr Pro Ala Gly Val
65                  70                  75                  80

Cys Tyr Gly Thr Arg Cys Glu Glu
                85
```